United States Patent
Von Nussbaum et al.

(10) Patent No.: US 7,727,956 B2
(45) Date of Patent: Jun. 1, 2010

(54) DEOXONADEPSIPEPTIDES

(75) Inventors: Franz Von Nussbaum, Duesseldorf (DE); Nina Brunner, Essen (DE); Rainer Endermann, Wuppertal (DE); Chantal Fuerstner, Muelheim An der Ruhr (DE); Elke Hartmann, Wuppertal (DE); Jacques Ragot, Duesseldorf (DE); Guido Schiffer, Wuppertal (DE); Joachim Schuhmacher, Wuppertal (DE); Niels Svenstrup, Velbert (DE); Joachim Telser, Wuppertal (DE); Sonja Anlauf, Wuppertal (DE); Michael-Alexander Bruening, Berlin (DE)

(73) Assignee: Aicuris GmbH & Co. KG, Wuppertal (DE)

( * ) Notice: Subject to any disclaimer, the term of this patent is extended or adjusted under 35 U.S.C. 154(b) by 232 days.

(21) Appl. No.: 11/788,690

(22) Filed: Apr. 19, 2007

(65) Prior Publication Data

US 2008/0058253 A1    Mar. 6, 2008

Related U.S. Application Data

(63) Continuation of application No. PCT/EP2005/010858, filed on Oct. 8, 2005.

(30) Foreign Application Priority Data

Oct. 20, 2004  (DE) .................. 10 2004 051 023

(51) Int. Cl.
- A61K 38/00 (2006.01)
- A61K 38/12 (2006.01)
- A61K 39/00 (2006.01)
- C07K 5/00 (2006.01)
- C07K 7/00 (2006.01)
- C07K 7/54 (2006.01)
- C07K 9/00 (2006.01)
- C07K 16/00 (2006.01)
- C07K 17/00 (2006.01)

(52) U.S. Cl. .................. 514/9; 514/2; 514/11; 514/15; 530/300; 530/317; 530/328

(58) Field of Classification Search .................. None
See application file for complete search history.

(56) References Cited

U.S. PATENT DOCUMENTS

| | | |
|---|---|---|
| 4,754,018 A | 6/1988 | Tymiak et al. |
| 6,380,156 B1 | 4/2002 | Rinehart et al. |
| 7,056,942 B2 | 6/2006 | Hildesheim et al. |
| 7,368,424 B2 | 5/2008 | Von Nussbaum et al. |
| 7,531,507 B2 | 5/2009 | Von Nussbaum et al. |
| 2005/0075281 A1 | 4/2005 | Von Nussbaum et al. |
| 2005/0272646 A1 | 12/2005 | Koteva et al. |
| 2006/0264358 A1 | 11/2006 | Von Nussbaum et al. |
| 2008/0051424 A1 | 2/2008 | Von Nussbaum et al. |
| 2008/0058251 A1 | 3/2008 | Von Nussbaum et al. |
| 2008/0058253 A1 | 3/2008 | Von Nussbaum et al. |
| 2008/0070884 A1 | 3/2008 | Von Nussbaum et al. |
| 2009/0105119 A1 | 4/2009 | Von Nussbaum et al. |

FOREIGN PATENT DOCUMENTS

| | | |
|---|---|---|
| EP | 196042 | 10/1986 |
| JP | 01132600 | 5/1989 |
| WO | WO-01/05814 | 1/2001 |
| WO | WO-2004/099239 | 11/2004 |
| WO | WO-2006/048156 | 5/2006 |

OTHER PUBLICATIONS

Introduction to Cancer from Merck manual, p. 1. Accessed Mar. 5, 2008.*
Clinical Aspects of Cancer from Merck manual, pp. 1-4. Accessed Mar. 5, 2008.*
Auerbach R, Akhtar N, Lewis RL, Shinners BL, "Angiogenesis assays: PRoblems and pitfalls," Cancer and Metastasis Reviews, 2000, 19: 167-172.*
Gura T, "Systems for Identifying New Drugs are Often Faulty," Science, 1997, 278(7): 1041-1042.*
Jain RK, "Barriers to Drug Delivery in Solid Tumors," Scientific American, Jul. 1994, 58-65.*
Types of disorders from Merck manual, pp. 1-26. Accessed Jul. 29, 2009.*
Types of diseases from Merck manual, pp. 1-27. Accessed Jul. 29, 2009.*
Dementia from Merck manual, pp. 1-17. Accessed Jul. 29, 2009.*
Mattson MP, "Pathways towards and away from Alzheimer's disease," Nature, Aug. 2004, 430: 631-639.*
Baquero, J. Antimicrob. Chemother. (1997 Suppl. A) 39:1-6.
Bonner et al., J. Antibiot. (1988) 41:1745-1751.
Egner et al., Tetrahedron (Oct. 1997) 53(41):14021-14030.
Goldrick, Am. J. Nurs. (2002) 102:17.
Green, Expert Opin. Ther. Targets (2002) 6:1-19.

(Continued)

*Primary Examiner*—Anish Gupta
*Assistant Examiner*—Julie Ha
(74) *Attorney, Agent, or Firm*—Morrison & Foerster LLP

(57) ABSTRACT

Nonadepsipeptides and methods for their preparation and their use for the production of medicaments for the treatment and/or prophylaxis of diseases, in particular bacterial infectious diseases are described.

13 Claims, No Drawings

OTHER PUBLICATIONS

Johnson et al., J. Hosp. Infect. (2001 Suppl. A) 49:3-11.
O'Sullivan et al., J. Antibiot. (1988) 41:1740-1744.
Shoji et al., J. Antibiot. (1988) 41:713-718.
Tymiak et al., J. Org. Chem. (1989) 54:1149-1157.
Alker et al., Tetrahedron (1998) 54:6089-6098.
Anderson and McGregor, J Am Chem Soc (1957) 79:6180-6183.
Bacterial Urinary Tract Infections from the Merck Manual, 8 pages, Accessed Jul. 30, 2007.
Barret et al., Tetrahedron Lett (2001) 42(4):703-705.
Belokon et al., Tetrahedron: Asymmetry (2001) 12:481-485.
Blackburn et al., Drug Metabolism and Disposition (1993) 21(4):573-579.
Bull et al., J Chem Soc Perkin Trans (2001) 1:3281-3287.
Cardillo et al., Synlett (1999) 1727-1730.
Cellulitis from the Merck Manual, 3 pages, Accessed Jul. 30, 2007.
Cohen et al., J Am Chem Soc (2004) 124:2534-2543.
Cystic Fibrosis from the Merck Manual, 7 pages, Accessed Jul. 30, 2007.
Dikler et al., J Mass Spectrometry (1997) 32:1337-1349.
Echner et al., Liebigs Ann Chem (1988) 1095-1098.
English Translation of the International Preliminary Report on Patentability for PCT/EP2005/010856, issued on Apr. 24, 2007, 10 pages.
Harada et al., J of Chrom (2001) 932:75-81.
Hingley, retrieved at http://www.fda.gov/FDAC/features/1998/398_alz.html on Jan. 7, 2009, 6 pages.
International Search Report for PCT/EP2005/010857, mailed on Mar. 27, 2006, 4 pages.
International Search Report for PCT/EP2005/011451, mailed on Feb. 27, 2006, 4 pages.
International Search Report for PCT/EP2007/000645, mailed on May 7, 2007, 4 pages.
International Search Report and Written Opinion for PCT/EP2007/003303, dated Jul. 19, 2007, 16 pages.
International Search Report and Written Opinion for PCT/EP2007/003313, dated Jul. 20, 2007, 10 pages.
IUPAC, Nomenclature and Symbolism for Amino Acids and Peptides, Names and Symbols for Derivatives of Named Peptides, Section 3AA-22 (Recommendations 1983-1992).
Jetten et al., Tetrahedron Lett (1991) 32:6025-6028.
Jiang et al., J Am Chem Soc (2003) 125:1877-1887.
Kalvin et al., J Org Chem (1985) 50(13):2259-2263.
Kato et al., J Antibiot (1988) 41:719-725.
Lee et al., Tetrahedron (2001) 57:2139-2145.
Maki et al., Antimicrob Agents and Chemotherapy (2001) 45(6):1823-1827.
Mattingly et al., J Org Chem (1983) 48:3556-3559.
Merget et al., Organomet Chem (2001) 628:183-194.
Merino et al., Tetrahedron: Asymmetry (1998) 9:629-646.
Murakami et al., Tetrahedron (2000) 56(46):9121-9128.
Neises et al., Org Synth (1985) 63:183-187.
Nomenclature and Symbolism for Amino Acids and Peptides (Recommendations 1983) Biochemical Journal (1984) 219:345-373.
Norman et al., J Org Chem (1998) 63(15):5288-5294.
Oliyai et al., Pharm Res (1995) 12(3):323-328.
Palomo et al., Tetrahedron Lett (2001) 42:8955-8957.
Panico et al., eds., A Guide to IUPAC Nomenclature of Organic Compounds, Blackwell Science Ltd., 1993, pp. 1-190 (Recommendations 1993).
Rane et al., Tetrahedron Lett (1993) 34(20):3201-3204.
Rao et al., Tetrahedron Lett (1991) 32:4393-4396.
Schuhmacher et al., J Pharm Sci (2004) 93:816-830.
Seebach et al., Helv Chim Acta (1996) 79:913-941.
Shemyakin et al., Esperienta (1966) 22(8):535-536.
Tenover, Am J Infect Control (2006) 34:S3-S10.
Thornber, Chem Soc Rev (1979) 8(4):563-580.
Translation of the International Preliminary Report on Patentability for PCT/EP2005/011451, mailed Jul. 12, 2007, 8 pages.
Translation of the International Preliminary Report on Patentability for PCT/EP2005/010857, Apr. 24, 2007, 11 pages.
Translation of the International Preliminary Report on Patentability for PCT/EP2007/000645, issued Sep. 9, 2008, 9 pages.
Ulhaq et al., Bioorg Med Chem (1999) 7(9):1787-1796.
Van Hof et al., Biol Chem (2001) 382:597-619.
Vippagunta et al., Adv Drug Delivery Rev (2001) 48:3-26.
Translation of the International Preliminary Report on Patentability, issued Apr. 24, 2007, 5 pages.

* cited by examiner

DEOXONADEPSIPEPTIDES

CROSS-REFERENCE TO RELATED APPLICATIONS

This application is a continuation of pending international application PCT/EP2005/010858, filed Oct. 8, 2005, designating US, which claims priority from German patent application DE 10 2004 051 023.7, filed Oct. 20, 2004. The contents of the above-referenced applications are incorporated herein by this reference in their entirety.

BACKGROUND OF THE INVENTION

The invention relates to nonadepsipeptides and methods for their preparation, as well as to their use for the production of medicaments for the treatment and/or prophylaxis of diseases, in particular bacterial infectious diseases.

The bacterial cell wall is synthesized by a number of enzymes (cell wall biosynthesis) and is essential for the survival and reproduction of microorganisms. The structure of this macromolecule, as well as the proteins involved in its synthesis, are highly conserved within the bacteria. On account of its essential nature and uniformity, cell wall biosynthesis is an ideal point of attack for novel antibiotics (D. W. Green, The bacterial cell wall as a source of antibacterial targets, *Expert Opin. Ther. Targets*, 2002, 6, 1-19).

Vancomycin and penicillins are inhibitors of the bacterial cell wall biosynthesis and represent successful examples of the antibiotic potency of this principle of action. They have been employed for several decades clinically for the treatment of bacterial infections, especially with Gram-positive pathogens. Owing to the growing occurrence of resistant microorganisms, e.g. methicillin-resistant staphylococci, penicillin-resistant pneumococci and vancomycin-resistant enterococci (F. Baquero, Gram-positive resistance: challenge for the development of new antibiotics, *J. Antimicrob. Chemother.*, 1997, 39, Suppl A: 1-6; A. P. Johnson, D. M. Livermore, G. S. Tillotson, Antimicrobial susceptibility of Gram-positive bacteria: what's current, what's anticipated?, *J. Hosp. Infect.*, 2001, (49), Suppl A: 3-11) and recently also for the first time vancomycin-resistant staphylococci (B. Goldrick, First reported case of VRSA in the United States, *Am. J. Nurs.*, 2002, 102, 17), these substances are increasingly losing their therapeutic efficacy.

The present invention describes a novel class of cell wall biosynthesis inhibitors without cross resistances to known classes of antibiotics.

The natural product lysobactin and some derivatives are described as having antibacterial activity in U.S. Pat. No. 4,754,018. The isolation and antibacterial activity of lysobactin is also described in EP-A-196 042 and JP 01132600. WO04/099239 describes derivatives of lysobactin having antibacterial activity.

The antibacterial activity of lysobactin and katanosin A is furthermore described in O'Sullivan, J. et al., *J. Antibiot.* 1988, 41, 1740-1744, Bonner, D. P. et al., *J. Antibiot.* 1988, 41, 1745-1751, Shoji, J. et al., *J. Antibiot.* 1988, 41, 713-718 and Tymiak, A. A. et al., *J. Org. Chem.* 1989, 54, 1149-1157.

SUMMARY OF THE INVENTION

It is one object of the present invention to provide alternative compounds having comparable or improved antibacterial activity, better solubility and better tolerability for the treatment of bacterial diseases in humans and animals.

The invention relates to compounds of formula

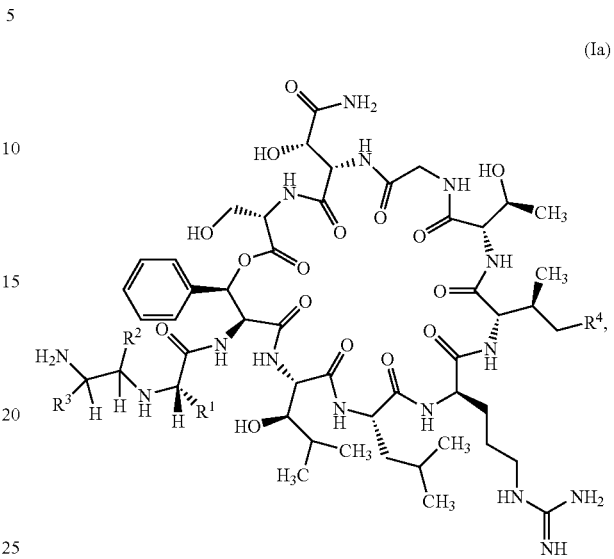

(Ia)

in which

R$^1$ represents C$_1$-C$_2$-alkyl, whereby C$_1$-C$_2$-alkyl is substituted with a substituent selected from the group consisting of trimethylsilyl, alkoxycarbonyl, C$_3$-C$_6$-cycloalkyl, alkoxy-substituted phenyl, 2-pyridyl and 3-pyridyl, or represents C$_4$-C$_8$-alkyl, R$^2$ represents hydrogen or C$_1$-C$_4$-alkyl, R$^3$ represents C$_1$-C$_2$-alkyl, whereby C$_1$-C$_2$-alkyl is substituted with a substituent trimethylsilyl, or represents C$_4$-C$_6$-alkyl, R$^4$ represents hydrogen or methyl, and their salts, their solvates and the solvates of their salts.

Compounds of the invention are the compounds of formula (I) and (Ia) and their salts, solvates, solvates of the salts and prodrugs, the compounds of the formulae mentioned below encompassed by formula (I) and (Ia) and their salts, solvates, solvates of the salts and prodrugs, and the compounds mentioned below as exemplary embodiments, encompassed by formula (I) and (Ia), and their salts, solvates, solvates of the salts and prodrugs, insofar as the compounds subsequently mentioned, encompassed by formula (I) and (Ia), are not already salts, solvates, solvates of the salts and prodrugs.

Depending on their structure, the compounds of the invention can exist in stereoisomeric forms (enantiomers, diastereomers). The invention therefore relates to the enantiomers or diastereomers and their respective mixtures. The stereoisomerically uniform constituents can be isolated in a known manner from such mixtures of enantiomers and/or diastereomers.

Where the compounds of the invention can occur in tautomeric forms, the present invention comprises all tautomeric forms.

Salts preferred for the purpose of the present invention are physiologically acceptable salts of the compounds of the invention. However, also included are salts which are themselves not suitable for pharmaceutical applications but can be used, for example, for the isolation or purification of the compounds of the invention.

Physiologically acceptable salts of the compounds of the invention include acid addition salts of mineral acids, carboxylic acids and sulfonic acids, e.g. salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, trifluoroacetic acid, propionic acid, lactic acid, tartaric acid, malic acid, citric acid, fumaric acid, maleic acid and benzoic acid.

Physiologically acceptable salts of the compounds of the invention also include salts of usual bases, such as, by way of example and preferably, alkali metal salts (e.g. sodium and potassium salts), alkaline earth metal salts (e.g. calcium and magnesium salts) and ammonium salts, derived from ammonia or organic amines having 1 to 16 C atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates for the purpose of the invention refer to those forms of the compounds of the invention which form a complex in the solid or liquid state by coordination with solvent molecules. Hydrates are a special form of solvates in which coordination takes place with water.

For the purpose of the present invention, the substituents have the following meaning, unless specified otherwise:

Alkyl per se and "alk" and "alkyl" in alkoxy and alkoxycarbonyl represents a linear or branched alkyl radical normally having 1 to 6, preferably 1 to 4, particularly preferably 1 to 3 carbon atoms, by way of example and preferably methyl, ethyl, n-propyl, isopropyl, tert-butyl, 2,2-dimethylprop-1-yl, n-pentyl and n-hexyl.

Alkoxy by way of example and preferably represents methoxy, ethoxy, n-propoxy, isopropoxy, tert-butoxy, n-pentoxy and n-hexoxy.

Alkoxycarbonyl represents, by way of example and preferably, methoxycarbonyl, ethoxycarbonyl, n-propoxycarbonyl, isopropoxycarbonyl, tert-butoxycarbonyl, n-pentoxycarbonyl and n-hexoxycarbonyl.

Cycloalkyl represents a cycloalkyl group normally having 3 to 6 carbon atoms, by way of example and preferably cyclopropyl, cyclobutyl, cyclopentyl and cyclohexyl.

In the formulae of the groups, the end of the line, besides which in each case there is an *, does not represent a carbon atom or a $CH_2$ group, but is a constituent of the bond to the nitrogen atom, to which the group of the formula is attached.

Preferred compounds for the purpose of the present invention are those of formula

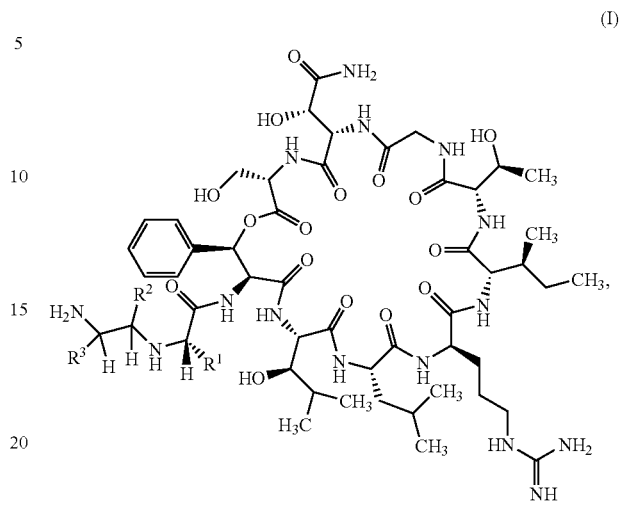

(I)

in which
R$^1$ represents $C_1$-$C_2$-alkyl,
whereby $C_1$-$C_2$-alkyl is substituted with a substituent selected from the group consisting of trimethylsilyl, alkoxycarbonyl, $C_3$-$C_6$-cycloalkyl, alkoxy-substituted phenyl, 2-pyridyl and 3-pyridyl,
or
represents $C_4$-$C_8$-alkyl,
R$^2$ represents hydrogen or $C_1$-$C_4$-alkyl,
R$^3$ represents $C_1$-$C_2$-alkyl,
whereby $C_1$-$C_2$-alkyl is substituted with a substituent trimethylsilyl,
or
represents $C_4$-$C_6$-alkyl,
and their salts, their solvates and the solvates of their salts.

Preferred compounds are also those of formula (I), in which
R$^1$ represents $C_1$-$C_2$-alkyl
whereby $C_1$-$C_2$-alkyl is substituted with a substituent trimethylsilyl,
or
represents $C_4$-$C_6$-alkyl,
R$^2$ represents hydrogen or methyl,
R$^3$ represents $C_1$-$C_2$-alkyl,
whereby $C_1$-$C_2$-alkyl is substituted with a substituent trimethylsilyl,
or
represents $C_4$-$C_6$-alkyl,
and their salts, their solvates and the solvates of their salts.

Particularly preferred compounds are those of the formula (I), in which
R$^1$ represents trimethylsilylmethyl or 2,2-dimethylprop-1-yl,
R$^2$ represents hydrogen,
R$^3$ represents trimethylsilylmethyl or 2,2-dimethylprop-1-yl,
and their salts, their solvates and the solvates of their salts.

Preferred compounds are also those of formula (I), in which R$^1$ represents 2,2-dimethylprop-1-yl.

Preferred compounds are also those of formula (I), in which R$^2$ represents hydrogen.

Preferred compounds are also those of formula (I), in which R$^3$ represents 2,2-dimethylprop-1-yl.

The radical definitions indicated in detail in the respective combinations or preferred combinations of radicals are arbitrarily also replaced by radical definitions of a different combination independently of the respective combinations of the radicals indicated.

Combinations of two or more of the abovementioned preferred ranges are also very particularly preferred.

The invention furthermore relates to a method for preparing the compounds of the formulae (Ia), whereby the compound of formula

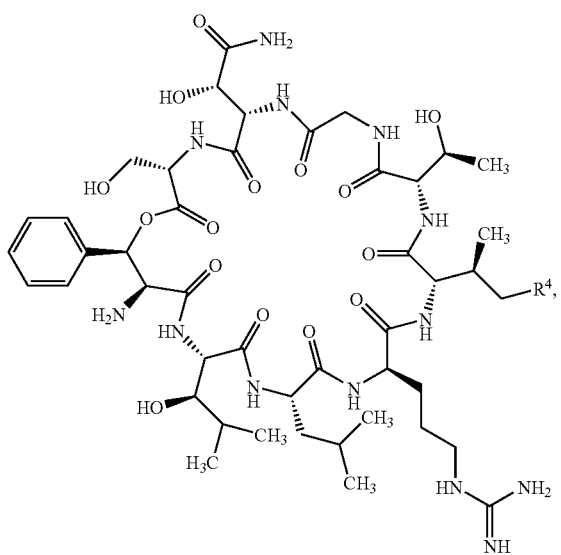

(II)

in which

R$^4$ has the meaning indicated above, is reacted with compounds of formula

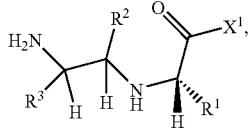

(III)

in which

R$^1$, R$^2$ and R$^3$ have the meaning indicated above, and

X$^1$ represents halogen, preferably bromine, chlorine or fluorine, or hydroxy.

If X$^1$ is halogen, the reaction generally takes place in inert solvents, where appropriate in the presence of a base, preferably in a temperature range from −30° C. to 50° C. under atmospheric pressure.

Inert solvents are, for example, tetrahydrofuran, methylene chloride, pyridine, dioxane or dimethylformamide; pyridine or dimethylformamide are preferred.

Preferred inert solvents are tetrahydrofuran or methylene chloride.

Bases are, for example, triethylamine, diisopropylethylamine or N-methylmorpholine; diisopropylethylamine is preferred.

If X$^1$ is hydroxy, the reaction generally takes place in inert solvents, in the presence of a dehydrating reagent, where appropriate in the presence of a base, preferably in a temperature range from −30° C. to 50° C. under atmospheric pressure.

Inert solvents are, for example, halohydrocarbons such as dichloromethane or trichloromethane, hydrocarbons such as benzene, nitromethane, dioxane, dimethylformamide or acetonitrile. It is likewise possible to employ mixtures of the solvents. Dichloromethane or dimethylformamide are particularly preferred.

Suitable dehydrating reagents hereby are, for example, carbodiimides such as, for example, N,N'-diethyl-, N'-dipropyl-, N,N'-diisopropyl-, N,N'-dicyclohexylcarbodiimide, N-(3-dimethylaminoisopropyl)-N'-ethylcarbodiimide hydrochloride (EDC), N-cyclohexylcarbodiimide-N'-propyloxymethylpolystyrene (PS carbodiimide) or carbonyl compounds such as carbonyldiimidazole, or 1,2-oxazolium compounds such as 2-ethyl-5-phenyl-1,2-oxazolium 3-sulfate or 2-tert-butyl-5-methylisoxazolium perchlorate, or acylamino compounds such as 2-ethoxy-1-ethoxycarbonyl-1,2-dihydroquinoline, or propanephosphonic anhydride, or isobutyl chloroformate, or bis-(2-oxo-3-oxazolidinyl)phosphoryl chloride or benzotriazolyloxytri-(dimethylamino)phosphonium hexafluorophosphate, or O-(benzotriazol-1-yl)-N,N,N', N'-tetramethyluronium hexafluorophosphate (HBTU), 2-(2-oxo-1-(2H)-pyridyl)-1,1,3,3-tetramethyluronium tetrafluoroborate (TPTU) or O-(7-azabenzotriazol-1-yl)-N, N,N',N'-tetramethyluronium hexafluorophosphate (HATU), or 1-hydroxybenzotriazole (HOBt), or benzotriazol-1-yloxy-tris(dimethylamino)phosphonium hexafluorophosphate (BOP), or N-hydroxysuccinimide, or mixtures of these, with bases.

Bases are, for example, alkali metal carbonates, such as, for example, sodium or potassium carbonate, or hydrogencarbonate, or organic bases such as trialkylamines, e.g. triethylamine, N-methylmorpholine, N-methylpiperidine, 4-dimethylaminopyridine or diisopropylethylamine.

Preferably, the condensation is carried out using HATU or using EDC in the presence of HOBt.

The compounds of formula (III) optionally bear protecting groups, so that in these cases the reaction of the compound of formula (II) with compounds of formula (III) is followed by the removal of the protecting groups using, for example, trifluoroacetic acid or by hydrogenolysis according to the methods known to the person skilled in the art.

The compound of formula (II) can be synthesized from lysobactin (Example 1A) by double Edman degradation, as described in the experimental section under Example 2A to 5A.

The compounds of formula (III) are known or can be synthesized from the corresponding starting materials by known processes, for example by the following synthesis scheme:

Synthesis scheme 1:
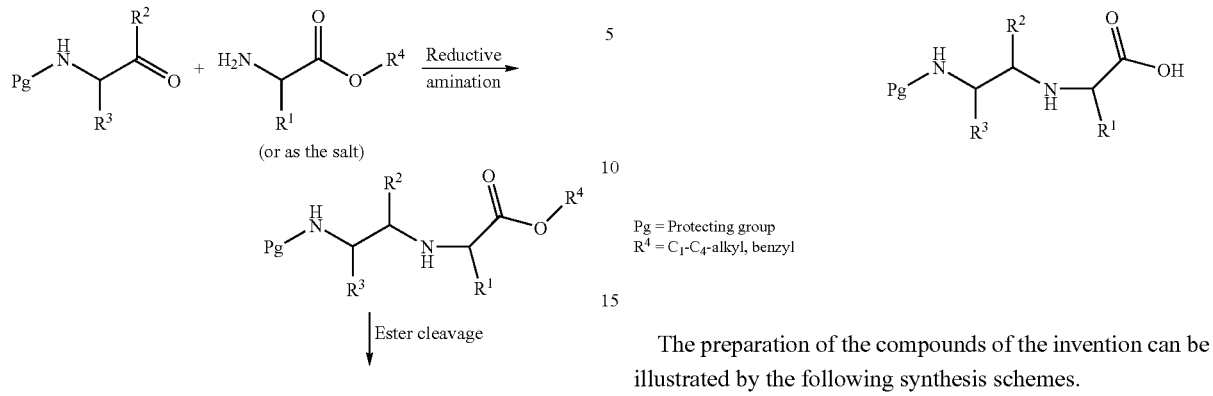
Pg = Protecting group
R⁴ = $C_1$-$C_4$-alkyl, benzyl
The preparation of the compounds of the invention can be illustrated by the following synthesis schemes.
Synthesis scheme 2:
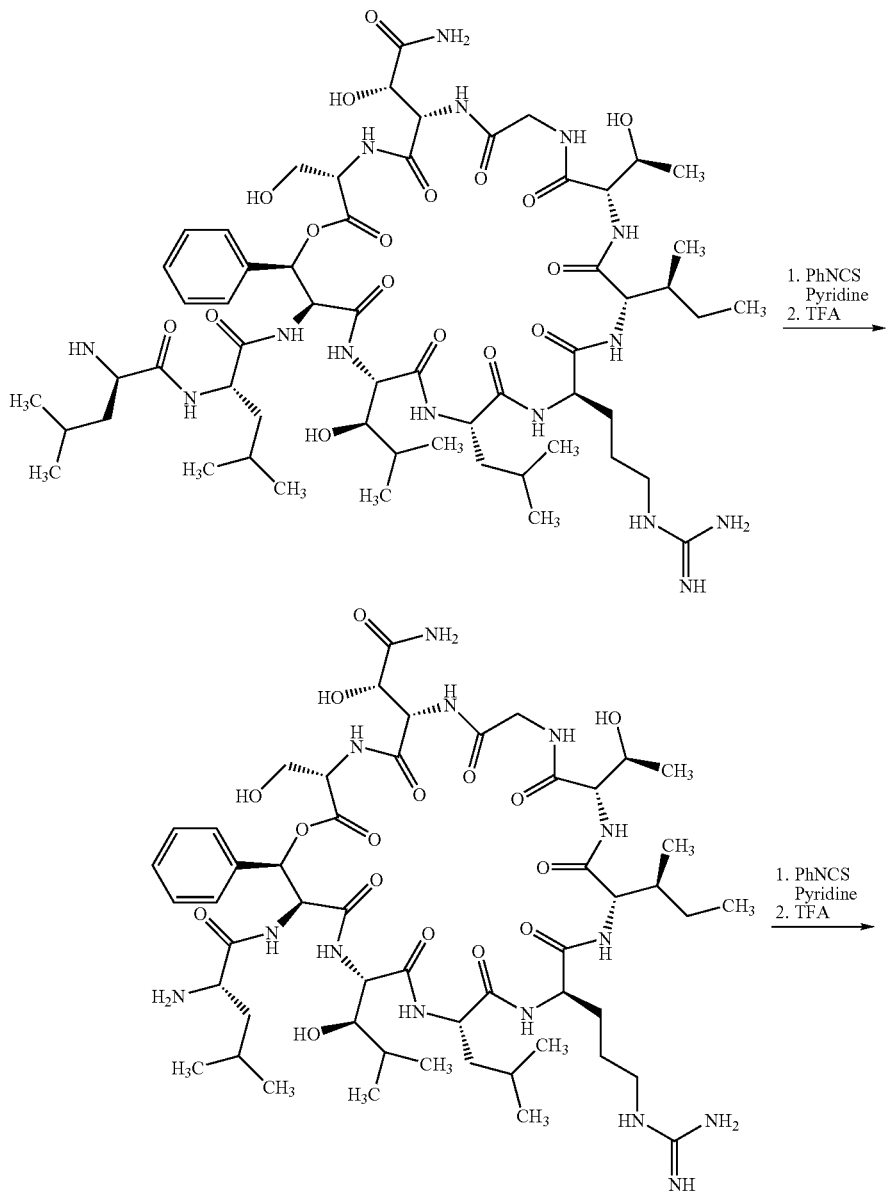

-continued
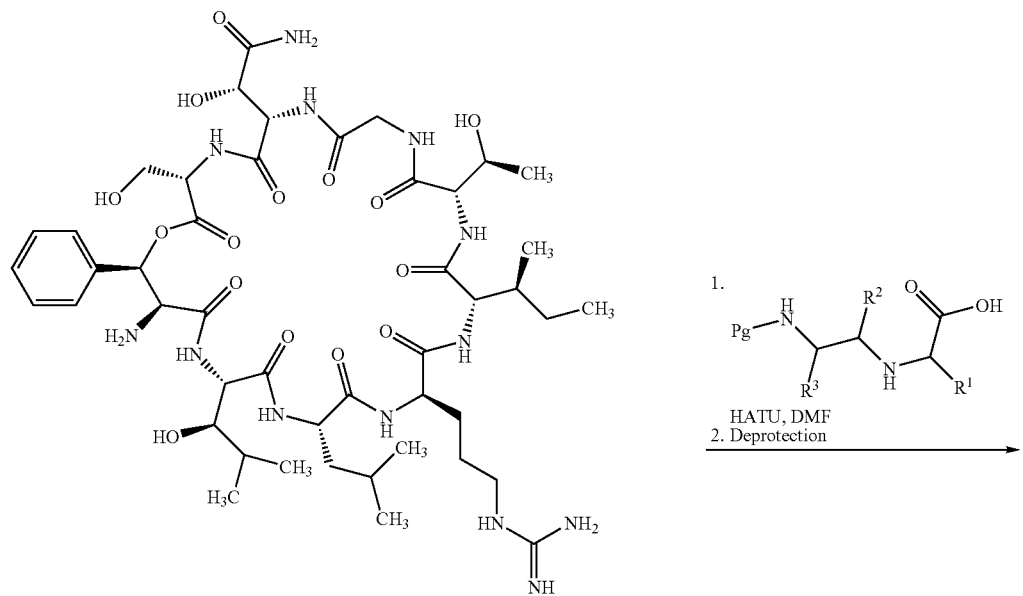
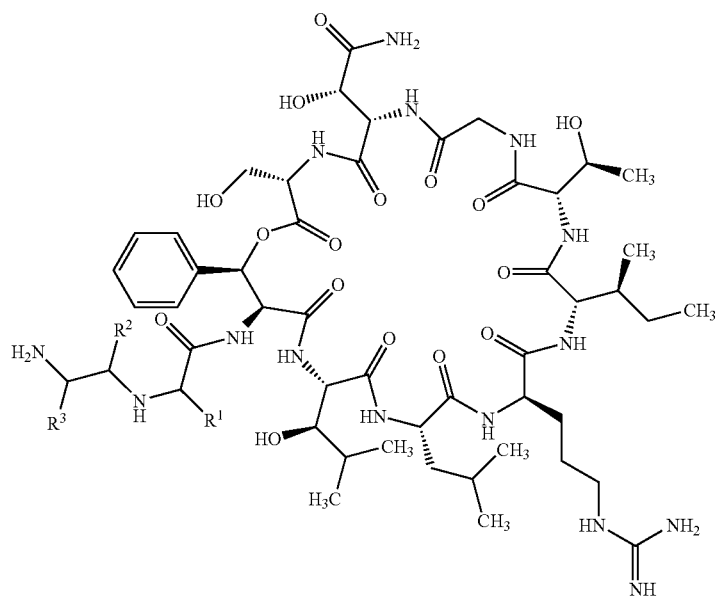

Synthesis scheme 3:

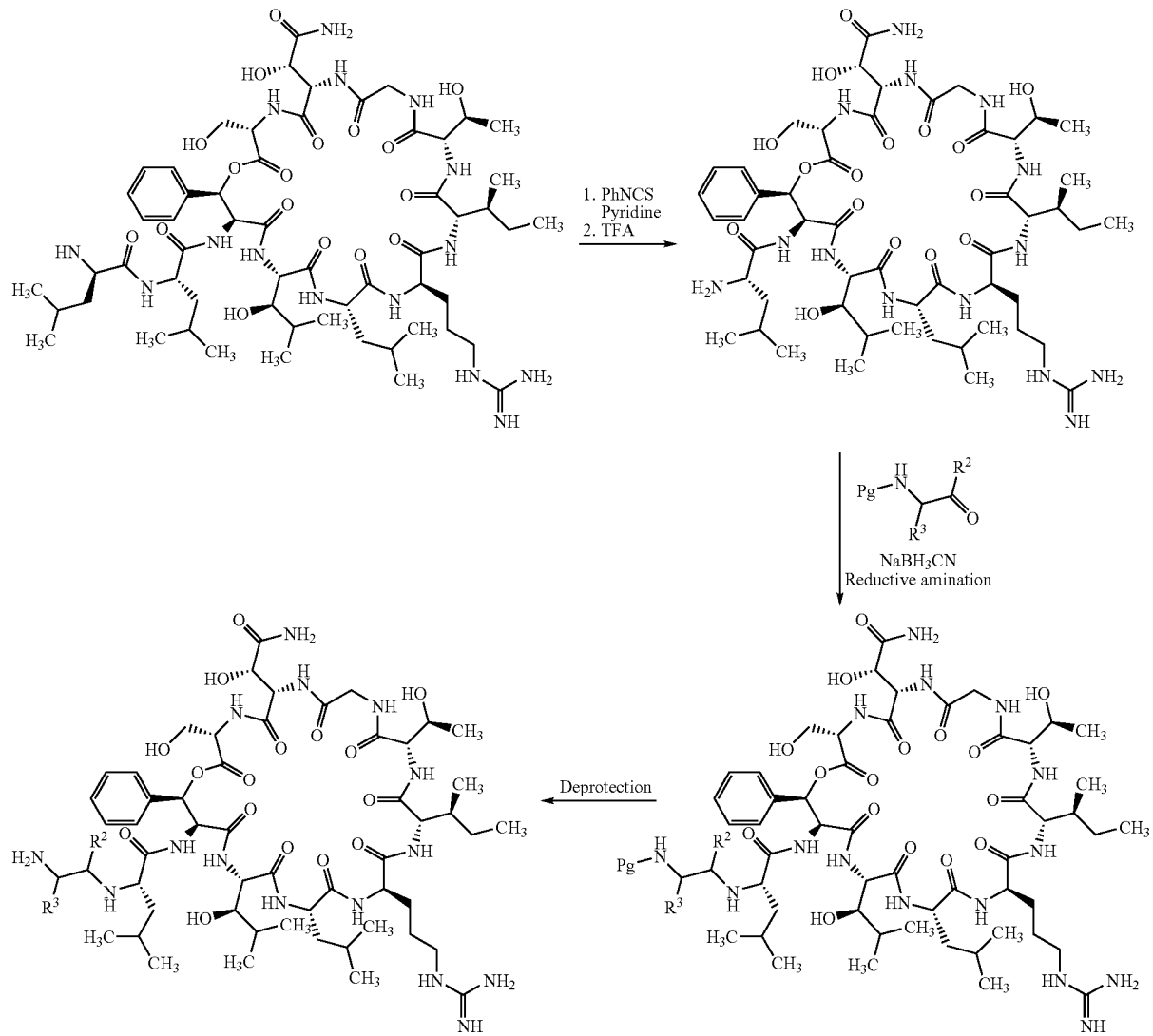

The compounds of the invention show a valuable spectrum of pharmacological activity which could not have been predicted. They show an antibacterial activity.

They are therefore suitable for use as medicaments for the treatment and/or prophylaxis of diseases in humans and animals.

The compounds of the invention are distinguished by a better solubility compared to lysobactin.

The nonadepsipeptides described act as inhibitors of the bacterial cell wall biosynthesis.

The preparations of the invention are particularly effective against bacteria and bacteria-like microorganisms. They are therefore particularly suitable for the prophylaxis and chemotherapy of local and systemic infections caused by these pathogens in human and veterinary medicine.

In principle, the preparations of the invention can be used against all bacteria and bacteria-like microorganisms which possess a bacterial cell wall (Murein sacculus) or the corresponding enzyme systems, for example by the following pathogens or by mixtures of the following pathogens:

Gram-negative cocci (*Neisseria gonorrhoeae*) as well as Gram-negative rods such as Enterobacteriaceae, e.g. *Escherichia coli, Haemophilus influenzae, Pseudomonas, Klebsiella, Citrobacter* (*C. freundii, C. divernis*), *Salmonella* and *Shigella*; furthermore *Enterobacter* (*E. aerogenes, E. agglomerans*), *Hafnia, Serratia* (*S. marcescens*), *Providencia, Yersinia*, as well as the genus *Acinetobacter, Branhamella* and *Chlamydia*. Moreover, the antibacterial spectrum includes strictly anaerobic bacteria such as, for example, *Bacteroides fragilis*, representatives of the genus *Peptococcus, Peptostreptococcus* as well as the genus *Clostridium*; furthermore *Mycobacteria*, e.g. *M. tuberculosus*. The compounds of the invention show a particularly pronounced effect on Gram-positive cocci, e.g. staphylococci (*S. aureus, S. epidermidis, S. haemolyticus, S. carnosus*), enterococci (*E. faecalis, E. faecium*) and streptococci (*S. agalactiae, S. pneumoniae, S. pyogenes*).

The above list of pathogens is to be interpreted only by way of example and in no way as restrictive. Diseases which may be mentioned which are caused by the pathogens mentioned or mixed infections and can be prevented, ameliorated or cured by the preparations of the invention are, for example:

Infectious diseases in humans such as, for example, uncomplicated and complicated urinary tract infections, uncomplicated skin and superficial infections, complicated skin and soft tissue infections, pneumonia acquired in hospital and as an outpatient, nosocomial pneumonia, acute exacerbations and secondary bacterial infections of chronic bronchitis, acute otitis media, acute sinusitis, streptococcal pharyngitis, bacterial meningitis, uncomplicated gonococcal and non-gonococcal urethritis/cervicitis, acute prostatitis, endocarditis, uncomplicated and complicated intra-abdominal infections, gynaecological infections, pelvic inflammatory disease, bacterial vaginosis, acute and chronic osteomyelitis, acute bacterial arthritis, empirical therapy in febrile neutropenic patients, furthermore bacteraemias, MRSA infections, acute infectious diarrhoea, *Helicobacter pylori* infections, postoperative infections, odontogenic infections, opthalmological infections, postoperative infections (including periproctal abscess, wound infections, biliary infections, mastitis and acute appendicitis), cystic fibrosis and bronchiectasis.

Apart from in humans, bacterial infections can also be treated in other species. Examples which may be mentioned are:

Pigs: diarrhoea, enterotoxaemia, sepsis, dysentery, salmonellosis, metritis-mastitis-agalactiae syndrome, mastitis;

Ruminants (cattle, sheep, goats): diarrhoea, sepsis, bronchopneumonia, salmonellosis, pasteurellosis, genital infections;

Horses: bronchopneumonia, joint-ill, puerperal and post-puerperal infections, salmonellosis;

Dogs and cats: bronchopneumonia, diarrhoea, dermatitis, otitis, urinary tract infections, prostatitis;

Poultry (chickens, turkeys, quails, pigeons, ornamental birds and others): *E. Coli* infections, chronic respiratory diseases, salmonellosis, pasteurellosis, psittacosis.

It is likewise possible to treat bacterial diseases in the raising and keeping of productive and ornamental fish, the antibacterial spectrum thereby extending beyond the previously mentioned pathogens to further pathogens such as, for example, *Pasteurella, Brucella, Campylobacter, Listeria, Erysipelothris, Corynebacteria, Borellia, Treponema, Nocardia, Rikettsia, Yersinia.*

The present invention further relates to the use of the compounds of the invention for the treatment and/or prophylaxis of diseases, in particular of bacterial infectious diseases.

The present invention further relates to the use of the compounds of the invention for the treatment and/or prophylaxis of diseases, in particular the aforementioned diseases.

The present invention further relates to the use of the compounds of the invention for the production of a medicament for the treatment and/or prophylaxis of diseases, in particular the aforementioned diseases.

The compounds of the invention are preferably used for the production of medicaments which are suitable for the prophylaxis and/or treatment of bacterial diseases.

The present invention further relates to a method for the treatment and/or prophylaxis of diseases, in particular the aforementioned diseases, using an antibacterially active amount of the compounds of the invention.

The present invention further relates to medicaments, comprising at least one compound of the invention and at least one or more further active compounds, in particular for the treatment and/or prophylaxis of the aforementioned diseases. Preferred active compounds for combination are antibacterially active compounds which have a different spectrum of activity, in particular a supplementary spectrum of activity, and/or are synergistic for the compounds of the invention.

The compounds of the invention can act systemically and/or locally. For this purpose, they can be administered in a suitable way, such as, for example, orally, parenterally, pulmonarily, nasally, sublingually, lingually, buccally, rectally, dermally, transdermally, conjunctivally, otically or as an implant or stent.

The compounds of the invention can be administered in administration forms suitable for these administration routes.

Suitable for oral administration are administration forms which function according to the prior art and deliver the compounds of the invention rapidly and/or in a modified fashion and which contain the compounds of the invention in crystalline and/or amorphized and/or dissolved form, such as, for example, tablets (uncoated or coated tablets, for example having enteric coatings or coatings which dissolve with a delay or are insoluble and which control the release of the compound of the invention), tablets or films/wafers which disintegrate rapidly in the oral cavity, films/lyophilizates, capsules (for example hard or soft gelatine capsules), sugar-coated tablets, granules, pellets, powders, emulsions, suspensions, aerosols or solutions.

Parenteral administration can take place with avoidance of an absorption step (e.g. intravenous, intraarterial, intracardial, intraspinal or intralumbar) or with inclusion of an absorption (e.g. intramuscular, subcutaneous, intracutaneous, percutaneous or intraperitoneal). Administration forms suitable for parenteral administration are, inter alia, preparations for injection and infusion in the form of solutions, suspensions, emulsions, lyophilizates, or sterile powders.

Suitable for the other administration routes are, for example, pharmaceutical forms for inhalation (inter alia powder inhalers, nebulizers), nasal drops, solutions, sprays; tablets, films/wafers or capsules for lingual, sublingual or buccal administration, suppositories, preparations for ears or eyes, vaginal capsules, aqueous suspensions (lotions, shaking mixtures), lipophilic suspensions, ointments, creams, transdermal therapeutic systems (such as, for example, patches), milk, pastes, foams, dusting powder, implants or stents.

The compounds of the invention can be converted into the stated administration forms. This can take place in a manner known per se by mixing with inert, non-toxic, pharmaceutically acceptable excipients. These excipients include, inter alia, carriers (for example microcrystalline cellulose, lactose, mannitol), solvents (e.g. liquid polyethylene glycols), emulsifiers and dispersants or wetting agents (for example sodium dodecyl sulfate, polyoxysorbitan oleate), binders (for example polyvinylpyrrolidone), synthetic and natural polymers (for example albumin), stabilizers (e.g. antioxidants such as, for example, ascorbic acid), colors (e.g. inorganic pigments such as, for example, iron oxides) and taste and/or odor corrigents.

The present invention furthermore relates to medicaments which comprise at least one compound of the invention, usually together with one or more inert, non-toxic, pharmaceutically acceptable excipients, and their use for the aforementioned purposes.

In general, it has proved advantageous on intravenous administration to administer amounts of about 0.001 to 100 mg/kg, preferably about 0.1 to 10 mg/kg of body weight to achieve effective results, and on oral administration the dosage is about 0.01 to 50 mg/kg, preferably 0.5 to 10 mg/kg, of body weight.

It may nevertheless be necessary where appropriate to deviate from the stated amounts, in particular as a function of body weight, route of administration, individual behaviour towards the active compound, type of preparation and time or interval over which administration takes place. Thus, in some cases it may be sufficient to make do with less than the aforementioned minimum amount, while in other cases the state upper limit must be exceeded. In the case of the administration of larger amounts, it can be advisable to divide these into a number of individual doses over the course of the day.

The percentages in the following tests are, unless indicated otherwise, percentages by weight; yields in the examples are molar percentages; parts are parts by weight. Solvent ratios, dilution ratios and concentrations of liquid/liquid solutions are in each case based on volume.

DETAILED DESCRIPTION OF PREFERRED EMBODIMENTS

A. Examples
Abbreviations

| Area | (Peak) area |
|---|---|
| BHI | Brain heart infusion |
| Boc | tert-butyloxycarbonyl |
| br. | broad signal (in NMR spectra) |
| calc. | calculated |
| conc. | concentrated |
| d | doublet (in NMR spectra) |
| DCI | direct chemical ionization (in MS) |
| DCM | dichloromethane |
| DIEA | N,N-diisopropylethylamine |
| DMF | N,N-dimethylformamide |
| DMSO | dimethylsulfoxide |
| EA | ethyl acetate (acetic acid ethyl ester) |
| EDC | 1-ethyl-3-(3-dimethylaminopropyl)carbodiimide (also EDCI) |
| EDCxHCl | 1-ethyl-3-(3-dimethylaminopropyl)carbodiimide hydrochloride |
| EI | electron impact ionization (in MS) |
| ESI | electrospray ionization (in MS) |
| Ex. | Example |
| fnd. | found |
| Gen. | General |
| h | hour |
| HATU | O-(7-azabenzotriazol-1-yl)-N,N,N',N'-tetramethyluronium hexafluorophosphate |
| HOBt | 1-hydroxybenzotriazole |
| HPLC | high-pressure or high-performance liquid chromatography |
| HR | high resolution |
| i. V. | in vacuo |
| LC-MS | liquid chromatography-coupled mass spectroscopy |
| LDA | lithium diisopropylamide |
| m | middle (in UV and IR spectra) |
| m | multiplet (in NMR spectra) |
| MALDI | matrix-assisted laser desorption/ionization |
| MIC | minimum inhibitory concentration |
| min | minute/minutes |
| Mp. | melting point |
| MRSA | methicillin-resistant Staphylococcus aureus |
| MS | mass spectroscopy |
| NCCLS | National Committee for Clinical Laboratory Standards |
| neg. | negative |
| NMM | N-methylmorpholine |
| NMR | nuclear magnetic resonance spectroscopy |
| of th. | of theory |
| p.a. | per analysi |
| Pd-C | palladium on carbon |
| perc. | per cent |
| pos. | positive |
| quant. | quantitative |
| RP-HPLC | reverse phase HPLC |
| RT | room temperature |
| $R_f$ | retention time (in HPLC) |
| s | strong (in UV and IR spectra) |
| s | singlet (in NMR spectra) |
| satd. | saturated |
| TBTU | O-(benzotriazol-1-yl)-N,N,N',N'-tetramethyluronium tetrafluoroborate |

-continued

| Area | (Peak) area |
|---|---|
| TCTU | O-(1H-6-chlorobenzotriazol-1-yl)-1,1,3,3-tetramethyluronium tetrafluoroborate |
| TFA | trifluoroacetic acid |
| TFE | 2,2,2-trifluoroethanol |
| THF | tetrahydrofuran |
| TLC | thin-layer chromatography |
| TOF | time of flight |
| UV | ultraviolet |
| vis | visible |
| VRSA | vancomycin-resistant Staphylococcus aureus |
| w | weak (in UV and IR spectra) |
| Z, Cbz | benzyloxycarbonyl |

Literature

For the nomenclature of the peptides and cyclodepsipeptides cf.:

1. A Guide to IUPAC Nomenclature of Organic Compounds (Recommendations 1993), 1993, Blackwell Scientific publications.
2. Nomenclature and symbolism for amino acids and peptides. Recommendations 1983. IUPAC-IUB Joint Commission on Biochemical Nomenclature, UK. *Biochemical Journal* 1984, 219, 345-373. And cited literature.

General Methods LC-MS, HR-MS, HPLC and Gel Chromatography

Method 1 (HPLC): instrument: HP 1100 with DAD (G1315A) and autosampler (G1329A), auto-sampler therm (G1330A, 5° C.), degasser (G1322A) and binary pump (G1312A); precolumn: Waters Symmetry C-18, 10×2.1 mm, 3.5 µm; analytical column: Waters Symmetry C-18, 50×2.1 mm, 3.5 µm; column oven: 45° C.; eluent A: water/0.05% trifluoroacetic acid; eluent B: acetonitrile/0.05% trifluoroacetic acid; flow: 0.4 ml/min.; gradient 0-100% B in 9 min, after this 3 min at 100% B, after this regeneration of the column.

Method 2 (LC-MS): instrument: Micromass LCT; ionization: ESI positive/negative; HP1100 with DAD and autosampler; oven 40° C.; column: Waters Symmetry C-18, 50×2.1 mm, 3.5 µm; eluent A: 0.1% formic acid/acetonitrile, eluent B: 0.1% formic acid/water; flow: 0.5 ml/min.; gradient: 0-1 min 0% A, 1-6 min 90% A, 6-8 min 100% A, 8-10 min 100% A, 10-150% A.

Method 3 (HPLC): instrument: Gilson Abimed HPLC; UV detector 254 nm; binary pump system; column: Nucleosil RP-18, 7 µm; 250×50 mm; flow: 30 ml/min; eluent A: water/0.1% trifluoroacetic acid, eluent B: acetonitrile/0.1% trifluoroacetic acid; gradient: 0-40 min 20-25% B, 40-60 min 25% B, 60-110 min 25-50% B, 110-120 min 50% B, 120-130 min 50-100% B, 130-160 min 100% B, subsequent regeneration of the chromatography column.

Method 4 (HPLC): instrument: Gilson Abimed HPLC; UV detector 254 nm; binary pump system; column: Nucleosil RP-18, 7 µm; 250×50 mm; flow: 40 ml/min; eluent A: water/0.05% trifluoroacetic acid, eluent B: acetonitrile/0.05% trifluoroacetic acid; gradient: 0-105 min 20-25% B, 105-111 min 25% B, 111-131 min 25-27% B, 131-157 min 27-35% B, 157-192 min 35-40% B, 192-207 min 40-45% B, subsequent regeneration of the chromatography column.

Method 5 (HPLC): instrument: Gilson Abimed HPLC; UV detector 254 nm; binary pump system; column: Nucleosil RP-18, 7 µm; 250×50 mm; flow: 40 ml/min; eluent A: water/0.05% trifluoroacetic acid, eluent B: acetonitrile/0.05% trifluoroacetic acid; gradient: 0-40 min 20-25% B, 40-105 min 25% B, 105-130 min 25-27% B, 130-170 min 27-40% B, 170-190 min 40% B, 190-210 min 40-45% B, subsequent regeneration of the chromatography column.

Method 6 (gel chromatography on Sephadex LH-20): Gel chromatography is carried out without pressure on Sephadex LH-20 (Pharmacia). Fractionation (fraction collector ISCO Foxy 200) is carried out according to UV activity (UV detector for 254 nm, Knauer). Column dimensions: 32×7 cm (1000-100 µmol scale); 30×4 cm (100-10 µmol scale); 25×2 cm (10-1 µmol scale).

Method 7 (preparative HPLC; Symmetry): instrument: Gilson Abimed HPLC; UV detector 210 nm; binary pump system; column: SymmetryPrep™ $C_{18}$, Waters, 7 µm; 300×19 mm; flow: 20 ml/min; eluent A: 0.05% trifluoroacetic acid in water, eluent B: 0.05% trifluoroacetic acid in acetonitrile; gradient: 0-3 min 10% B, 3-30 min gradient ramp 10-90% B, 30-38 min 90% B, 38-45 min 10% B.

Method 8 (preparative HPLC; Symmetry; TFA): instrument: Gilson Abimed HPLC; UV detector 210 nm; binary pump system; column: SymmetryPrep™ $C_{18}$, Waters, 7 µm; 300×19 mm; flow: 7 ml/min; eluent A: water/0.1-0.25% trifluoroacetic acid, eluent B: acetonitrile; gradient: 0-8 min 5% B, 8-40 min 5-60% B, 40-60 min 60% B, 60-75 min 60-100% B, 75-80 min 100% B, subsequent regeneration of the chromatography column.

Method 9 (preparative HPLC; Kromasil, acetic acid): instrument: Gilson Abimed HPLC; UV detector 210 nm; binary pump system; column: Kromasil-100A $C_{18}$, 5 µm; 250×20 mm; flow: 25 ml/min; eluent A: water/0.25-0.5% acetic acid, eluent B: acetonitrile; gradient: 0-3 min 5% B, 3-30 min 5-100% B, 30-38 min 100% B, subsequent regeneration of the chromatography column.

Method 10 (preparative HPLC; Symmetry; sensitive for final products): instrument: Gilson Abimed HPLC; UV detector 210 nm; binary pump system; column: SymmetryPrep™ $C_{18}$, Waters, 7 µm; 300×19 mm; eluent A: 0.05% trifluoroacetic acid in water, eluent B: 0.05% trifluoroacetic acid in acetonitrile; gradient: 0-5 min 5% B with flow rate 20 ml/min, 5-30 min gradient ramp of 5 to 60% B with the following flow rate increases: 22 ml/min from 6 min, 23 ml/min from 10 min, 24 ml/min from 15 min; 30-35 min gradient ramp from 60% to 98% B with flow rate decrease to 21 ml/min from 38 min; 40-45 min 10% B.

Method 11 (LC-MS): instrument type MS: Micromass ZQ; instrument type HPLC: HP 1100 Series; UV DAD; column: Grom-Sil 1200DS-4 HE 50×2 mm, 3.0 µm; eluent A: water/0.025% formic acid/l, eluent B: acetonitrile/0.025% formic acid; gradient: 0-2.9 min 0-70% B, 2.9-3.1 min 70-90% B, 3.1-4.5 min 70-90% B; oven: 50° C., flow: 0.8 ml/min, UV detection: 210 nm.

Method 12 (LC-MS): instrument type MS: Micromass LCT (ESI pos./neg.); instrument type HPLC: HP 1100 Series; UV DAD 1100 Series; column SymmetryPrep™ $C_{18}$, Waters, 50×2.1 mm, 3.5 µm; eluent A: water/0.1% formic acid, eluent B: acetonitrile/0.1% formic acid; gradient: 0-1 min 0% B, 1-5.5 min 0-95% B, 5.5-8 min 95% B, 8-8.1 min 95-0% B, 8.1-10 min 0% B, subsequent regeneration of the chromatography column. Oven: 40° C., flow: 0.5 ml/min (at 8.1-10 min for a short time to 1 ml/min), UV detection: 210 nm.

Method 13 (HPLC): instrument type HPLC: HP 1050 Series; UV DAD 1100 Series; column SymmetryPrep™ $C_{18}$, Waters, 50×2.1 mm, 3.5 µm; eluent A: water/0.05% trifluoroacetic acid, eluent B: acetonitrile; gradient: 0-9 min 0-100% B, 9-11 min 100% B, 11-12 min 100-0% B, subsequent regeneration of the chromatography column. Oven: 40° C., flow: 0.4 ml/min, UV detection: 210 nm.

Method 14 (LC-MS): instrument type MS: Micromass ZQ; instrument type HPLC: Waters Alliance 2795; column: Phenomenex Synergi 2 µm Hydro-RP Mercury 20×4 mm; eluent A: water/0.25% formic acid, eluent B: acetonitrile/0.25% formic acid; gradient: 0.0-2.5 min, 90-30% A, flow 1-2 ml/min, 2.5-3.0 min, 30-5% A, flow 2.0 min, 3.0-4.5 min, 5% A; oven: 50° C.; UV detection: 210 nm.

Method 15 (analytical HPLC): instrument type HPLC: HP 1050 Series; UV DAD 1100 Series; column: Kromasil $C_{18}$, 60×2 mm, 3.5 µm; eluent A: water/0.5% perchloric acid, eluent B: acetonitrile; gradient: 0-0.5 min 2% B, 0.5-4.5 min 2-90% B, 4.5-9.0 min 90% B, 9.0-9.2 min 90-2% B, 9.2-10.0 min 2% B; flow: 0.75 ml/min, oven: 30° C., UV detection 210 nm.

Method 16 (LC-MS): instrument: Micromass Quattro LCZ with HPLC Agilent Series 1100; column: Phenomenex Synergi 2 µHydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow: 0.0 min 1 ml/min, 2.5 min/3.0 min/4.5 min 2 ml/min; oven: 50° C.; UV detection: 208-400 nm.

Method 17 (LC-MS): instrument type MS: Micromass ZQ; instrument type HPLC: HP 1100 Series; UV DAD; column: Phenomenex Synergi 2 µHydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow: 0.0 min 1 ml/min, 2.5 min/3.0 min/4.5 min. 2 ml/min; oven: 50° C.; UV detection: 210 nm.

Method 18 (LC-MS): instrument: Micromass Quattro LCZ with HPLC Agilent Series 1100; column: Phenomenex Synergi 2 µm Hydro-RP Mercury 20 mm×4 mm; eluent A: 1 of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow: 0.0 min 1 ml/min, 2.5 min/3.0 min/4.5 min 2 ml/min; oven: 50° C.; UV detection: 208-400 nm.

Method 19 (analytical HPLC): instrument: Agilent 1100 with DAD (G1315B), binary pump (G1312A), autosampler (G1313A), solvent degasser (G1379A) and column thermostat (G1316A); column: Agilent Zorbax Eclipse XDB-C8 4.6×150×5 mm; column temperature: 30° C.; eluent A: 0.05% 70% perchloric acid in water; eluent B: acetonitrile; flow: 2.00 ml/min; gradient: 0-1 min 10% B, ramp, 4-5 min 90% B, ramp, 5.5 min 10% B.

Method 20 (MALDI-MS): The MALDI-MS/MS investigations are carried out on a 4700 Proteomics Analyzer (Applied Biosystems, Framingham, Mass., USA), which is equipped with TOF/TOF ion optics and a 200 Hz Nd:YAG laser (355 nm). The quasimolecular ions are accelerated in the ion source using 8 kV, selected using an electrical deflector (MS1), and impacted in an impact cell, which is arranged between MS1 and MS2, with argon atoms. The resulting fragment ions are re-accelerated using 15 kV and characterized using the second time of flight mass analyser (MS2).

Method 21 (TOF-HR-MS): TOF-HR-MS-ESI+ spectra are recorded using a Micromass LCT instrument (capillary voltage: 3.2 KV, cone voltage: 42 V, source temperature: 120° C., desolvation temperature: 280° C.). For this, a syringe pump (Harvard Instrument) is used for the sample supply. Leucine enkephalin (Tyr-Gly-Gly-Phe-Leu) is used as standard.

Method 22 (preparative HPLC): instrument: Gilson Abimed HPLC; UV detector 210 nm; binary pump system; column: Reprosil ODS-A, 5 µm, 250×20 mm; eluent A: 0.2% trifluoroacetic acid in water, eluent B: acetonitrile; flow rate: 25 ml/min; column temperature 40° C.; 0-10 min 20% B, 10-15 min 80% B.

Method 23 (FT-ICR-HR-MS): The mass precision measurements are carried out on a high resolution Apex II Fourier transform ion cyclotron resonance mass spectrometer (Bruker Daltonik GmbH, Bremen), which is equipped with a 7 Tesla magnet, an external electrospray ion source and a Unix-based XMASS data system. The mass resolution is about 40,000 (50% valley definition).

Method 24 (LC-MS): instrument: Micromass Platform LCZ with HPLC Agilent Series 1100; column: Phenomenex Synergi 2 µHydro-RP Mercury 20 mm×4 mm; eluent A: 1 of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow: 0.0 min 1 ml/min, 2.5 min/3.0 min/4.5 min 2 ml/min; oven: 50° C.; UV detection: 210 nm.

Method 25 (preparative HPLC) instrument: Gilson Abimed HPLC; UV detector 210 nm; binary pump system; column: Grom-Sil SNo. 4051 1200DS-4HE, 10 µm, 250×40 mm; eluent A: 0.1% trifluoroacetic acid in water, eluent B: 0.1% trifluoroacetic acid in acetonitrile; flow rate: 50 ml/min; 0-3 min 10% B, 3-27 min gradient ramp, 27-35 min 95% B, 35-40 min 10% B.

General Working Procedures

General Working Procedure 1 (Edman$^{0.5\ and\ 1.5}$)

Phenyl isothiocyanate (50 mmol) is added dropwise to a solution of the N-terminal free peptide (0.3 mmol) in dry pyridine (30 ml) under an argon protective gas atmosphere. The reaction mixture is stirred at 37° C. (about 1 h) until the analytical HPLC check (Method 13) indicates adequate conversion (>95%). The reaction mixture is concentrated in vacuo with temperature control (<40° C.) and then lyophilized.

General Working Procedure 2 (Edman$^{1.0\ and\ 2.0}$)

Under an argon protective gas atmosphere, the peptide thiourea (0.2 mmol) is treated as a solid with dry trifluoroacetic acid with vigorous stirring and then stirred at 40° C. (about 20 min) until the analytical HPLC check indicates adequate conversion (>95%). The reaction mixture is rapidly concentrated in vacuo at room temperature (temperature control). In order to free the crude product of further trifluoroacetic acid, the crude product is taken up in dichloromethane and again freed of solvent in vacuo. This process is repeated a number of times using toluene (twice) and using dichloromethane (twice). Finally, the crude product is lyophilized.

General Working Procedure 3 (Reductive Amination)

Preparation of the Deoxo(Dipeptide) Esters
Examples 25A to 37A and Examples 51A to 54A The N-protected aminoaldehyde (1.2-1.3 eq.), the amine (amino ester or Example 3A, as the hydrochloride or TFA salt) (1 eq.) and sodium acetate (1 eq.) are initially provided in anhydrous DMF and treated at 0° C. with sodium cyanoborohydride (2 eq.). The resulting solution is stirred until the complete reaction of the amine from 0° C. to RT (reaction is determined by means of analytical HPLC (Method 19) or LC-MS (Method 17)).

For small batches (up to about 0.7 mmol) the complete reaction mixture is then purified by HPLC (Method 7). For larger batches, the mixture is first pre-purified by means of a Sephadex column (Method 6), and the product obtained is subsequently purified again by means of preparative HPLC (Method 7). The product is isolated by lyophilization of the suitable fractions.

Pyridyl-containing compounds often afford a pyridyl-cyanoborane complex by this process. In this case, this is dissolved in ethanol and heated at reflux for 24 h. The free deoxodipeptidic acid ester results. This is treated with a little dimethylsulfoxide, freed of ethanol on a Rotavapor and purified by HPLC (Method 7).

General Working Procedure 4 (Deoxo(Dipeptid)ic Acid from the Methyl Ester)

Preparation of Examples 38A to 49A

The deoxo(dipeptide) methyl ester is dissolved in methanol and stirred with an excess of lithium hydroxide (5-10 eq., 1N solution in water) at RT until the analytical HPLC (Method 19) shows complete hydrolysis. The mixture is then acidified with 1N hydrochloric acid, concentrated on a Rotavapor and purified by preparative HPLC. The product is isolated by lyophilization of the suitable fractions.

General Working Procedure 5 (Hydrogenolytic Release of the Deoxo(Dipeptid)ic Acid from the Benzyl Ester)

Preparation of Example 50A

The deoxo(dipeptide) benzyl ester is dissolved in ethanol (10-15 ml/mmol) and hydrogenated under 1 atm. of hydrogen in the presence of Pd (10% on carbon) as catalyst (40-50 mg/mmol). After the reaction is complete (detected by HPLC (Method 19)), the catalyst is filtered off and washed with methanol, then the filtrate is concentrated on a rotary evaporator. The residue is dried under high vacuum.

General Working Procedure 6 (Condensation of the Deoxo (Dipeptid)ic Acid with Ed2.0)

Preparation of Examples 55A to 67A

The deoxo(dipeptid)ic acid (2 eq.) and the compound of Example 5A (1 eq.) are provided in DMF under argon and with ice cooling, NMM (4 eq.), HATU (2.1 eq.) and again NMM (5 eq.) are added and the mixture stirred at 0° C. until reaction is complete (reaction determined by means of analytical HPLC (Method 19) or LC-MS (Method 17)). For small batches (up to about 0.2 mmol) the complete reaction mixture is then purified by HPLC (Method 7). For larger batches, it is first pre-purified by means of a Sephadex column (Method 6), and the product obtained is subsequently purified again by means of preparative HPLC (Method 7). The product is isolated by lyophilization of the suitable fractions.

General Working Procedure 7 (Removal of the tert-butoxycarbonyl Protecting Group)

Preparation of Examples 1-6

The Boc-protected starting material is dissolved in dichloromethane/TFA 3:1 (20-200 ml/mmol) and stirred at RT until reaction is complete (5-20 min., check by HPLC (Method 19)). Subsequently, the mixture is diluted with 1,2-dichloroethane and concentrated on a Rotavapor. The residue is taken up in water/acetonitrile, lyophilized, then dissolved again in water and purified by preparative HPLC (Method 10). The final product is obtained by lyophilization of the suitable fractions.

General Working Procedure 8 (Removal of the benzyloxycarbonyl Protecting Group)

Preparation of Examples 7-17

The Z-protected starting material is dissolved in isopropanol (15-100 ml/mmol) and hydrogenated under 1 atm of hydrogen in the presence of Pd (10% on carbon) as a catalyst (50-200 mg/mmol). After the reaction is complete (detected by HPLC (Method 19)), the catalyst is filtered off and washed with methanol, then the filtrate is concentrated on a rotary evaporator. The residue is dissolved in water and purified by means of preparative HPLC (Method 10). The final product is obtained by lyophilization of the suitable fractions.

General Working Procedure 9 (Hydrolytic Sample Preparation for MALDI-MS)

The depsipeptide to be opened (e.g. lysobactin, 0.05 μmol) is first treated with a borate-hydrochloric acid buffer (Merck) pH 8 (250 μl) in a microvial. The mixture is allowed to stand overnight, acetic acid (100 μl) is added and the sample is freeze-dried. The crude product is investigated by means of MALDI-MS sequencing without further purification steps.

Starting Compounds

Example 1A

D-Leucyl-N$^1$-{(3S,6S,12S,15S,18R,21S,24S,27S,28R)-6-[(1S)-2-amino-1-hydroxy-2-oxoethyl]-18-(3-{[amino(imino)methyl]amino}propyl)-12-[(1S)-1-hydroxyethyl]-3-(hydroxymethyl)-24-[(1R)-1-hydroxy-2-methylpropyl]-21-isobutyl-15-[(1S)-1-methylpropyl]-2,5,8,11,14,17,20,23,26-nonaoxo-28-phenyl-1-oxa-4,7,10,13,16,19,22,25-octaazacyclooctacosan-27-yl}-L-leucinamide bistrifluoroacetate(lysobactin)

30 l fermentation: 300 ml of the flask fermentation (HPM medium) are used to inoculate a sterile 30 l nutrient medium solution (1 ml of antifoam SAG 5693/1). This culture is allowed to grow for 21 hours at 28° C., 300 rpm and aeration with sterile air of 0.3 vvm. The pH is kept constant at pH=7.2 with 1 M hydrochloric acid. In total, 880 ml of 1 M hydrochloric acid are added during the culturing period.

Main culture (200 l): 15×150 ml of YM medium in 1 l Erlenmeyer flasks are inoculated with 2 ml of the working preserve and allowed to grow on the shaker at 28° C. for 48 hours and at 240 rpm. 2250 ml of this culture are used to inoculate a sterile 200 l nutrient medium solution (YM) (1 ml of antifoam SAG 5693/1) and it is allowed to grow for 18.5 hours at 28° C., 150 rpm and aeration with sterile air of 0.3 vvm.

Hourly samples (50 ml) are taken to check the course of the fermentation. 1 ml of methanol (0.5% trifluoroacetic acid) are added to 2 ml of this culture broth are and the mixture is filtered through a 0.45 μm filter. 30 μl of this suspension are analysed by means of HPLC (Method 1 and Method 2).

After 18.5 hours, the culture broth of the main culture is separated into supernatant and sediment at 17 000 rpm.

Isolation:

The supernatant (183 l) is adjusted to pH 6.5-7 using concentrated trifluoroacetic acid or a sodium hydroxide solution and loaded onto a Lewapol column (OC 1064, 60 l contents).

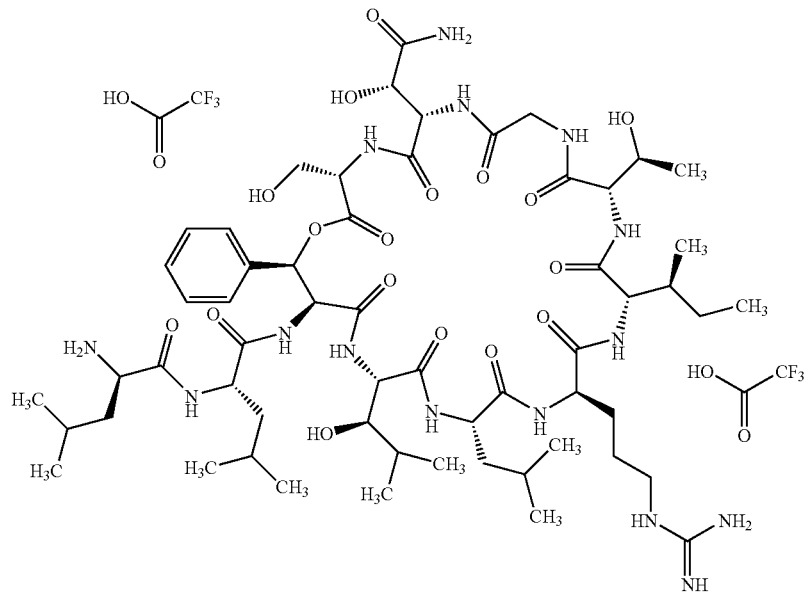

Fermentation:
Culture Medium:
YM: yeast-malt agar: D-glucose (4 g/l), yeast extract (4 g/l), malt extract (10 g/l), 1 liter of Lewatit water. Before sterilization (20 minutes at 121° C.), the pH is adjusted to 7.2.

HPM: mannitol (5.4 g/l), yeast extract (5 g/l), meat peptone (3 g/l).

Working preserve: The lyophilized strain (ATCC 53042) is grown in 50 ml of YM medium.

Flask fermentation: 150 ml of YM medium or 100 ml of HPM medium in a 1 l Erlenmeyer flask are inoculated with 2 ml of the working preserve and allowed to grow on a shaker at 240 rpm for 30-48 hours at 28° C.

Elution is subsequently carried out with pure water, water/methanol 1:1 and subsequently with pure methanol (containing 0.1% trifluoroacetic acid). This organic phase is concentrated in vacuo to a residual aqueous residue of 11.5 l.

The residual aqueous phase is bound to silica gel C$_{18}$ and separated (MPLC, Biotage Flash 75, 75×30 cm, KP-C18-WP, 15-20 μm, flow: 30 ml; eluent: acetonitrile/water containing 0.1% trifluoroacetic acid; gradient: 10%, 15% and 40% acetonitrile). The 40% acetonitrile phase, which contains the main amount of Example 1A, is concentrated in vacuo and subsequently lyophilized (about 13 g). This mixture of solids is separated in 1.2 g portions, first on a preparative HPLC (Method 3), subsequently by gel filtration on Sephadex®

LH-20 (5×70 cm, acetonitrile/water 1:1, in each case with 0.05% trifluoroacetic acid) and a further preparative HPLC (Method 4).

This process yields 2250 mg of Example 1A.

The sediment is taken up in 4 l of acetone/water 4:1, 2 kg of Celite are added, the mixture adjusted to pH=6 using trifluoroacetic acid, stirred and centrifuged. The solvent is concentrated in vacuo and the residue is freeze-dried. The lyophilizate obtained (89.9 g) is taken up in methanol, filtered, concentrated and separated on silica gel (Method 5). Example 1A is then purified by gel filtration (Sephadex LH-20, 5×68 cm, water/acetonitrile 9:1 (containing 0.05% trifluoroacetic acid), flow: 2.7 ml/min, fraction size 13.5 ml) to give the pure substance.

This process yields 447 mg of Example 1A.

HPLC (Method 1): $R_t$=6.19 min

MS (ESIpos): m/z=1277 (M+H)$^+$

The assignment of the signals was carried out according to the assignment described in the literature (T. Kato, H. Hinoo, Y. Terui, *J. Antibiot.*, 1988, 61, 719-725).

Example 2A

N-(Anilinocarbonothioyl)-D-leucyl-N$^1$-{(3S,6S,12S, 15S,18R,21S,24S,27S,28R)-6-[(1S)-2-amino-1-hydroxy-2-oxoethyl]-18-(3-{[amino(imino)methyl] amino}propyl)-12-[(1S)-1-hydroxyethyl]-3-(hydroxymethyl)-24-[(1R)-1-hydroxy-2-methylpropyl]-21-isobutyl-15-[(1S)-1-methylpropyl]-2,5,8,11,14,17,20,23,26-nonaoxo-28-phenyl-1-oxa-4,7,10,13,16,19,22,25-octaazacyclo-octacosan-27-yl}-L-leucinamide monotrifluoroacetate {N-(Anilinocarbonothioyl) lysobactin monotrifluoroacetate}

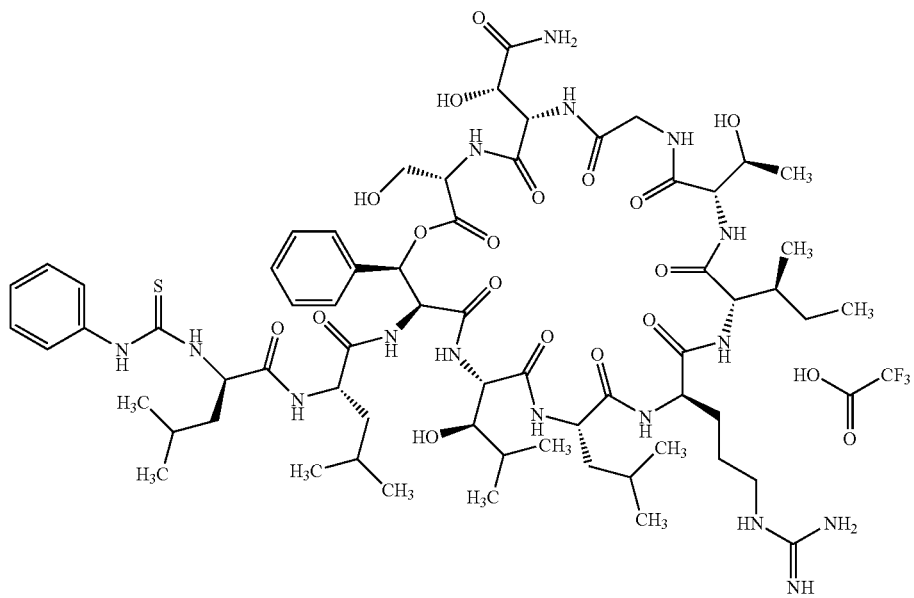

$^1$H NMR (500.13 MHz, d$_6$-DMSO): δ=0.75 (d, 3H), 0.78 (d, 6H), 0.80 (t, 3H), 0.82 (d, 3H), 0.90 (d, 3H), 0.91 (d, 3H), 0.92 (d, 3H), 0.95 (d, 3H), 0.96 (d, 3H), 1.05 (m, 1H), 1.19 (d, 3H), 1.25 (m, 2H), 1.50 (m, 4H), 1.51 (m, 2H), 1.55 (m, 1H), 1.61 (m, 1H), 1.65 (m, 1H), 1.84 (m, 1H), 1.85 (m, 1H), 1.86 (m, 1H), 1.89 (m, 1H), 1.95 (m, 1H), 2.75 (m, 2H), 3.40 (m, 1H), 3.52 (m, 2H), 3.53 (dd, 1H), 3.64 (m, 2H), 3.66 (m, 1H), 3.68 (dd, 1H), 3.73 (m, 2H), 4.00 (dd, 1H), 4.02 (br., 1H), 4.13 (br., 1H), 4.32 (dd, 1H), 4.39 (t, 1H), 4.55 (m, 1H), 4.75 (dd, 1H), 5.19 (t, 1H), 5.29 (d, 1H), 5.30 (br., 1H), 5.58 (m, 2H), 6.68 (m, 3H), 6.89 (d, 1H), 6.93 (m, 3H), 6.94 (br., 1H), 6.98 (d, 1H), 7.12 (br., 1H), 7.20 (br., 2H), 7.23 (m, 2H), 7.42 (m, 2H), 7.54 (d, 1H), 7.58 (d, 1H), 8.32 (br., 1H), 9.18 (br., 1H), 9.20 (m, 2H), 9.50 (br., 1H).

$^{13}$C-NMR (125.77 MHz, d$_6$-DMSO): δ=10.3, 15.3, 19.0, 19.2, 19.6, 20.0, 20.9, 22.0, 22.4, 23.0, 23.2, 24.3, 24.4, 25.0, 25.4, 26.0, 27.8, 30.9, 35.4, 39.5, 40.8, 40.9, 41.6, 44.1, 51.5, 52.7, 55.9, 56.2, 56.4, 57.9, 58.8, 60.2, 61.1, 62.6, 70.1, 71.6, 71.7, 75.5, 128.1, 128.6, 136.7, 156.8, 168.2, 170.1, 170.4, 171.2, 171.5, 171.9, 172.2, 172.4, 173.7.

Lysobactin bistrifluoroacetate (500 mg, 0.33 mmol) (Example 1A) is reacted according to General working procedure 1. 600 mg (quant.) of product are obtained, which can be reacted further in unpurified form.

For further purification, the crude product can be gel-chromatographed (Method 6; methanol/0.1% acetic acid). The product-containing fractions are concentrated in vacuo at room temperature and then lyophilized. The product is obtained in 80% yield.

HPLC/UV-vis (Method 13): $R_t$=6.84 min.

λ$_{max}$ (qualitative)=220 nm (s), 248 (m), 269 (m).

LC-MS (Method 11): $R_t$ 2.64 min;

MS (ESIpos.): m/z (%)=706.5 (50) [M+2H]$^{2+}$, 1412 (20) [M+H];

LC-MS (Method 12): $R_t$=4.95 min;

MS (ESIpos.): m/z (%) 1412 (100) [M+H]$^+$.

Example 3A

N¹-{(3S,6S,12S,5S,18R,21S,24S,27S,28R)-6-[(1S)-2-Amino-1-hydroxy-2-oxoethyl]-18-(3-{[amino(imino)methyl]amino}propyl)-12-[(1S)-1-hydroxyethyl]-3-(hydroxymethyl)-24-[(1R)-1-hydroxy-2-methylpropyl]-21-isobutyl-15-[(1S)-1-methylpropyl]-2,5,8,11,14,17,20,23,26-nonaoxo-28-phenyl-1-oxa-4,7,10,13,16,19,22,25-octaazacyclooctacosan-27-yl}-L-leucinamide bistrifluoro-acetate {De-D-leucyllysobactin bistrifluoroacetate}

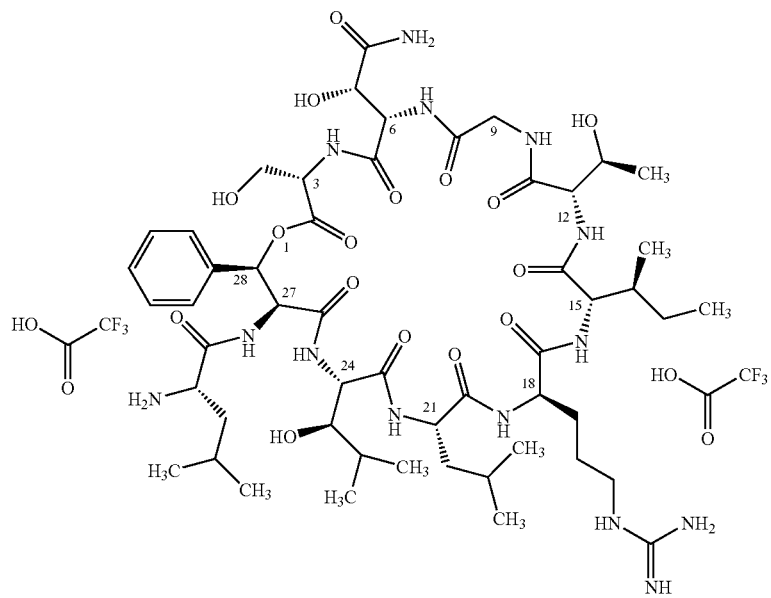

Thiourea (Example 2A) (300 mg, 0.2 mmol) is reacted according to General working procedure 2. The crude product is gel-chromatographed (Method 6; methanol/0.25% acetic acid) and subsequently finely purified by means of preparative HPLC (Method 8). 147 mg (65% of th.) of product are obtained.

HPLC/UV-vis (Method 13): $R_t$=4.96 min, $\lambda_{max}$ (qualitative)=220 nm (s), 255-270 (w).

LC-MS (Method 12): $R_t$=3.84 min;

MS (ESIpos.): m/z (%)=582.4 (100) [M+2H]²⁺, 1164 (20) [M+H]⁺.

FT-ICR-HR-MS (Method 23):

$C_{52}H_{88}N_{14}O_{16}$ [M+2H]²⁺ calc. 582.32459, fnd. 582.32460;

$C_{52}H_{87}N_{14}NaO_{16}$ [M+H+Na]²⁺ calc. 593.31556, fnd. 593.31564.

For the amino acid sequence determination, an analytical sample of the product is hydrolysed according to General working procedure 9.

MALDI-MS (Method 20): m/z (%)=1181.7 (100) [M+H]⁺.

Alternative preparation process on a larger scale:

Example 1A (6.47 g, 4.30 mmol) is dissolved in pyridine (90 ml) under an argon atmosphere. Phenyl isothiocyanate (1.16 g, 8.60 mmol, 2 equivalents) is then added and the reaction mixture is stirred at 37° C. for 1 h. Subsequently, the solvent is distilled off on a rotary evaporator and the residue is dried overnight under an oil pump vacuum. The intermediate Example 2A is obtained in a crude yield of 6.60 g. The intermediate is reacted further without purification. To this end, Example 2A (6.60 g) is dissolved in trifluoroacetic acid (107 ml) under an argon atmosphere and stirred at room temperature for 30 min. The solution is then concentrated under vacuum on a rotary evaporator, briefly dried under an oil pump vacuum, taken up in methyl tert-butyl ether (250 ml) and vigorously stirred until a powdery amorphous solid results. This is collected with vacuum-filtration and washed with methyl tert-butyl ether (200 ml), then it is washed with dichloromethane (two times 100 ml). The solid is transferred to a flask and dried under an oil pump vacuum. Example 3A is obtained in a crude yield of 6.0 g (quant.). The product can be reacted without further purification.

Example 4A

N²-(Anilinocarbonothioyl)-N¹-{(3S,6S,12S,15S,18R,21S,24S,27S,28R)-6-[(1S)-2-amino-1-hydroxy-2-oxoethyl]-18-(3-{[amino(imino)methyl]amino}propyl)-12-[(1S)-1-hydroxyethyl]-3-(hydroxymethyl)-24-[(1R)-1-hydroxy-2-methylpropyl]-21-isobutyl-15-[(1S)-1-methylpropyl]-2,5,8,11,14,17,20,23,26-nonaoxo-28-phenyl-1-oxa-4,7,10,13,16,19,22,25-octaazacyclooctacosan-27-yl}-L-leucinamide monotrifluoroacetate

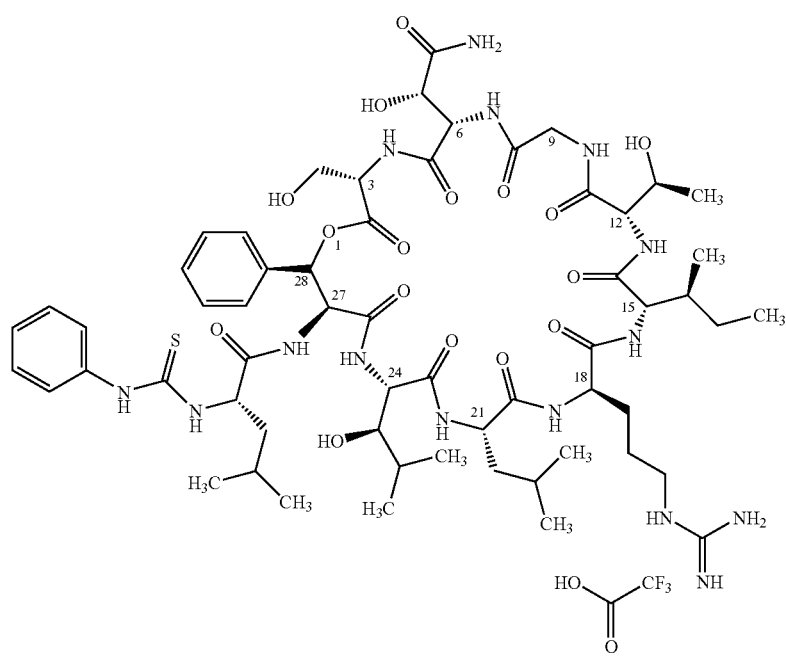

De-D-leucyllysobactin bistrifluoroacetate (Example 3A, 255 mg, 0.18 mmol) is reacted according to General working procedure 1. 322 mg (quant.) of product are obtained, which can be reacted further in unpurified form.

For further purification, the crude product can be gel-chromatographed (Method 6; methanol/0.1% acetic acid). The product-containing fractions are concentrated in vacuo at room temperature and then lyophilized.

HPLC/UV-vis (Method 13): $R_t$=6.56 min.
$\lambda_{max}$ (qualitative)=220 nm (s), 245 (m), 268 (m).
LC-MS (Method 12): $R_t$=4.85 min;
MS (ESIpos.): m/z (%)=1299 (100) [M+H]⁺.

Example 5A (2S)-2-{(3S,6S,12S,15S,18R,21S,24S,27S,28R)-27-Amino-18-(3-{[amino(imino)methyl]amino}-propyl)-12-[(1S)-1-hydroxyethyl]-3-(hydroxymethyl)-24-[(1R)-1-hydroxy-2-methylpropyl]-21-isobutyl-15-[(1S)-1-methylpropyl]-2,5,8,11,14,17,20,23,26-nonaoxo-28-phenyl-1-oxa-4,7,10,13,16,19,22,25-octaazacyclooctacosan-6-yl}-2-hydroxyethanamide bistrifluoroacetate {De(1-D-leucyl-2-L-leucyl)lysobactin bistrifluoroacetate}

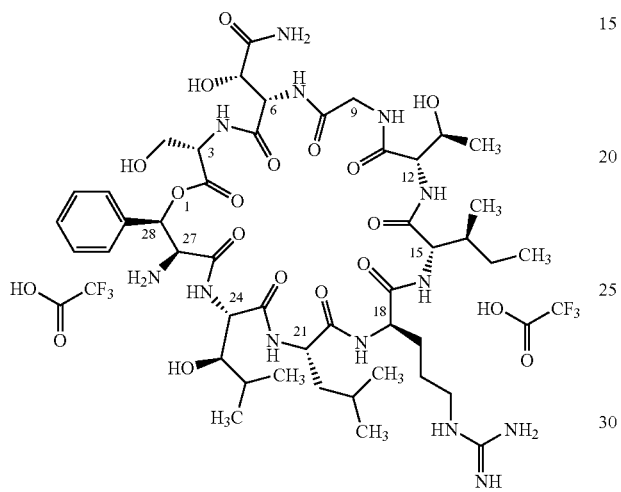

The thiourea (Example 4A, 66 mg, 34 μmol) is reacted according to General working procedure 2. The crude product can be pre-purified by rapid gel chromatography (Method 6; methanol/0.25% acetic acid). Preparative HPLC (Method 8 or Method 9 followed by subsequent double decomposition of the chromatographic product by addition of TFA (100 μmol)) yields 45 mg (75% of th.) of product.

HPLC/UV-vis (Method 13): $R_t$=4.71 min,
$\lambda_{max}$ (qualitative)=220 nm (s), 255-270 (w).
LC-MS (Method 11): $R_t$=1.65 min;
MS (ESIpos.): m/z (%)=526 (100) $[M+2H]^{2+}$, 1051 (15) $[M+H]^+$.

Alternative Preparation Process on a Larger Scale:

Example compound 3A (6.00 g, 4.30 mmol) is dissolved in pyridine (92 ml) under an argon atmosphere. Phenyl isothiocyanate (8.75 g, 64.68 mmol, 15 equivalents) is then added and the reaction mixture is stirred at 37° C. for 1 hour. Subsequently, the solvent is distilled off on a rotary evaporator and the residue is dried overnight under an oil pump vacuum. Example 4A is obtained in a crude yield of 6.0 g. The intermediate is reacted further without purification. To this end, the crude Example 4A is dissolved in trifluoroacetic acid (82 ml) under an argon atmosphere and stirred at room temperature for 30 min. The solution is then concentrated under vacuum on a rotary evaporator, dried briefly under an oil pump vacuum, taken up in methyl tert-butyl ether (250 ml) and stirred vigorously until a powdery amorphous solid results. This is collected with vacuum-filtration and washed with further methyl tert-butyl ether (200 ml), then it is washed with two portions of 100 ml each of dichloromethane. The solid is transferred to a flask and dried under an oil pump vacuum. The title compound is obtained in a crude yield of 5.4 g (quant.). The product is further purified by preparative HPLC (Method 22). 1.79 g of the title compound (32% of th.) are obtained.

Precursors from Amino Acids:

Example 6A and Example 7A

The synthesis is carried out according to M. Merget, K. Günther, M. Bernd, E. Günther, R. Tacke, *J. Organomet. Chem.* 2001628, 183-194. The enantiomers are separated by preparative HPLC on a chiral phase (Gilson Abimed HPLC, UV detector 212 nm, column: Daicel Chiralpak AD-H 5 μm; 250×20 mm; flow: 15 ml/min; eluent A: iso-hexane, eluent B: 0.2% acetic acid/1% water/2-propanol; isocratic).

Example 6A (2R)—N-tert-Butoxycarbonyl-3-trimethylsilylalanine

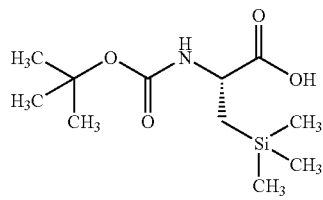

Preparative HPLC: $R_t$=9.27 min
$[\alpha]_D^{20}$=−1.6 (c=0.66, methanol)

Example 7A (2S)—N-tert-Butoxycarbonyl-3-trimethylsilylalanine

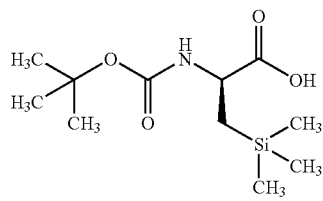

Preparative HPLC: $R_t$=4.16 min
$[\alpha]_D^{20}$=+1.1 (c=0.83, methanol)

Example 8A (2R)-3-Trimethylsilylalanine methyl ester hydrochloride

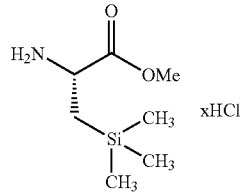

The compound of Example 6A (300 mg) is dissolved in methanol (3 ml) and cooled to 0° C. Trimethylsilyl chloride (590 mg, 4.7 eq.) is added dropwise in the course of 30 min. and the mixture is warmed to RT overnight. The volatile components are removed on a Rotavapor and subsequently under high vacuum. The target compound (224 mg, 92% of th.) is obtained.

¹H-NMR (DMSO, 300 MHz): δ=8.40 (br s, 3H), 3.93 (dd, J=5.3, 10.9 Hz, 1H), 3.73 (s, 3H), 1.71-0.97 (m, 2H), 0.03 (s, 9H).

Example 9A (2R)—N-Benzyloxycarbonyl-3-trimethylsilylalanine methyl ester

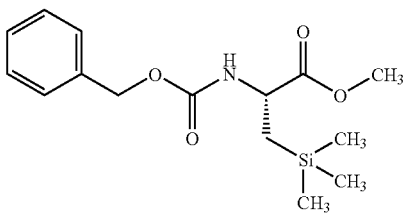

The compound of Example 8A (2.0 g) is provided in THF (40 ml) under argon at 0° C. Triethylamine (2.3 g, 2.4 eq.) is added and subsequently a solution of N-benzyloxy-carbonyloxysuccinimide (2.83 g, 1.2 eq.) in 20 ml THF is added dropwise. The mixture is then stirred overnight at RT, concentrated to a half, diluted with ethyl acetate, and washed twice with water and once with a saturated sodium chloride solution. The organic phase is dried over sodium sulfate and concentrated on a rotary evaporator. The residue is purified by preparative HPLC (Method 25). The target compound (2.32 g, 79% of th.) is obtained.

HPLC (Method 15): $R_t$=4.96 min.

MS (DCI/NH₃): m/z=327 [M+NH₄]+(100); 310 [M+H]⁺ (3).

Example 10A (2R)—N-Benzyloxycarbonyl-3-trimethylsilylalaninol

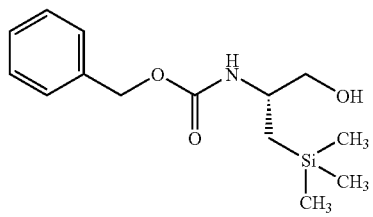

Lithium chloride (0.64 g, 15 mmol) and sodium borohydride (0.57 g, 15 mmol) and then 22 ml of ethanol are added to a solution of Example 9A (2.32 g, 7.5 mmol) in THF (14 ml). The mixture is stirred overnight at RT. For the work-up, the mixture is adjusted to pH 4 with a citric acid solution (10% in water) with cooling using ice water, then diluted with 200 ml of water and extracted three times with dichloromethane. The combined organic phases are dried over magnesium sulfate, filtered and concentrated in vacuo. The residue is separated by HPLC (Method 25) and the suitable fraction is concentrated in vacuo. Example 10A is obtained as an oil (1.24 g, 59% of th.).

HPLC (Method 15): $R_t$=4.48 min.;

MS (DCI/NH₃): m/z=299 [M+NH₄]⁺ (100); 282 [M+H]⁺ (13);

¹H-NMR (CDCl₃, 300 MHz): δ=7.33 (m, 5H), 5.08 (s, 2H), 4.72 (br.m, 1H), 3.83 (br.m, 1H), 3.65 (br.m, 1H), 3.45 (br.m, 1H), 2.13 (br.s, 1H), 0.84-0.58 (m, 2H), 0.03 (s, 9H).

Example 11A (2R)—N-Benzyloxycarbonyl-3-trimethylsilylalaninal

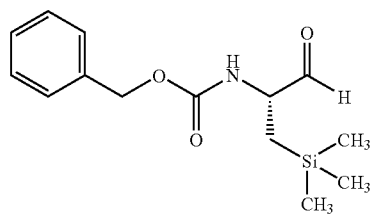

A solution of the pyridine-SO₃ complex (2.04 g, 12.8 mmol) in anhydrous DMSO (12 ml) is added at 10° C. to a solution of Example 10A (0.36 g, 1.28 mmol) and N,N-diisopropylethylamine (1.65 g, 12.8 mmol) in 7 ml of DMSO under argon. The cooling bath is removed and the mixture is subsequently stirred for 20 min. 400 ml of ice water are added and the solution is extracted three times with diethyl ether. The combined organic phases are washed twice with a citric acid solution (10% in water), once with water, once with a saturated bicarbonate solution and once with a saturated sodium chloride solution, dried over magnesium sulfate, filtered and concentrated on a rotary evaporator. Example 11A is obtained as an oil (0.39 g, 93% of th.) and directly employed further as the crude product.

MS (DCI/NH₃): m/z=297 [M+NH₄]+(100); 280 [M+H]⁺ (25).

¹H-NMR (CDCl₃, 300 MHz): δ=9.53 (s, 1H), 7.35 (m, 5H), 5.13 (s, 2H), 1.12 (dd, J=5.8, 14.0 Hz, 1H), 0.78 (dd, J=9.4, 14.0 Hz, 1H), 0.07 (s, 9H).

Example 12A (2R)—N-Benzyloxycarbonyl-D-3-tert-butylaninol

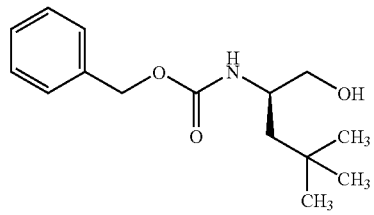

A solution of borane-tetrahydrofuran complex in THF (1M, 8.14 ml, 8.14 mmol) is slowly added dropwise to an ice-cooled solution of N-benzyloxycarbonyl-D-(3-tert-butyl) alanine dicyclohexylamine salt (1.5 g, 3.26 mmol) in anhydrous THF (15 ml) and the solution is then brought to RT with stirring in the course of 1.5 h. The mixture is treated with water with cooling, concentrated somewhat in vacuo, diluted with a saturated sodium chloride solution and extracted three times with diethyl ether. The combined organic phases are washed twice with 0.1N hydrochloric acid, twice with a saturated sodium hydrogencarbonate solution and once with a saturated sodium chloride solution, dried over sodium sulfate and concentrated on a rotary evaporator. The residue is purified by preparative HPLC (Method 25) and the suitable fractions are concentrated on a rotary evaporator and then dried under high vacuum. Yield: 485 mg (56% of th.).

HPLC (Method 15): $R_t$=4.4 min.

MS (DCI/NH$_3$): m/z=283 [M+NH$_4$]$^+$ (100); 266 [M+H]$^+$ (60).

$^1$H-NMR (CDCl$_3$, 300 MHz): δ=7.35 (m, 5H), 5.12 (s, 2H), 4.72 (br.d, J=ca. 5H), 3.83 (m, 1H), 3.63 (dd, J=4.0, 10.7 Hz, 1H), 3.51 (dd, J=6.3, 10.7 Hz, 1H), 1.44 (dd, J=2.9, 14.7 Hz, 1H), 1.28 (dd, J=8.7, 14.7 Hz, 1H), 0.95 (s, 9H).

Example 13A (2R)—N-tert-Butoxycarbonyl-3-trimethylsilylalaninol

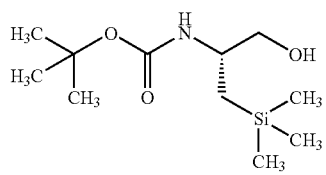

The preparation takes place starting from Example 6A (2.45 g, 9.37 mmol) using borane-tetrahydrofuran complex (2 eq.) according to the same process as described for Example 12A. Example 13A (1.70 g, 73% of th.) is obtained after chromatography on silica gel (dichloromethane/methanol 100:3).

HPLC (Method 15): $R_t$=4.4 min.

MS (ESI pos): m/z=270 [M+Na]$^+$ (46); 192 (100).

$^1$H-NMR (CDCl$_3$, 300 MHz): δ=4.60-4.38 (br.m, 1H), 3.87-3.72 (br.m, 1H), 3.69-3.56 (br.m, 1H), 3.50-3.38 (br.m, 1H), 2.40 (br.s, 1H) 1.44 (s, 9H), 0.82-0.66 (m, 2H), 0.04 (s, 9H).

Example 14A (2R)—N-tert-Butoxycarbonyl-3-trimethylsilylalaninal

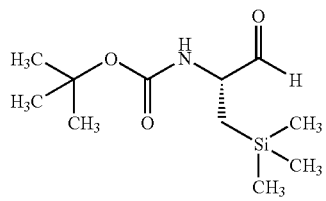

The title compound is prepared from Example 13A (620 mg, 2.51 mmol) in analogy to the synthesis of Example 11A. Yield 550 mg (80% of th.). Example 14A is reacted without further purification.

$^1$H-NMR (CDCl$_3$, 300 MHz): o=9.50 (s, 1H), 4.93-4.82 (br.m, 1H), 4.26 (br.q, J=ca. 7-8 Hz, 1H), 1.44 (s, 9H), 1.09 (br. dd, J=5.3, 14.8 Hz, 1H), 0.74 (dd, J=10.0, 14.8 Hz, 1H), 0.08 (s, 9H).

In analogy to the synthesis procedures described above, the following starting compounds are prepared from commercially available amino acid derivatives:

Example 15A (2S)—N-Benzyloxycarbonyl-L-3-tert-butylalaninol

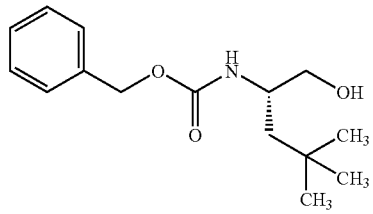

HPLC (Method 15): $R_t$=4.42 min.;

MS (DCI/NH$_3$): m/z=283 [M+NH$_4$]$^+$ (100); 266 [M+H]$^+$ (58);

$^1$H-NMR (CDCl$_3$, 300 MHz): δ=7.33 (m, 5H), 5.11 (s, 2H), 4.71 (m, 1H), 3.83 (m, 1H), 3.62 (dd, J=4.2, 10.5 Hz, 1H), 3.45 (dd, J=6.3, 10.9 Hz, 1H), 1.43 (dd, J=2.9, 14.6 Hz, 1H), 1.29 (dd, J=8.9, 14.6, 1H), 0.93 (s, 9H).

Example 16A (2S)—N-Benzyloxycarbonyl-L-3-tert-butylalaninal

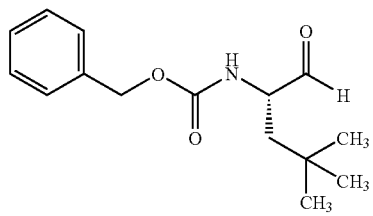

MS (DCI/NH$_3$): m/z=281 [M+NH$_4$]$^+$ (100); 264 [M+H]$^+$ (20).

$^1$H-NMR (CDCl$_3$, 300 MHz): δ=9.58 (s, 1H), 7.36 (m, 5H), 5.12 (s, 2H), 5.06 (m, 1H), 4.33 (dt, J=3.8, 8.7 Hz, 1H), 1.83 (dd, J=3.8, 14.6 Hz, 1H), 1.30 (dd, J=8.3, 14.7 Hz, 1H), 1.00 (s, 9H).

Example 17A (2R)—N-Benzyloxycarbonyl-D-3-tert-butylalaninal

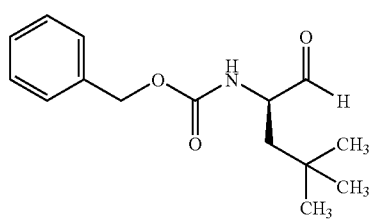

MS (DCI/NH$_3$): m/z=281 [M+NH$_4$]$^+$ (100); 264 [M+H]$^+$ (18).

¹H-NMR (CDCl₃, 300 MHz): δ=9.58 (s, 1H), 7.36 (m, 5H), 5.12 (s, 2H), 5.08 (m, 1H), 4.33 (dt, J=3.8, 8.7 Hz, 1H), 1.83 (dd, J=3.8, 14.6 Hz, 1H), 1.30 (dd, J=8.3, 14.7 Hz, 1H), 1.00 (s, 9H).

Example 18A (2S)—N-Benzyloxycarbonyl-L-leucinal

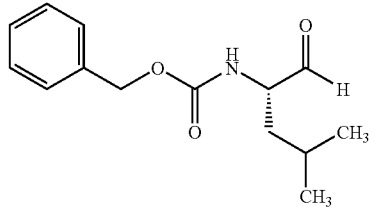

MS (DCI/NH₃): m/z=267 [M+NH₄]⁺ (100); 250 [M+H]⁺ (8).
¹H-NMR (CDCl₃, 400 MHz): δ=9.61 (s, 1H), 7.38 (m, 5H), 5.18 (m, 1H), 5.02 (s, 2H), 4.35 (m, 1H), 1.62-1.55 (m, 2H), 1.41 (m, 1H), 0.96 (d, J=0.7 Hz, 3H), 0.94 (d, J=7 Hz, 3H).

Example 19A (2R)—N-Benzyloxycarbonyl-D-leucinal

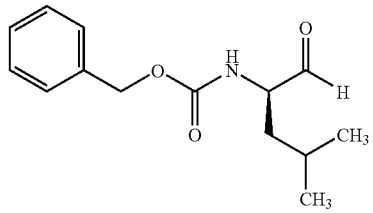

MS (DCI/NH₃): m/z=267 [M+NH₄]⁺ (100); 250 [M+H]⁺ (10).
¹H-NMR (CDCl₃, 300 MHz): δ=9.61 (s, 11H), 7.38 (m, 5H), 5.18 (m, 11H), 5.12 (m, 2H), 4.35 (m, 1H), 1.85-1.50 (m, 2H), 1.41 (m, 1H), 0.95 (m, 6H).

Example 20A (2S)—N-tert-Butoxycarbonyl-L-3-tert-butylalaninal

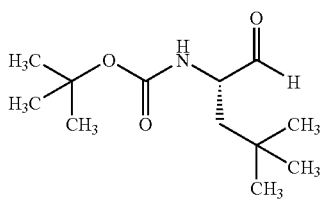

MS (DCI/NH₃): m/z=247 [M+NH₄]⁺ (15); 230 [M+H]⁺ (31), 191 (100).
¹H-NMR (CDCl₃, 400 MHz): δ=9.58 (s, 1H), 4.82 (m, 1H), 4.25 (m, 1H), 1.80 (dd, J 2, 14.6 Hz, 1H), 1.44 (s, 9H), 1.25 (dd, J=8.7, 14.6 Hz, 1H), 1.00 (s, 9H).

Example 21A (2R)—N-tert-Butoxycarbonyl-D-3-tert-butylalaninal

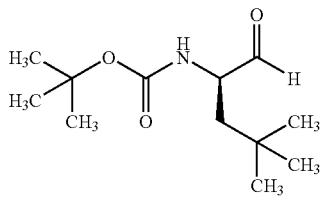

MS (DCI/NH₃): m/z=247 [M+NH₄]⁺ (13); 230 [M+H]⁺ (28), 191 (100).
¹H-NMR (CDCl₃, 400 MHz): δ=9.58 (s, 1H), 4.82 (m, 1H), 4.25 (m, 1H), 1.80 (dd, J=2, 14.6 Hz, 1H), 1.44 (s, 9H), 1.25 (dd, J=8.7, 14.6 Hz, 1H), 1.00 (s, 9H).

Example 22A

L-β-(3-Pyridyl)alanine methyl ester bishydrochloride

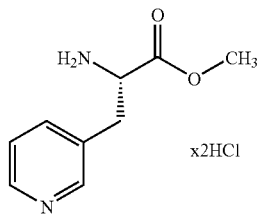

In analogy to the preparation of Example 8A, the commercially available Boc-L-β-(3-pyridyl)alanine is treated with trimethylsilyl chloride in methanol. After the reaction is complete, the reaction mixture is treated with diethyl ether and the precipitated crystalline product is filtered off. The product is washed with cold diethyl ether and dried under high vacuum. Yield: 94% of th.

HPLC (Method 15): R_t=4.29 min.
¹H-NMR (DMSO, 400 MHz): δ=8.86 (s, 1H), 8.82 (br. s, 3H), 8.80 (d, J=5.5 Hz, 1H), 8.38 (d, J=8.0 Hz, 1H), 7.92 (dd, J=5.5, 8.0 Hz, 1H), 4.50 (m, 1H), 3.74 (s, 3H), 3.38 (m [ABX], 2H).

Example 23A

L-β-(3,4-Dimethoxyphenyl)alanine methyl ester hydrochloride

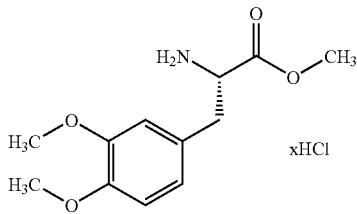

The commercially available L-β-(3,4-dimethoxyphenyl) alanine (225 mg, 1 mmol) is provided in methanol (5 ml), thionyl chloride (73 μl, 1 eq.) is added and the mixture is heated at reflux for 1 h, then concentrated on a rotary evaporator and dried under high vacuum. 277 mg of product are obtained.

$^1$H-NMR (DMSO, 300 MHz): δ=8.55 (br.s, 3H), 6.89 (d, J=8.0 Hz, 1H), (d, J=1.9 Hz, 1H), 6.73 (dd, J=1.9, 8.0 Hz, 1H), 4.25 (br.t, J=ca. 6 Hz, 1H), 3.75 (s, 3H), 3.73 (s, 3H), 3.71 (s, 3H), 3.08 (d, J=6.2 Hz, 2H).

Example 24A

L-β-tert-Butylalanine methyl ester hydrotrifluoroacetate

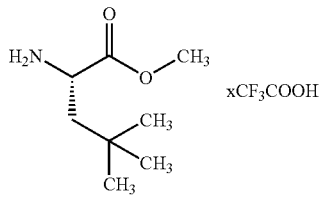

The (2S)—N-tert-butoxycarbonyl-L-3-tert-butylalanine methyl ester (529 mg, 2.04 mmol) is stirred at RT in TFA/dichloromethane 1:3 (3 ml), and the solution is concentrated on a rotary evaporator and dried under high vacuum. 540 mg (97% of th.) of product are obtained.

$^1$H-NMR (DMSO, 300 MHz): δ=8.33 (br.s, 3H), 3.95 (dd, J=4.7, 7.5 Hz, 1H), 3.76 (s, 3H), 1.80 (dd, J=7.5, 14.4 Hz, 1H), 1.59 (dd, J=4.7, 14.4 Hz, 1H), 0.92 (s, 9H).

Deoxodipeptide Esters

The following Examples 25A to 37A are prepared according to General working procedure 3:

Example 25A

N-[(2R)-2-Benzyloxycarbonylamino-4,4-dimethyl-pentyl]-β-tert-butylalanine methyl ester hydro-trifluoroacetate (Z-D-β-tBu-Ala(ΨCH$_2$NH)-L-β-tBu-Ala-OMe).TFA

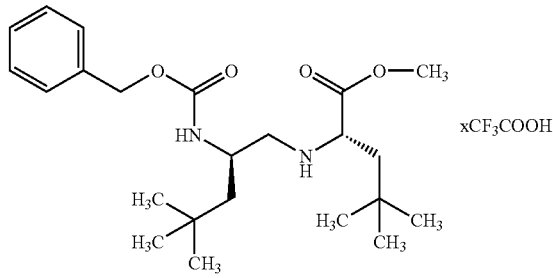

Preparation from Example 17A and Example 24A. Yield: 220 mg (65% of th.).

HPLC (Method 15): R$_t$=4.7 min.;

MS (DCI/NH$_3$): m/z=407 [M+H]$^+$ (100);

$^1$H-NMR (CDCl$_3$, 300 MHz): β=7.34 (s, 5H), 5.52 (br.d, J=6.6 Hz, 1H), 5.14 (q, J=12 Hz, 1H), 5.06 (q, J=12 Hz, 1H), 4.09-3.95 (m, 2H), 3.79 (s, 3H), 3.25-3.03 (m, 2H), 2.01-1.78 (m, 2H), 1.50 (dd, J=7.8, 15, 1H), 1.34 (m, 1H), 0.94 (s, 9H), 0.92 (s, 9H).

Example 26A

N-[(2S)-2-Benzyloxycarbonylamino-4,4-dimethyl-pentyl]-β-tert-butylalanine methyl ester hydro-trifluoroacetate (Z-L-β-tBu-Ala(ΨCH$_2$NH)-L-O-tBu-Ala-OMe).TFA

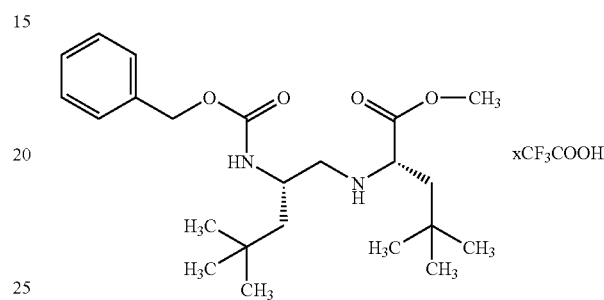

Preparation from Example 16A and Example 24A. Yield: 860 mg (36% of th.).

HPLC (Method 15): R$_t$=4.7 min.;

MS (ESI pos): m/z=407 [M+H]$^+$ (100);

$^1$H-NMR (CDCl$_3$, 300 MHz): δ=7.32 (m, 5H), 5.73 (br.d, J=8.5 Hz, 1H), 5.13 (d, J=12 Hz, 1H), 5.04 (d, J=12 Hz, 1H), 3.99 (m, 1H), 3.84 (m, 1H), 3.80 (s, 3H), 3.33 (dd, J=10.5, 12 Hz, 1H), 2.89 (dd, J=3.5, 12 Hz, 1H), 1.95-1.68 (m, 2H), 1.53 (dd, J=8.7, 14.7, 1H), 1.34 (br.d, J=15, 1H), 0.93 (s, 9H), 0.91 (s, 1H).

Example 27A

N-[(2R)-2-Benzyloxycarbonylamino-4-methylpen-tyl]-β-(3-pyridyl)alanine methyl ester bishydro-trifluoroacetate (Z-D-Leu(ΨCH$_2$NH)-L-β-(3-pyridyl)-Ala-OMe).2TFA

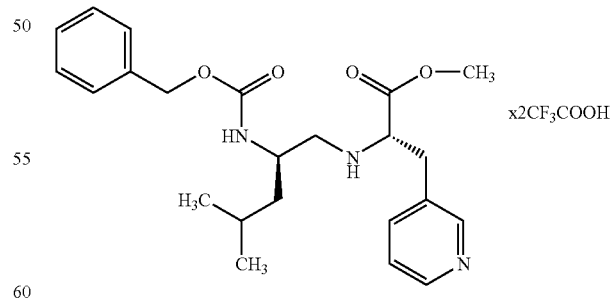

Preparation from Example 19A and Example 22A. Yield: 800 mg (60% of th.).

LC-MS (Method 16): R$_t$=1.67 min. ES$^+$: m/z=414 [M+H]$^+$, ES$^-$: 458 [M+HCOOH−H]$^+$;

$^1$H-NMR (CDCl$_3$, 300 MHz): δ=8.68 (s, 1H), 8.51 (d, J=4.4 Hz, 1H), 8.1 (br.d, J=7.2 Hz, 1H), 7.54 (dd, J=5.1, 7.7

Hz, 1H), 7.38-7.28 (m, 5H), 5.12 (m, 1H), 5.03 (d, J=12.2 Hz, 1H), 4.97 (d, J=12.2 Hz, 1H), 3.99 (m, 1H), 3.84 (m, 1H), 3.79 (s, 3H), 3.33-2.99 (m, 3H), 2.85 (m, 1H), 11.61 (m, 1H), 1.42-1.20 (m, 2H), 0.82-0.98 (m, 6H).

Example 28A

N-[(2S)-2-Benzyloxycarbonylamino-4-methylpentyl]-β-(3-pyridyl)alanine methyl ester bishydro trifluoroacetate (Z-L-Leu(ΨCH$_2$NH)-L-β-(3-pyridyl)-Ala-OMe) .2TFA

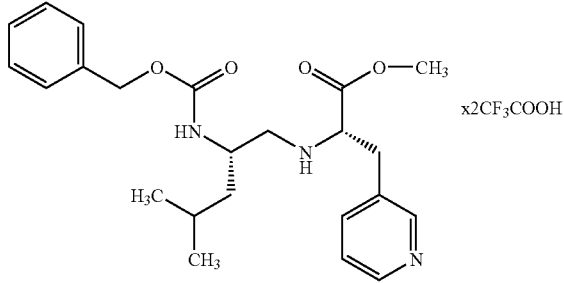

Preparation from Example 18A and Example 22A. Yield 410 mg (48% of th.).

LC-MS (Method 14): R$_t$=1.51 min. ES$^+$: m/z=414 [M+H]$^+$, ES$^-$: 458 [M+HCOOH−H]$^-$.

$^1$H-NMR (CDCl$_3$, 400 MHz): δ=8.90 (s, 1H), 8.66 (d, J=5.5 Hz, 1H), 8.33 (d, J=8.3 Hz, 1H), 7.69 (dd, J=5.5, 7.8 Hz, 1H), 7.39-7.28 (m, 5H), 5.36 (d, J=7.1, 1H), 5.06 (m [AB], 2H), 4.35 (t, J=5.1 Hz, 1H), 3.84 (s, 3H), 3.54 (d, J=5.4 Hz, 1H), 3.28 (t, J=10.6 Hz, 1H), 3.08 (d, J=10.5 Hz, 1H), 1.62 (m, 1H), 1.45 (ddd, J=5.4, 9.1, 14.3 Hz, 1H), 1.29 (ddd, J=4.9, 8.4, 13.9 Hz, 2H), 0.90 (d, J=6.6 Hz, 3H), 0.90 (d, J=6.4 Hz, 3H).

Example 29A

N-[(2S)-2-tert-Butoxycarbonylamino-4,4-dimethylpentyl]-β-(3-pyridyl)alanine methyl ester bis-hydrotrifluoroacetate (Boc-L-β-tBu-Ala(ΨCH$_2$NH)-L-β-(3-pyridyl)-Ala-OMe).2TFA

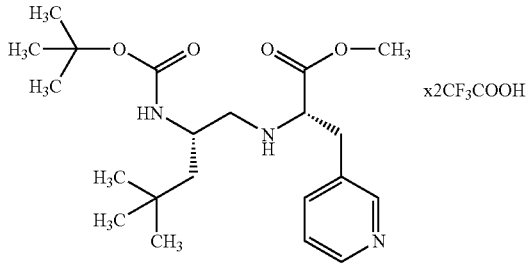

Preparation from Example 20A and Example 22A. Yield: 160 mg (59% of th.).

HPLC (Method 15): R$_t$=4.0 min.;

MS (ESI pos): m/z=394 [M+H]$^+$ (92), 338 (80), 294 (100).

$^1$H-NMR (CDCl$_3$, 400 MHz): δ=8.51 (s, 1H), 8.75 (d, J=5.4 Hz, 1H), 8.48 (d, J=7.8 Hz, 1H), 7.83 (dd, J=5.5, 7.8 Hz, 1H), 4.98 (br.d, J=6.1 Hz, 1H), 4.38 (t, J=5.6 Hz, 1H), 3.87 (s, 3H), 3.67-3.52 (m, 2H), 3.35 (t, J=10.5 Hz, 1H), 2.98 (d, J=11.7 Hz, 1H), 1.44 (dd, J=9.0, 14.9 Hz, 1H), 1.40 (s, 9H), 1.31 (dd, J=2.6, 14.8 Hz, 1H), 0.93 (s, 9H).

Example 30A

N-[(2S)-2-Benzyloxycarbonylamino-4-methylpentyl]-β-(3,4-dimethoxyphenyl)alanine methyl ester hydrotrifluoroacetate (Z-L-Leu(ΨCH$_2$NH)-L-β-(3,4-dimethoxyphenyl)-Ala-OMe).TFA

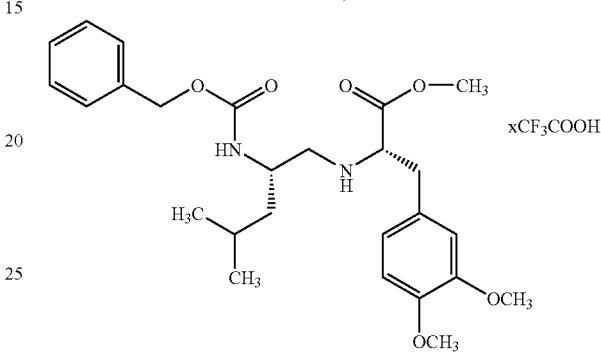

Preparation from Example 18A and Example 23A. Yield 200 mg (32% of th.).

LC-MS (Method 16): R$_t$=1.91 min. ES$^+$: m/z=473 [M+H]$^+$, ES$^-$: 517 [M+HCOOH−H]$^-$.

$^1$H-NMR (DMSO, 300 MHz): δ=9.50-9.00 (br.s, 2H), 7.40-723 (m, 6H), 6.90 (d, J=8.1 Hz, 1H), 6.82 (d, J=1.5 Hz, 1H), 6.71 (dd, J=1.6, 8.2 Hz, 1H), 5.05 (q [AB], J=12.5 Hz, 2H), 4.30 (m, 1H), 3.85 (m, 1H), 3.75 (s, 3H), 3.73 (s, 3H), 3.64 (s, 3H), 3.20 (dd, J=5.1, 13.7 Hz, 1H), 3.07-2.93 (m, 3H), 1.58 (m, 1H), 1.38 (ddd, J=4.6, 9.5, 14.1 Hz, 1H), 1.22 (ddd, J=4.5, 8.8, 14 Hz, 1H), 0.86 (t, J=6.4 Hz, 6H).

Example 31A

N-[(2R)-2-Benzyloxycarbonylamino-4-methylpentyl]-β-(3,4-dimethoxyphenyl)alanine methyl ester hydrotrifluoroacetate (Z-D-Leu(ΨCH$_2$NH)-L-β-(3,4-dimethoxyphenyl)-Ala-OMe).TFA

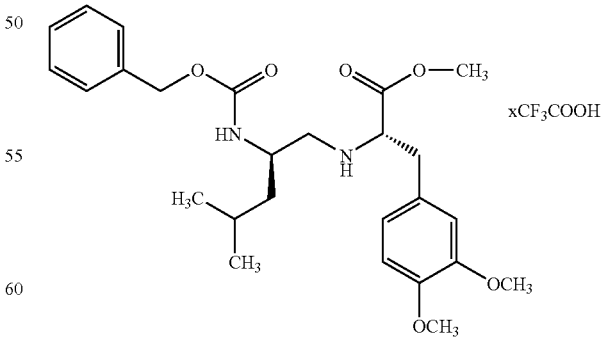

Preparation from Example 19A and Example 23A. Yield 190 mg (31% of th.).

LC-MS (Method 16): R$_t$=1.66 min. ES$^+$: m/z=473 [M+H]$^+$, ES$^-$: 517 [M+HCOOH−H]$^-$.

¹H-NMR (CDCl₃, 400 MHz): δ=7.38-7.23 (m, 5H), 6.82-6.77 (m, 2H), 6.67 (dd, J=1.8, 7.8 Hz, 1H), 5.18 (d, J=6.2 Hz, 1H), 4.99 (s, 2H), 4.23 (t, J=5.4 Hz, 1H), 3.98 (m, 1H), 3.90 (s, 3H), 3.81 (s, 3H), 3.72 (s, 3H), 3.34 (d, J=12.0 Hz, 1H), 3.27 (d, J=5.4 Hz, 2H), 2.94 (t, J=10.8 Hz, 1H), 1.59 (m, 1H), 1.42-1.25 (m, 2H), 0.90 (t, J=6.5 Hz, 6H).

Example 32A

N-[(2R)-2-tert-Butoxycarbonylamino-3-trimethylsilylpropyl]-β-(3-pyridyl)alanine methyl ester hydrotrifluoroacetate (Boc-L-β-Trimethylsilyl-Ala(ΨCH₂NH)-L-β-(3-pyridyl)-Ala-OMe)TFA

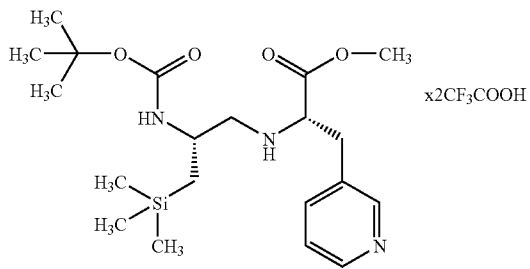

Preparation from Example 14A and Example 22A. Yield: 270 mg (73% of th.).

HPLC (Method 15): R_t=4.2 min.;

MS (ESI pos): m/z (%)=410 [M+H]⁺ (100), 354 (77), 310 (73), 293 (70), 221 (97).

¹H-NMR (CDCl₃, 300 MHz): δ=8.85 (s, 1H), 8.71 (d, J=5.2 Hz, 1H), 8.47 (br.d, J=7.4 Hz, 1H), 7.80 (br.dd, J=4.8, 7.6 Hz, 1H), 4.94 (br.d, J=6.0 Hz, 1H), 4.40-4.30 (m, 1H), 3.99-3.84 (m, 1H), 3.89 (s, 3H), 3.65-3.52 (m, 2H), 3.32 (br.t, J=ca. 10 Hz, 1H), 2.98 (br.d, J=10.5 Hz, 1H), 1.41 (s, 9H), 0.90 (dd, J=10.5, 15.0, 1H), 0.75 (dd, J=4.5, 15.0, 1H), 0.05 (s, 9H).

Example 33A

N-[(2R)-2-tert-Butoxycarbonylamino-3-trimethylsilylpropyl]leucine benzyl ester hydrotrifluoro-acetate (Boc-L-β-Trimethysilyl-Ala(ΨCH₂NH)-L-Leu-OBn) TFA

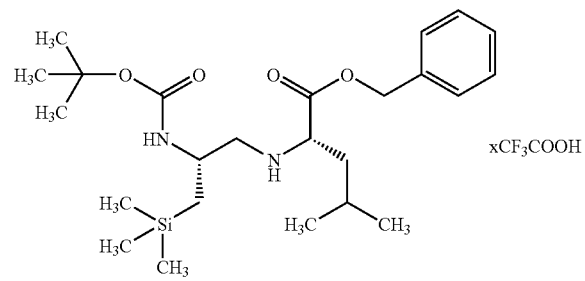

Preparation from Example 14A and L-leucine benzyl ester hydrotosylate. Yield 180 mg (28% of th.).

HPLC (Method 15): R_t=5.1 min.

¹H-NMR (CDCl₃, 400 MHz): δ=7.41-7.34 (m, 5H), 5.23 (m [AB], 2H), 5.06 (br.d, J=ca. 5.0 Hz, 1H), 4.03-3.92 (m, 2H), 3.30 (t, J=10.5 Hz, 1H), 2.91 (d, J=11.0 Hz, 1H), 1.80 (m, 2H), 1.66 (m, 1H), 1.43 (s, 9H), 0.91 (d, J=2.2 Hz, 3H), 0.89 (d, J=1.9 Hz, 3H), 0.85 (dd, J=10.3, 14.7 Hz, 1H), 0.68 (dd, J=5.0, 14.6 Hz, 1H), 0.04 (s, 9H).

Example 34A

N-[(2R)-2-Benzyloxycarbonylamino-3-trimethylsilylpropyl]-β-tert-butylalanine methyl ester hydrotrifluoroacetate (Z-L-β-Trimethylsilyl-Ala(ΨCH₂NH)-L-β-tBu-Ala-OMe) TFA

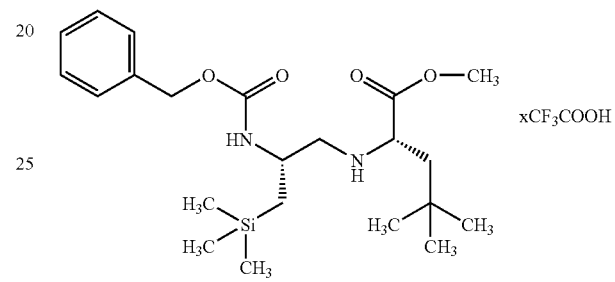

Preparation from Example 11A and Example 24A. Yield 390 mg (66% of th.). HPLC (Method 15): R_t=4.8 min.

MS (ESI pos.): m/z=423 [M+H]⁺ (100).

¹H-NMR (CDCl₃, 300 MHz): δ=7.33 (s, 5H), 5.63 (d, J=0.9 Hz, 1H), 5.16 (d, J=11.5 Hz, 1H), 5.05 (d, J=11.5 Hz, 1H), 4.07-3.90 (m, 1H), 3.85 (dd, J=4.5, 7.9 Hz, 1H), 3.81 (s, 3H), 3.35 (dd, J=9.8, 11.3 Hz, 1H), 2.93 (dd, J=2.5, 12.5 Hz, 1H), 1.95-1.80 (m, 2H), 0.95 (dd, J=10.2, 14.7 Hz, 1H), 0.94 (s, 9H), 0.76 (dd, J=5.1, 14.7 Hz, 1H), 0.03 (s, 9H).

Example 35A

N-[(2S)-2-Benzyloxycarbonylamino-4,4-dimethylpentyl]-β-trimethylsilylalanine methyl ester hydrotrifluoroacetate (Z-L-β-t-Butyl-Ala(ΨCH₂NH)-L-β-(trimethylsilyl)-Ala-OMe) TFA

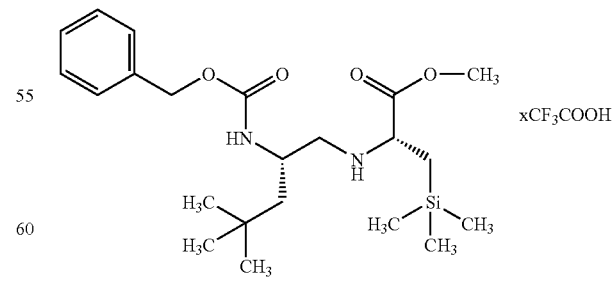

Preparation from Example 16A and Example 8A. Yield 106 mg (37% of th.).

HPLC (Method 15): R_t=4.8 min.

MS (DCI/NH₃): m/z=423 (100) [M+H]⁺.

¹H-NMR (CDCl₃, 300 MHz): δ=7.32 (br.s, 5H), 8.76 (br.d, J=9 Hz, 1H), 5.15 (d, J=12 Hz, 1H), 5.05 (d, J=12 Hz, 1H), 4.03 (m, 1H), 3.94 (dd, J=12.6, 3.8 Hz, 1H), 3.78 (s, 3H), 3.34 (dd, J=10, 12 Hz, 1H), 2.87 (dd, J=4, 12 Hz, 1H), 1.53 (dd, J=8.9, 14.7 Hz, 1H), 1.40-1.22 (m, 2H), 1.12 (dd, J=12.5, 13.5 Hz, 1H), 0.92 (s, 9H), 0.06 (s, 9H).

Example 36A

N-[(2R)-2-Benzyloxycarbonylamino-3-trimethylsilylpropyl]-β-trimethylsilylalanine methyl ester hydrotrifluoroacetate (Z-L-β-Trimethylsilyl-Ala(ΨCH₂NH)-L-β-(trimethylsilyl)-Ala-OMe) TFA

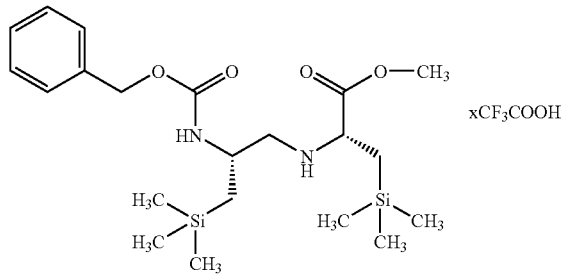

Preparation from Example 11A and Example 8A. Yield 54 mg (24% of th.).

HPLC (Method 15): R_f=4.93 min.

¹H-NMR (CDCl₃, 400 MHz): δ=7.36-7.26 (m, 5H), 5.47 (br.d, J=6 Hz, 1H), 5.16 (d, J=12.4 Hz, 1H), 5.04 (d, J=12.4 Hz, 1H), 4.04 (m, 1H), 3.96 (d, J=10.8 Hz, 1H), 3.70 (s, 3H), 3.32 (t, J=9.7 Hz, 1H), 2.91 (d, J=11.3 Hz, 1H), 1.31 (br.d, J=14.2 Hz, 1H), 1.12 (t, J=12.7 Hz, 1H), 0.92 (dd, J=9.8, 14.9 Hz, 1H), 0.74 (dd, J=4.8, 14.4 Hz, 1H), 0.06 (s, 9H), 0.02 (s, 9H).

Example 37A

N-[(2S)-2-Benzyloxycarbonylamino-4,4-dimethylpentyl]-O⁵-tert-butylaspartic acid methyl ester hydrotrifluoroacetate (Z-L-β-tBu-Ala(ΨCH₂NH)-L-Asp(tBu)-OMe) TFA

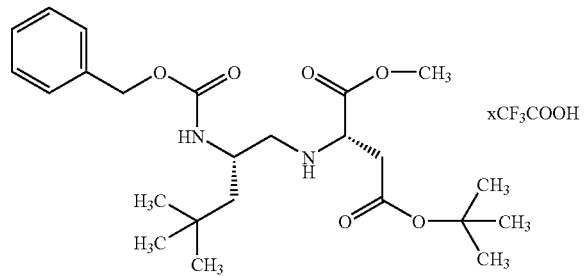

Preparation from Example 16A and H-Asp(tBu)-OMe hydrochloride. Yield 212 mg (46% of th.).

HPLC (Method 15): R_f=4.7 min.

MS (DCI/NH₃): m/z=451 (100) [M+H]⁺, 317 (23).

¹H-NMR (CDCl₃, 300 MHz): δ=7.37-7.27 (m, 5H), 8.76 (br.d, J=9 Hz, 1H), 5.53 (d, J=7.9 Hz, 1H), 5.09 (q [AB], J=12.2 Hz, 2H), 4.13 (m, 1H), 4.07 (t, J=4.7 Hz, 1H), 3.82 (s, 3H), 3.37 (br.t, J=10.8 Hz, 1H), 3.21-2.99 (m, 3H), 1.53 (dd, J=8.8, 14.5 Hz, 1H), 1.44 (s, 9H), 1.32 (dd, J=2.7, 14.5 Hz, 1H), 0.92 (s, 9H).

Deoxodipeptidic Acids

The following deoxodipeptidic acids (Examples 38A to 49A) are prepared according to General working procedure 4:

Example 38A

N-[(2R)-2-Benzyloxycarbonylamino-4,4-dimethylpentyl]-β-tert-butylalanine hydrotrifluoroacetate (Z-D-β-tBu-Ala(ΨCH₂NH)-L-β-tBu-Ala-OH) TFA

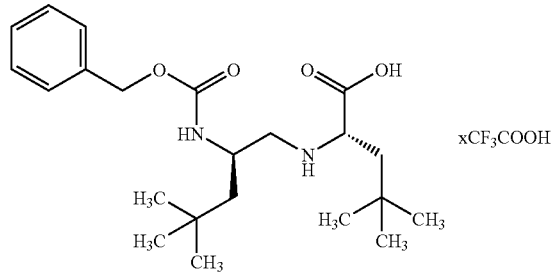

Preparation from Example 25A. Yield: 103 mg (51% of th.).

HPLC (Method 15): R_f=4.5 min.;

MS (ESI pos.): m/z=393 [M+H]⁺, (ESI neg.): 391 [M−H]⁻.

¹H-NMR (DMSO, 300 MHz): δ=9.30-8.60 (br, 1H), 7.40-7.22 (m, 6H), 5.13 (d, J=12.7 Hz, 1H), 4.97 (d, J=12.7 Hz, 1H), 3.92 (m, 1H), 3.84 (br.d, J=8.9 Hz, 1H), 2.94 (br.d, J=12.1 Hz, 1H), 2.81 (dd, J=10.2, 12.2 Hz, 1H), 1.80 (dd, J=9.5, 13.8 Hz, 1H), 1.67 (br.d, J=9.5 Hz, 1H), 1.44 (dd, J=8.6, 14.2 Hz, 1H), 1.30 (dd, J=2.2, 14.2 Hz, 1H), 0.93 (s, 9H), 0.87 (s, 9H).

Example 39A

N-[(2S)-2-Benzyloxycarbonylamino-4,4-dimethylpentyl]-β-tert-butylalanine hydrotrifluoroacetate (Z-L-β-tBu-Ala(ΨCH₂NH)-L-β-tBu-Ala-OH) TFA

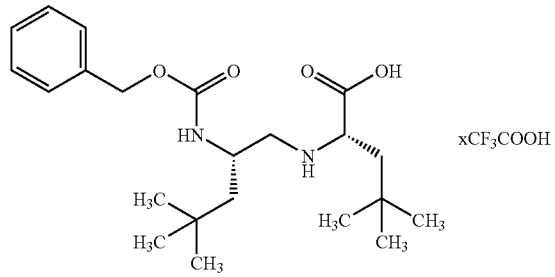

Preparation from Example 26A. Yield: 895 mg (83% of th.).

HPLC (Method 15): R_f=4.5 min.

MS (ESI pos.): m/z=393 [M+H]⁺ (100); ES⁻: 391 (4).

¹H-NMR (DMSO, 300 MHz): δ=7.40-7.27 (m, 5H), 7.07 (d, J=9.0 Hz, 1H), 5.12 (d, J=12.7 Hz, 1H), 4.99 (d, J=12.7 Hz, 1H), 3.99-3.85 (m, 2H), 2.98 (m, 1H), 2.88 (m, 1H), 1.81 (dd, J=9.7, 14 Hz, 1H), 1.64 (dd, J=2, 14 Hz, 1H), 1.45-1.30 (m, 2H), 0.93 (s, 9H), 0.89 (s, 9H).

Example 40A

N-[(2R)-2-Benzyloxycarbonylamino-4-methylpentyl]-β-(3-pyridyl)alanine bishydrotrifluoroacetate (Z-D-Leu(ΨCH₂NH)-L-β-(3-pyridyl)-Ala-OH)2 TFA

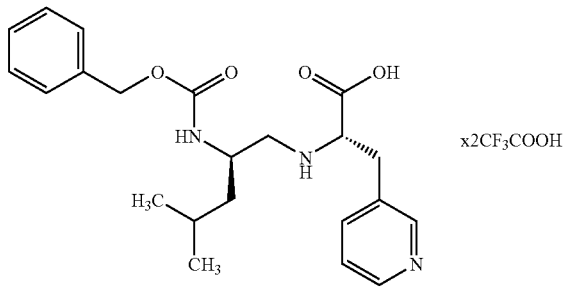

Preparation from Example 27A. Yield: 744 mg (95% of th.).
LC-MS (Method 14): R$_t$=1.17 min. ES⁺: m/z=400 [M+H]⁺, ES⁻: 398 [M−H]⁻.
¹H-NMR (DMSO, 300 MHz): δ=9.5-8.9 (br, 2H), 8.62 (d, J=5.1 Hz, 1H), 8.61 (s, 1H), 7.97 (d, J=7.8H, 1H), 7.61 (dd, J=5.1, 7.8 Hz, 1H), 7.41-7.28 (m, 6H), 5.13 (d, J=12.5 Hz, 1H), 5.00 (d, J=12.5 Hz, 1H), 4.29 (dd, J=5.0, 8.8 Hz, 1H), 3.81 (m, 1H), 3.39 (dd, J=4.8, 14.2 Hz, 1H), 3.16 (dd, J=9.0, 14.2 Hz, 1H), 3.12 (br.d, J=12.4 Hz, 1H), 2.97 (dd, J=9.6, 12.4 Hz, 1H), 1.59 (m, 1H), 1.39 (ddd, J=4.9, 9.5, 13.6 Hz, 1H), 1.23 (ddd, J=4.7, 8.9, 13.6 Hz, 1H), 0.89 (d, J=6.6 Hz, 3H), 0.86 (d, J=6.3 Hz, 3H).

Example 41A

N-[(2S)-2-Benzyloxycarbonylamino-4-methylpentyl]-β-(3-pyridyl)alanine bishydrotrifluoroacetate (Z-L-Leu(ΨCH₂NH)-L-β-(3-pyridyl)-Ala-OH)2 TFA

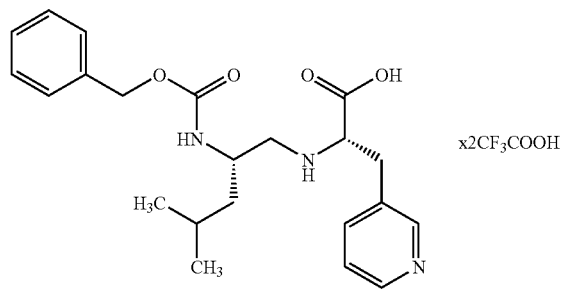

Preparation from Example 28A. Yield: 420 mg (74% of th.).
LC-MS (Method 14): R$_t$=1.15 min.
MS: ES⁺: m/z=400 [M+H]⁺, ES⁻: 398 [M−H]⁻.

¹H-NMR (DMSO, 300 MHz): δ=9.5-8.6 (br, 1H), 8.62 (br.s, 2H), 7.97 (d, J=7.9H, 1H), 7.61 (dd, J=5.2, 7.6 Hz, 1H), 7.43-7.27 (m, 6H), 5.10 (d, J=12.5 Hz, 1H), 5.02 (d, J=12.5 Hz, 1H), 4.32 (dd, J=5.0, 8.4 Hz, 1H), 3.89 (m, 1H), 3.16 (dd, J=4.8, 14.2 Hz, 1H), 3.18 (dd, J=8.9, 14.2 Hz, 1H), 3.14-2.98 (m, 2H), 1.59 (m, 1H), 1.39 (ddd, J=4.9, 8.7, 13.8 Hz, 1H), 1.26 (ddd, J=4.7, 8.8, 13.8 Hz, 1H), 0.89 (d, J=6.6 Hz, 3H), 0.86 (d, J=6.3 Hz, 3H).

Example 42A

N-[(2S)-2-tert-Butoxycarbonylamino-4,4-dimethylpentyl]-β-(3-pyridyl)alanine bishydrotrifluoroacetate (Boc-L-β-tBu-Ala(ΨCH₂NH)-L-β-(3-pyridyl)-Ala-OH)2 TFA

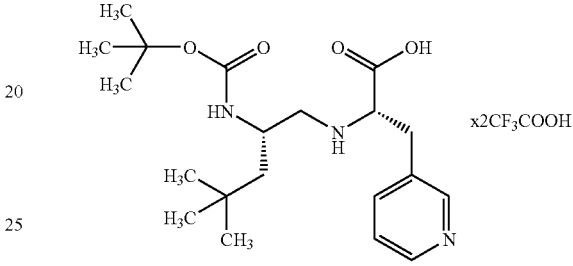

Preparation from Example 29A. Yield: 128 mg (77% of th.).
HPLC (Method 15): R$_t$=3.9 min.
MS: ES⁺: m/z=380 [M+H]⁺ (100), 324(85), 280 (88).
¹H-NMR (DMSO, 300 MHz): o=9.4-8.3 (br, 1H), 8.59 (d, J=ca. 5 Hz, 1H), 8.58 (s, 1H), 7.93 (d, J=7.8H, 1H), 7.56 (dd, J=5.1, 7.8 Hz, 1H), 6.89 (d, J=8.9 Hz, 1H), 4.31 (m, 1H), 3.86 (m, 1H), 3.34 (dd, J=4.9, 14.1 Hz, 1H), 3.34 (dd, J=8.9, 14.1 Hz, 1H), 3.10-2.90 (m, 2H), 1.44 (dd, J=8.9, 14.4 Hz, 1H), 1.39 (s, 9H), 1.32 (dd, J=2.5, 14.4 Hz, 1H), 0.90 (s, 9H).

Example 43A

N-[(2S)-2-Benzyloxycarbonylamino-4-methylpentyl]-β-(3,4-dimethoxyphenyl)alanine hydrotrifluoroacetate (Z-L-Leu-(ΨCH₂NH)-L-β-(3,4-dimethoxyphenyl)-Ala-OH) TFA

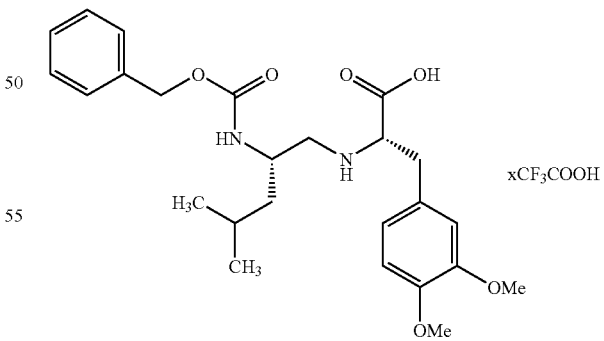

Preparation from Example 30A. Yield 140 mg (72% of th.).
LC-MS (Method 17): R$_t$=1.91 min. ES⁺: m/z=459 [M+H]⁺, ES⁻: 457 [M−H]⁻.
¹H-NMR (DMSO, 400 MHz): δ=9.3-8.4 (br, 2H), 7.41-7.29 (m, 5H), 7.26 (d, J=8.7 Hz, 1H), 6.88 (d, J=8.2 Hz, 1H), 6.87 (s, 1H), 6.75 (d, J=8.2 Hz, 1H), 5.08 (d, J=11.0 Hz, 1H), 5.00 (d, J=11.0 Hz, 1H), 4.11 (m, 1H), 3.82 (m, 1H), 3.76 (s, 3H), 3.72 (s, 3H), 3.12 (dd, J=5.2, 14.1 Hz, 1H), 3.02 (dd, J=7.5, 14.1 Hz, 1H), 3.0-2.83 (m, 2H), 1.55 (m, 1H), 1.34 (ddd, J=4.9, 9.8, 13.9 Hz, 1H), 1.21 (ddd, J=4.4, 8.5, 13.6 Hz, 1H), 0.87 (d, J=6.6 Hz, 3H), 0.84 (d, J=6.4 Hz, 3H).

Example 44A

N-[(2R)-2-Benzyloxycarbonylamino-4-methylpentyl]-β-(3,4-dimethoxyphenyl)alanine hydrotrifluoroacetate (Z-D-Leu-(ΨCH₂NH)-L-β-(3,4-dimethoxyphenyl)-Ala-OH) TFA

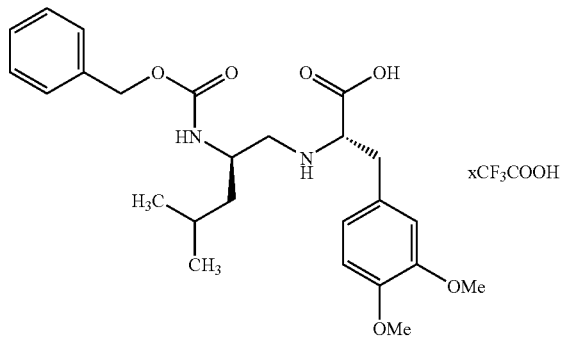

Preparation from Example 31A. Yield 126 mg (99% of th.).

LC-MS (Method 17): R$_t$=1.92 min. ES⁺: m/z=459 [M+H]⁺, ES⁻: 457 [M−H]⁻.

¹H-NMR (DMSO, 400 MHz): δ=9.4-8.4 (br, 2H), 7.41-7.29 (m, 5H), 7.27 (d, J=8.7 Hz, 1H), 6.88 (d, J=8.0 Hz, 1H), 6.86 (s, 1H), 6.75 (d, J=8.0 Hz, 1H), 5.11 (d, J=12.3 Hz, 1H), 5.00 (d, J=12.3 Hz, 1H), 4.09 (m, 1H), 3.88 (m, 1H), 3.74 (s, 3H), 3.72 (s, 3H), 3.15 (dd, J=4.9, 13.6 Hz, 1H), 2.99 (dd, J=7.9, 14.1 Hz, 1H), 2.97 (br.d, J=ca. 12 Hz, 1H), 2.87 (dd, J=9.7, 11.8 Hz, 1H), 1.55 (m, 1H), 1.35 (ddd, J=4.9, 9.8, 13.9 Hz, 1H), 1.21 (ddd, J=4.9, 8.5, 13.6 Hz, 1H), 0.87 (d, J=7.8 Hz, 3H), 0.83 (d, J=7.9 Hz, 3H).

Example 45A

N-[(2R)-2-tert-Butoxycarbonylamino-3-trimethylsilylpropyl]-β-(3-pyridyl)alanine hydrotrifluoroacetate (Boc-L-β-Trimethylsilyl-Ala(ΨCH₂NH)-L-β-(3-pyridyl)-Ala-OH) TFA

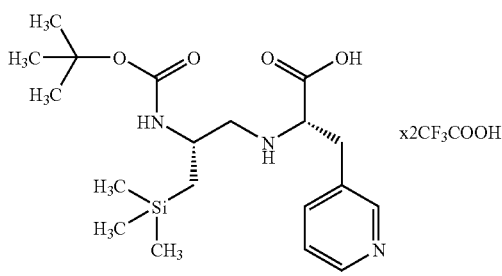

Preparation from Example 32A. Yield 56 mg (20% of th.).

LC-MS (Method 17): R$_t$=1.55 min. ES⁺: m/z=396 [M+H]⁺, ES⁻: 394 [M−H]⁻.

¹H-NMR (CDCl₃, 400 MHz) (main rotamer): δ=9.10 (s, 1H), 8.68-8.58 (m, 2H), 7.81 (t, J=6.6 Hz, 1H), 5.19 (br.d, J=ca. 6 Hz, 1H), 4.19 (m, 1H), 3.99 (m, 1H), 3.71-3.57 (m, 2H), 3.30-3.13 (m, 2H), 1.42 (s, 9H), 0.90 (dd, J=10.8, 14.8 Hz, 1H), 0.75 (dd, J=4.4, 15 Hz, 1H), 0.03 (s, 9H).

Example 46A

N-[(2R)-2-Benzyloxycarbonylamino-3-trimethylsilylpropyl]-β-tert-butylalanine hydrotrifluoroacetate (Z-L-β-Trimethylsilyl-Ala(ΨCH₂NH)-L-β-tBu-Ala-OH) TFA

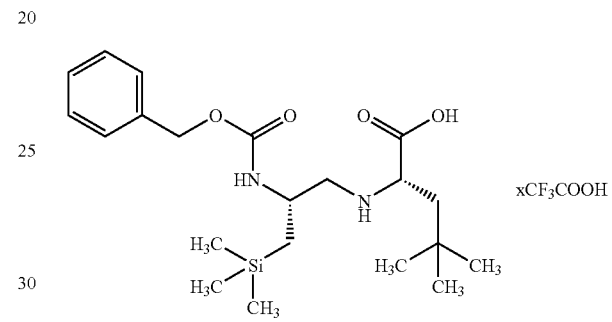

Preparation from Example 34A. Yield: 33 mg (47% of th.).

HPLC (Method 15): R$_t$=4.6 min.;

MS (ESI pos): m/z (%)=409 (100) [M+H]⁺, ESI neg.: 407 (10) [M−H]⁻.

¹H-NMR (DMSO, 300 MHz): δ=7.56-7.43 (m, 5H), 7.29 (d, J=9.0 Hz, 1H), 5.13 (d, J=12 Hz, 1H), 5.01 (d, J=12 Hz, 1H), 4.03-3.80 (m, 2H), 3.10 (m, 1H), 2.88 (m, 1H), 1.84 (dd, J=9.0, 14.5 Hz, 1H), 1.68 (br.d, J=14.5 Hz, 1H), 0.95 (s, 9H), 0.82 (m, 2H), 0.03 (s, 9H).

Example 47A

N-[(2S)-2-Benzyloxycarbonylamino-4,4-dimethylpentyl]-β-trimethylsilylalanine hydrotrifluoroacetate (Z-L-β-t-Butyl-Ala(ΨCH₂NH)-L-β-(trimethylsilyl)-Ala-OH) TFA

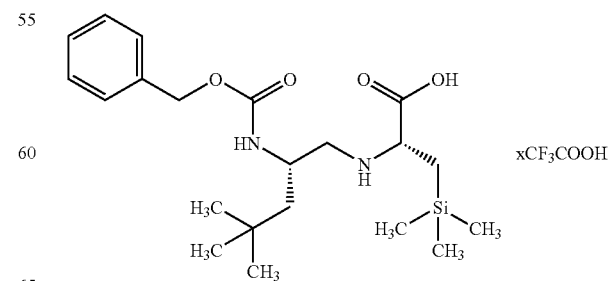

Preparation from Example 35A. Yield: 86 mg (88% of th.).
HPLC (Method 15): $R_t$=4.6 min.

MS: $ES^+$: m/z=409 (100) $[M+H]^+$; $ES^-$: 407 (9) $[M-H]^-$, 113 (100).

$^1$H-NMR (DMSO, 300 MHz): δ=9.00-8.65 (br., 2H), 7.42-7.25 (m, 5H), 7.28 (d, J=9.1 Hz, 1H), 5.13 (d, J=12.6 Hz, 1H), 4.99 (d, J=12.6 Hz, 1H), 3.95-3.80 (m, 2H), 3.10 (m, 1H), 2.89 (m, 1H), 1.44 (dd, J=10.3, 14.3 Hz, 1H), 1.35 (br.d, J=14.3 Hz, 1H), 1.21 (dd, J=3.9, 14.0 Hz, 1H), 0.88 (s, 9H), 0.07 (s, 9H).

Example 48A

N-[(2R)-2-Benzyloxycarbonylamino-3-trimethylsilylpropyl]-β-trimethylsilylalanine hydrotrifluoroacetate (Z-L-β-Trimethylsilyl-Ala(ΨCH$_2$NH)-L-β-(trimethylsilyl)-Ala-OH) TFA

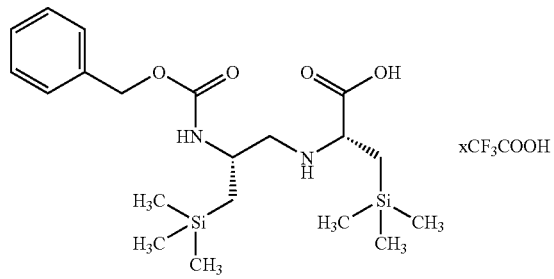

Preparation from Example 36A. Yield 43 mg (82% of th.).
LC-MS (Method 16): $R_t$=2.15 min. $ES^+$: m/z=425 $[M+H]^+$, $ES^-$: 423 $[M-H]^-$.

$^1$H-NMR (DMSO, 300 MHz): δ 9.00-8.55 (br.s, 2H), 7.39-7.22 (m, 5H), 7.25 (d, J=10.2 Hz, 1H), 5.10 (d, J=12.3 Hz, 1H), 4.98 (d, J=12.3 Hz, 1H), 4.00-3.82 (m, 2H), 3.01 (m, 1H), 2.89 (m, 1H), 1.20 (dd, J=3.9, 14.1 Hz, 1H), 1.03 (t, J=13.3 Hz, 1H), 0.89-0.75 (m, 2H), 0.10 (s, 9H), 0.05 (s, 9H).

Example 49A

N-[(2S)-2-Benzyloxycarbonylamino-4,4-dimethylpentyl]-$O^5$-tert-butylaspartic acid hydrotrifluoroacetate (Z-L-β-tBu-Ala(ΨCH$_2$NH)-L-Asp(tBu)-OH) TFA

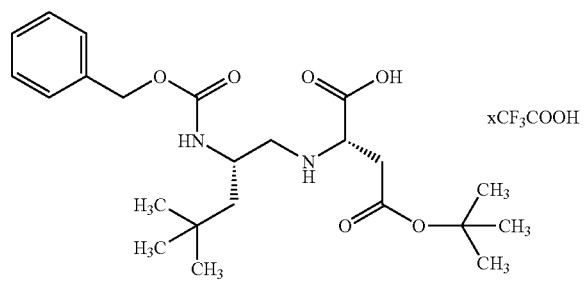

Preparation from Example 37A. Yield 78 mg (42% of th.).
HPLC (Method 15): $R_t$=4.5 min.

MS: $ES^+$: m/z=437 (100) $[M+H]^+$, $ES^-$: 435 (12) $[M-H]^-$.

$^1$H-NMR (DMSO, 300 MHz): δ=9.5-8.0 (br., 2H), 7.39-7.27 (m, 6H), 5.10 (d, J=12.6 Hz, 1H), 4.99 (d, J=12.6 Hz, 1H), 4.12 (br.s, 1H), 3.94-3.83 (m, 1H), 3.00-2.82 (m, 2H), 2.82 (d, =5.6 Hz, 2H), 1.43 (m, 1H), 1.41 (s, 9H), 1.30 (dd, J=2.7, 14.2 Hz, 1H), 0.89 (s, 9H).

The following Example 50A is prepared according to General working procedure 5:

Example 50A

N-[(2R)-2-tert-Butoxycarbonylamino-3-trimethylsilylpropyl]leucine hydrotrifluoroacetate (Boc-L-β-Trimethylsilyl-Ala(ΨCH$_2$NH)-L-Leu-OH) TFA

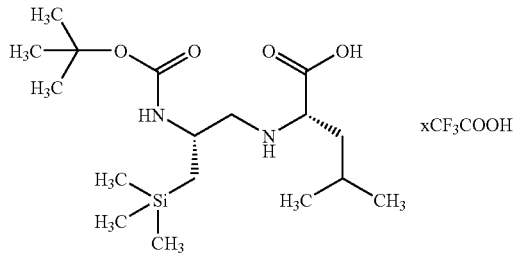

Preparation from Example 33A. Yield 155 mg (95% of th.).
MS (DCI/NH$_3$): m/z=361 (100) $[M+H]^+$, 315 (85).

$^1$H-NMR (DMSO, 300 MHz): δ=9.1-8.5 (br, 2H), 6.85 (d, J=9.0, 1H), 3.98-3.82 (m, 2H), 3.00 (dd, 7.6, 12.3 Hz, 1H), 2.87 (dd, J=5.3, 12.3 Hz, 1H), 1.85-1.60 (m, 3H), 1.40 (s, 9H), 0.95 (d, J=ca. 2 Hz, 3H), 0.93 (d, J=ca. 2 Hz, 3H), 0.85-0.78 (m, 2H), 0.03 (s, 9H).

Reductive Amination of Aminoaldehydes and Example 3A

Examples 51A to 54A are prepared from Example 3A according to General working procedure 3. The yield is not determined at this stage, but only after the removal of the N-terminal protecting group.

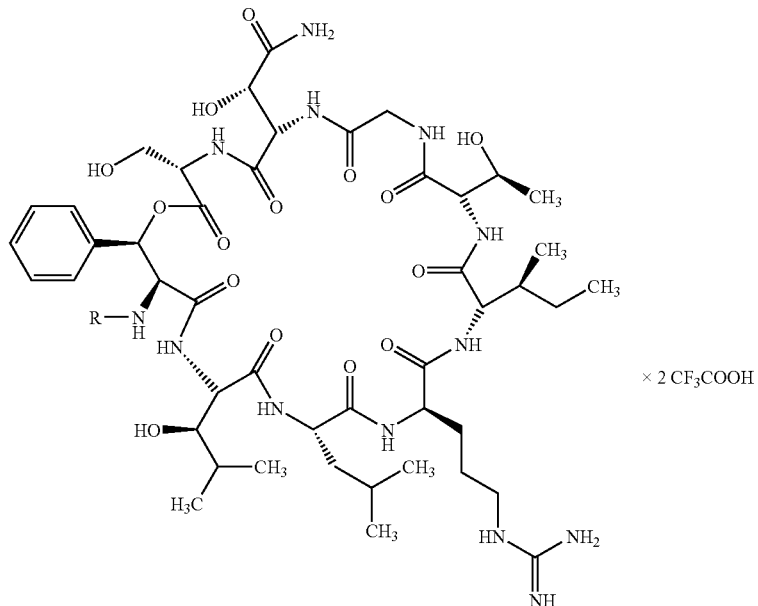

| Ex. No. | Name | R | Starting compounds/ analysis |
|---|---|---|---|
| 51A | N-[(2S)-2-tert-Butoxycarbonylamino-4-methylpent-1-yl]de(1-D-leucine)-lysobactin bis-hydrotrifluoroacetate | 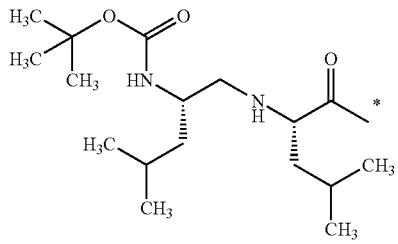 | from Example 3A and Boc-Leu-H. HPLC (Method 15): $R_t$ = 4.52 min. LC/MS: (Method 17): $R_t$ = 2.42 min.; ES$^+$: 1363 [M + H]$^+$, 682 [M + 2H]$^{2+}$; ES$^-$: 1361 [M − H]$^-$. |
| 52A | N-[(2S)-2-tert-Butoxycarbonylamino-4,4-dimethylpent-1-yl]de(1-D-leucine)-lysobactin bis-hydrotrifluoroacetate | 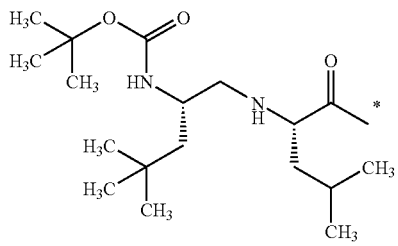 | from Example 3A and Example 20A. HPLC (Method 15): $R_t$ = 4.44 min. LC/MS: (Method 17): $R_t$ = 1.86 min.; ES$^+$: 1377 [M + H]$^+$, 689.4 [M + 2H]$^{2+}$; ES$^-$: 1375 [M − H]$^-$. HR-MS: [M + H]$^+$ found: 1376.8138 calc.: 1376.8153 |

-continued

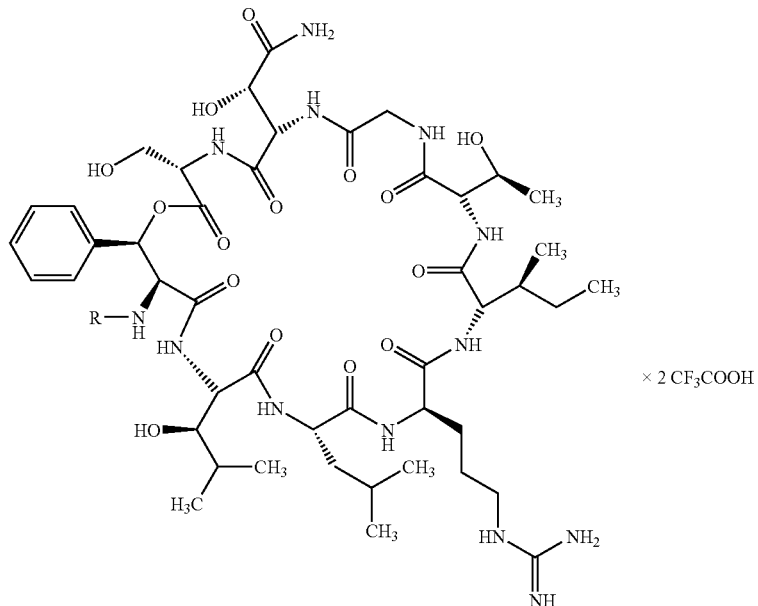

× 2 CF₃COOH

| Ex. No. | Name | R | Starting compounds/ analysis |
|---|---|---|---|
| 53A | N-[(2R)-2-tert-Butoxycarbonylamino-4,4-dimethylpent-1-yl-]de(1-D-leucine)-lysobactin bis-hydrotrifluoroacetate | | from Example 3A and Example 21A. HPLC (Method 15): $R_t$ = 4.42 min. LC/MS: (Method 17): $R_t$ = 1.85 min.; ES$^+$: 1377 [M + H]$^+$; 689.4 [M + 2H]$^{2+}$; ES$^-$: 1375 [M − H]$^-$. HR-MS: [M + H]$^+$ found: 1376.8147 calc.: 1376.8153 |
| 54A | N-[(2R)-2-Benzoylcarbonyl-amino-4-methylpent-1-yl]de(1-D-leucine)-lysobactin bis-hydrotrifluoroacetate | | from Example 3A and Example 19A. HPLC (Method 15): $R_t$ = 3.88 min. LC/MS: (Method 17): $R_t$ = 1.93 min.; ES$^+$: 1397 [M + H]$^+$; ES$^-$: 1395 [M − H]$^-$ |

Coupling of the Deoxodipeptidic Acid to Example 5A

The following Examples 55A to 67A are prepared from Example 5A according to General working procedure 6. The yield is not determined at this stage, but only after the removal of the N-terminal protecting group.

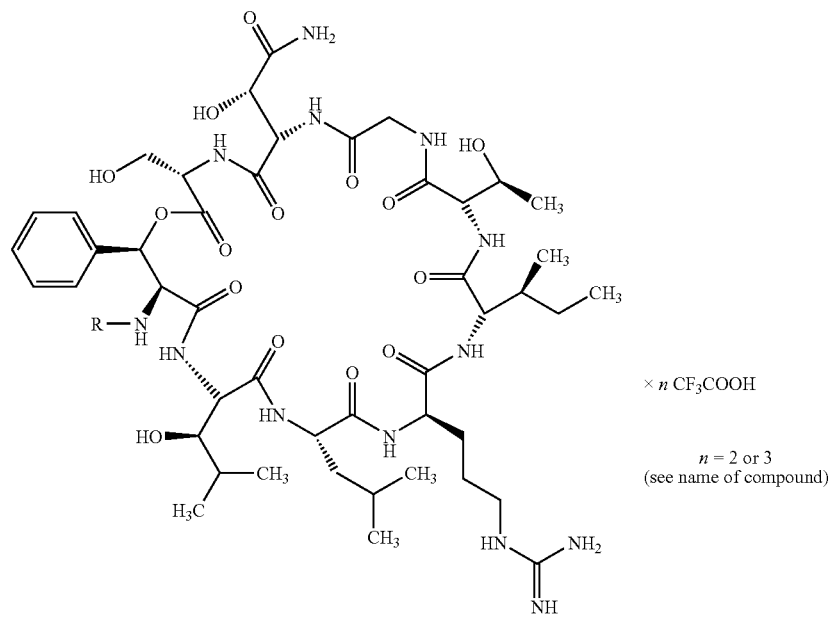

$\times\, n\ CF_3COOH$ $n = 2$ or $3$
(see name of compound)

| Ex. No. | Name | R | Starting compounds/ analysis |
|---|---|---|---|
| 55A | N-{N-[(2S)-2-tert-Butoxycarbonylamino-4,4-dimethylpent-1-yl]-(β-3-pyridyl-Ala)}-de(1-D-leucine-2-leucine)lysobactin tris-hydrotrifluoroacetate | | from Example 5A and Example 42A. HPLC (Method 19): $R_t$ = 3.67 min. LC/MS: (Method 17): $R_t$ = 1.78 min.; ES$^+$: 706.9 [M + 2H]$^{2+}$; ES$^-$: 1410 [M − H]$^-$ |
| 56A | N-{N-[(2R)-2-tert-Butoxycarbonylamino-3-trimethylsilylprop-1-yl]}de(1-D-leucine-lysobactin bis-hydrotrifluoroacetate | | from Example 5A and Example 50A. LC/MS (Method 17): $R_t$ = 1.95 min. ES$^+$: 1393 [M + H]$^+$, 697.3 [M + 2H]$^{2+}$; ES$^-$: 1391 [M − H]$^-$ |
| 57A | N-{N-[(2R)-2-tert-Butoxycarbonylamino-3-trimethylsilylprop-1-yl]-(β-(3-pyridyl)-Ala)}-de(1-D-leucine-2-leucine)lysobactin tris-hydrotrifluoroacetate | | from Example 5A and Example 45A. HPLC (Method 19): $R_t$ = 3.72 min. (not characterized, directly reated further to give Example 6) |

-continued

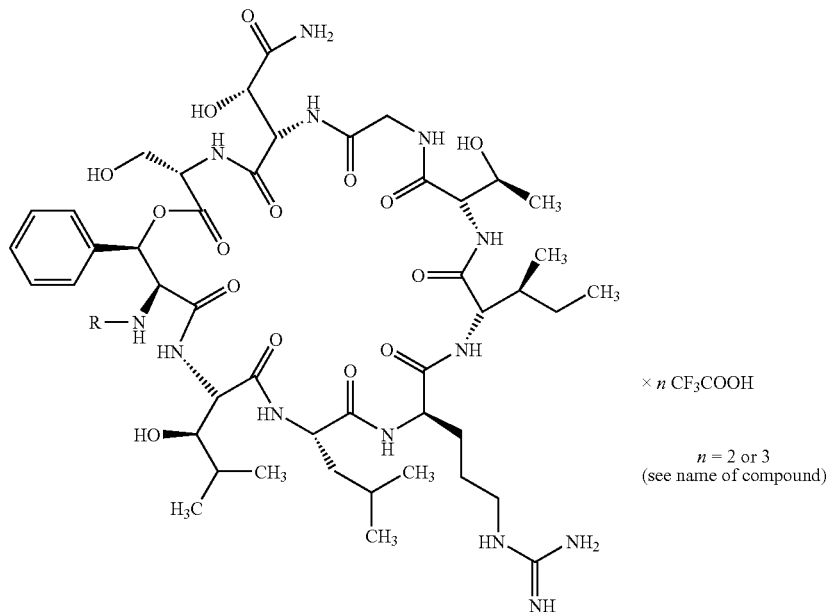

× n CF₃COOH n = 2 or 3
(see name of compound)

| Ex. No. | Name | R | Starting compounds/ analysis |
|---|---|---|---|
| 58A | N-{N-[(2S)-2-Benzyl-oxycarbonylamino-4,4-dimethylpent-1-yl]-β-tBu-Ala} de(1-D-leucine-2-leucine)-lysobactin bis-hydrotrifluoroacetate | [structure] | from Example 5A and Example 39A. HPLC (Method 19): $R_t$ = 3.91 min. LC/MS: (Method 17): $R_t$ = 1.96 min.; ES⁺: 713.4 [M + H]⁺; ES⁻: 1423 [M − H]⁻. |
| 59A | N-{N-[(2R)-2-Benzyl-oxycarbonylamino-4,4-dimethylpent-1-yl]-β-tBu-Ala}-de(1-D-leucine-2-leucine)-lysobactin bis-hydrotrifluoroacetate | [structure] | from Example 5A and Example 38A. LC/MS: (Method 17): $R_t$ = 2.01 min.; ES⁺: 713.2 [M + 2H]²⁺; ES⁻: 1423 [M − H]⁻. |

-continued

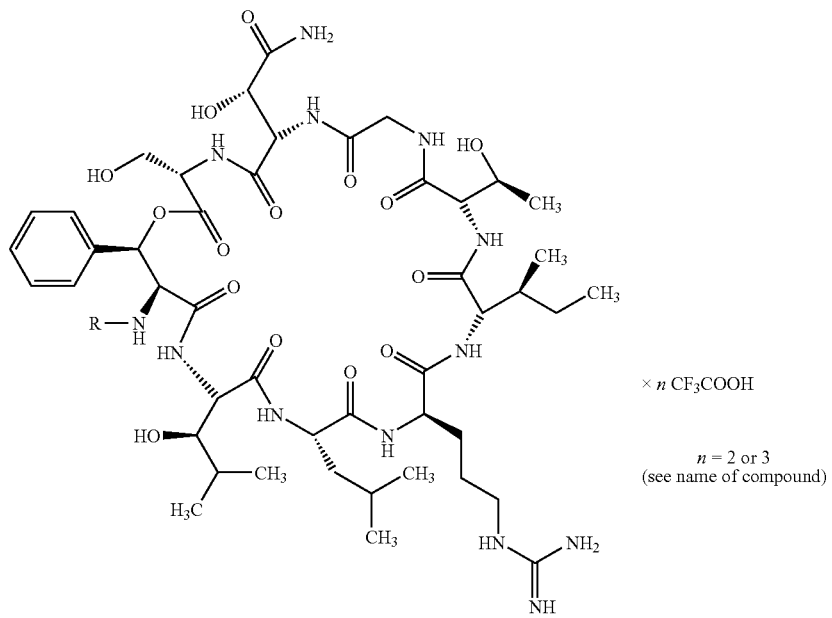

× n CF$_3$COOH n = 2 or 3
(see name of compound)

| Ex. No. | Name | R | Starting compounds/ analysis |
|---|---|---|---|
| 60A | N-{N-[(2S)-2-Benzyl-oxycarbonylamino-4-methylpent-1-yl]-[β-(3,4-dimethoxyphenyl)-Ala)]}-de(1-D-leucine-2-leucine)lysobactin bishydrotrifluoro-acetate | | from Example 5A and Example 43A. LC/MS: (Method 17): R$_t$ = 1.96 min.; ES$^+$: 746.4 [M + 2H]$^{2+}$; ES$^-$: 1490 [M − H]$^-$. |
| 61A | N-{N-[(2R)-2-Benzyl-oxycarbonylamino-4-methylpent-1-yl]-[β-(3,4-dimethoxyphenyl)-Ala)]}-de(1-D-leucine-2-leucine)lysobactin bishydrotrifluoro-acetate | | from Example 5A and Example 44A. LC/MS: (Method 17): R$_t$ = 1.95 min.; ES$^+$: 746.4 [M + 2H]$^{2+}$; ES$^-$: 1490 [M − H]$^-$. |

-continued

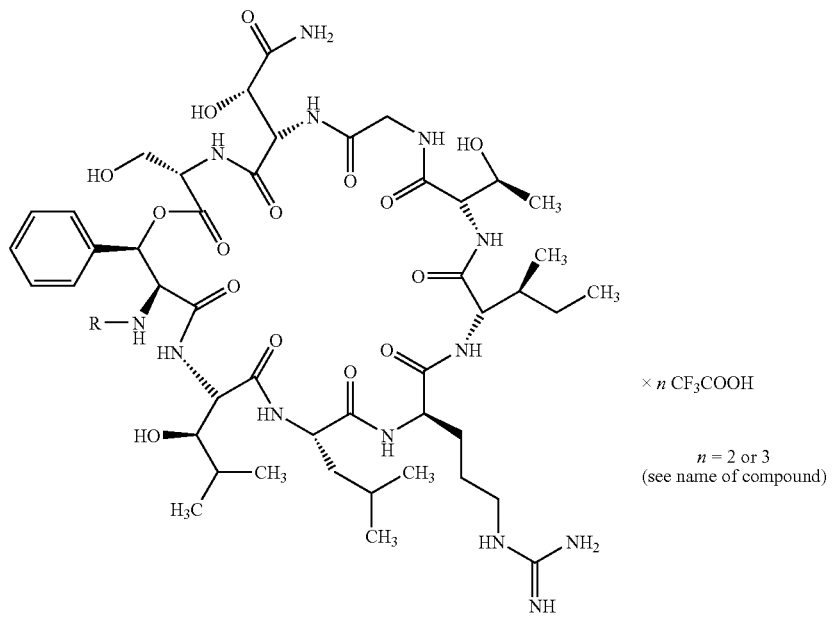

× n CF₃COOH n = 2 or 3
(see name of compound)

| Ex. No. | Name | R | Starting compounds/ analysis |
|---|---|---|---|
| 62A | N-{N-[(2S)-2-Benzyl-oxycarbonylamino-4-methylpent-1-yl]-[β-(3-pyridyl)-Ala]} de(1-D-leucine-2-leucine)-lysobactin tris-hydrotrifluoroacetate | | from Example 5A and Example 41A. HPLC (Method 19): $R_t$ = 3.63 min. LC/MS: (Method 17): $R_t$ = 1.74 min.; ES⁺: 716.8 $[M + 2H]^{2+}$; ES⁻: 1430 $[M - H]^-$. |
| 63A | N-{N-[(2R)-2-Benzyl-oxycarbonylamino-4-methylpent-1-yl]-(β-3-pyridyl-Ala)} de(1-D-leucine-2-leucine)-lysobactin tris-hydrotrifluoroacetate | | from Example 5A and Example 40A. HPLC (Method 19): $R_t$ = 3.63 min. LC/MS: (Method 17): $R_t$ = 1.67 min.; ES⁺: 716.7 $[M + 2H]^{2+}$; ES⁻: 1430 $[M - H]^-$. |

-continued

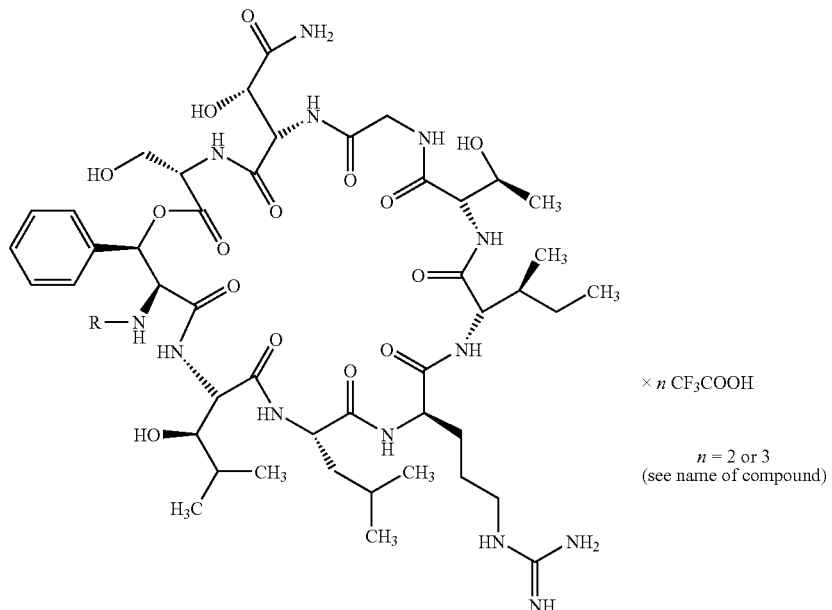

× n CF₃COOH n = 2 or 3
(see name of compound)

| Ex. No. | Name | R | Starting compounds/ analysis |
|---|---|---|---|
| 64A | N-{N-[(2R)-2-Benzyl-oxycarbonylamino-3-trimethylsilylprop-1-yl]-(β-trimethylsilyl-Ala)}de(1-D-leucine-2-leucine)lysobactin bishydrotrifluoro-acetate | [structure shown] | from Example 5A and Example 48A. LC/MS: (Method 14): $R_t$ = 1.95 min.; ES⁺: 1458 [M + H]⁺, 729.4 [M + 2H]²⁺; ES⁻: 1456 [M − H]⁻. |
| 65A | N-{N-[(2R)-2-Benzyl-oxycarbonylamino-3-trimethylsilylprop-1-yl]-(β-tBu-Ala)}de(1-D-leucine)-2-leucine)-lysobactin bis-hydrotrifluoroacetate | [structure shown] | from Example 5A and Example 46A. LC/MS: (Method 17): $R_t$ = 1.90 min.; ES⁺: 1441 [M + 2H]²⁺, 721.3 [M + 2H]²⁺; ES⁻: 1439 [M − H]⁻. |

-continued

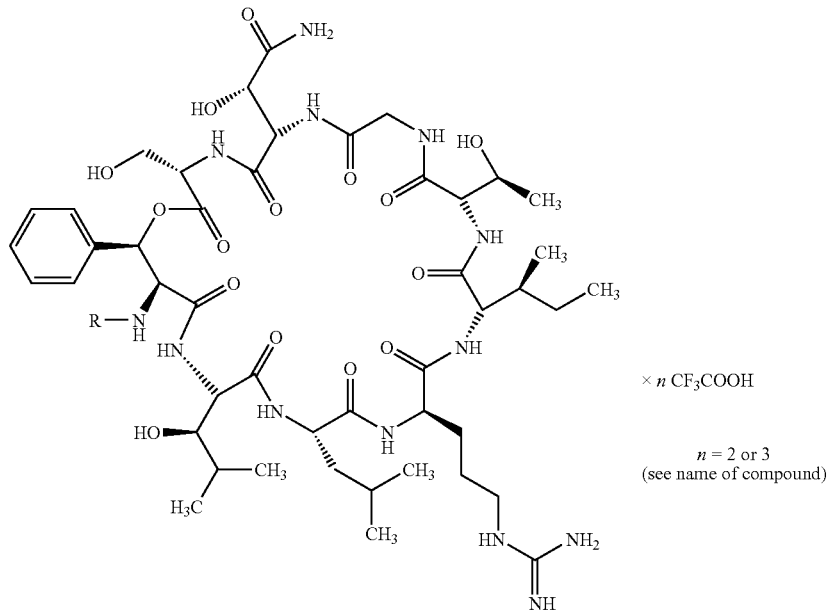

× n CF₃COOH n = 2 or 3
(see name of compound)

| Ex. No. | Name | R | Starting compounds/ analysis |
|---|---|---|---|
| 66A | N-{N-[(2S)-2-Benzyl-oxycarbonylamino-4,4-dimethylpent-1-yl]-(β-trimethylsilyl-Ala)}-de(1-D-leucine-2-leucine)lysobactin bis-hydrotrifluoroacetate | | from Example 5A and Example 47A. LC/MS: (Method 17): $R_t$ = 1.96 min.; ES⁺: 1441 [M + H]⁺, 721.2 [M + 2H]²⁺; ES⁻: 1439 [M − H]⁻. |
| 67A | N-{N-[(2S)-2-Benzyl-oxycarbonylamino-4,4-dimethylpent-1-yl]-Asp(tBu)de(1-D-leucine-2-leucine)-lysobactin bis-hydrotrifluoroacetate | | from Example 5A and Example 49A. LC/MS: (Method 17): $R_t$ = 2.13 min.; ES⁺: 1469 [M + H]⁺, 735.3 [M + 2H]²⁺; ES⁻: 1467 [M − H]⁻. |

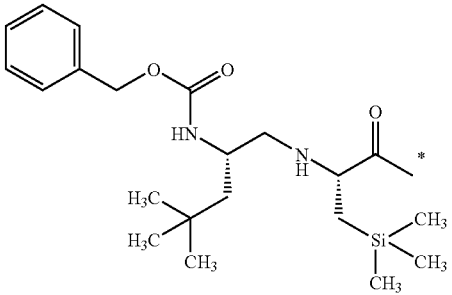

Example 68A (2R,3S)-3-Benzyloxycarbonylamino-5,5-dimethyl-2-hydroxyhexane

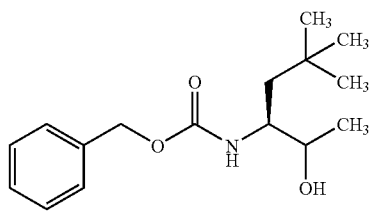

A solution of 180 mg (0.68 mmol) of the compound of Example 16A in 1 ml of anhydrous diethyl ether is added dropwise to 635 µl (0.89 mmol of a solution of methylmagnesium bromide (1.4N in toluene:THF 3:1) under argon at RT. The reaction mixture is then heated for 2 h in a warm oil bath (50° C.), cooled and quenched with an ice cube. The mixture is acidified with 1N hydrochloric acid and extracted three times with ethyl acetate. The combined organic phases are dried over sodium sulfate and concentrated on a Rotavapor. The residue is purified by preparative HPLC (Method 25). 50 mg (20% of th.) of the title compound are obtained.

LC-MS (Method 17): $R_t$=2.34 min. MS (ES$^+$): m/z=280.3 [M+H]$^+$.

Example 69A (3S)-3-Benzyloxycarbonylamino-5,5-dimethyl-2-oxohexane

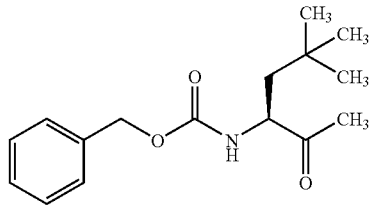

Pyridine-SO$_3$ complex (285 mg, 1.79 mmol) is added to a solution of the compound of Example 68A (50 mg, 0.18 mmol) and N,N-diisopropylethylamine (310 µl, 1.79 mmol) in 2 ml of DMSO at 10° C. with and the mixture is slowly warmed to RT. After 2 h, 50 ml of ice/water are added to the reaction mixture. The mixture is extracted four times with diethyl ether. The combined organic phases are washed three times with a 10% citric acid solution, then three times with water and twice with a satd. sodium chloride solution, dried over magnesium sulfate and concentrated at 20° C. on a Rotavapor. The crude product (30 mg, 60% of th.) is reacted further without additional purification.

LC-MS (Method 14): $R_t$=2.26 min. MS (ES$^+$): m/z=278.4 [M+H]$^+$.

$^1$H-NMR (CDCl$_3$, 300 MHz): δ=7.40-7.28 (m, 5H), 5.15-5.06 (m, 3H), 4.40 (dt, J=2.3, 9.1 Hz, 1H), 2.21 (s, 3H), 1.68 (dd, J=2.3, 14.7 Hz, 1H), 1.24 (dd, J=9.1, 14.7 Hz, 1H), 0.99 (s, 9H).

Example 70A

N-{(2R,3S)-2-{[(Benzyloxy)carbonyl]amino}-5,5-dimethylhex-2-yl}-4-methyl-L-leucine methyl ester (Z-L-β-tert-Butyl-Ala(ΨCHMeNH)-L-β-tert-butyl-Ala-OMe)

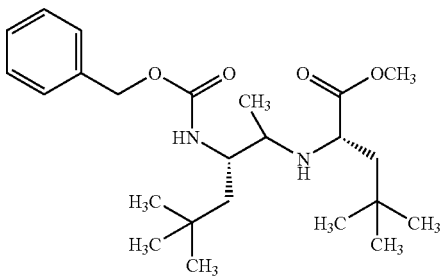

The title compound is prepared from the compound of Example 69A (27 mg) and the compound of Example 24A (29 mg) according to General working procedure 3. Yield 6 mg (13% of th.).

LC-MS (Method 17): $R_t$=2.29 min. MS (ES$^+$): m/z=421.2 [M+H]$^+$.

Example 71A

N-{(2R,3S)-2-{[(Benzyloxy)carbonyl]amino}-5,5-dimethylhex-2-yl}-4-methyl-L-leucine (Z-L-β-tert-Butyl-Ala(ΨCHMeNH)-L-β-tert-butyl-Ala-OH)

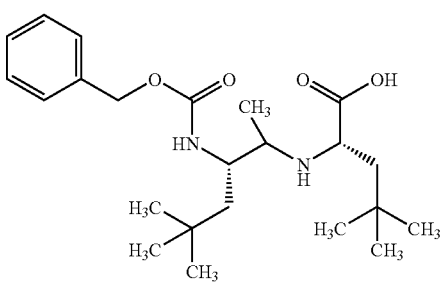

The title compound is prepared from the compound of Example 70A (6 mg) according to General working procedure 4. Yield 3 mg (50% of th.). The analytical data indicate a diastereomer.

LC-MS (Method 17): $R_t$=2.11 min. MS (ES$^+$): m/z=407.3 [M+H]$^+$, (ES$^-$): m/z=405.2 [M–H]$^-$.

$^1$H-NMR (DMSO-d$_6$, 400 MHz): δ=7.38-7.25 (m, 5H), 7.20 (d, J=9.1 Hz, 1H), 5.04 and 4.98 (in each case d, [AB system], J=12.7, in each case 1H), 3.51 (m, 1H), 3.18 (t, J=6.2 Hz, 1H), 2.53 (m, 1H), 2.50 (s, 3H), 1.51 (dd, J=3.6, 13.9 Hz, 1H), 1.34-1.23 (m, 3H), 0.92 (s, 9H), ca. 0.9 (3H), 0.84 (s, 9H).

Exemplary Embodiments

Examples 1 to 6 are prepared according to General working procedure 7:

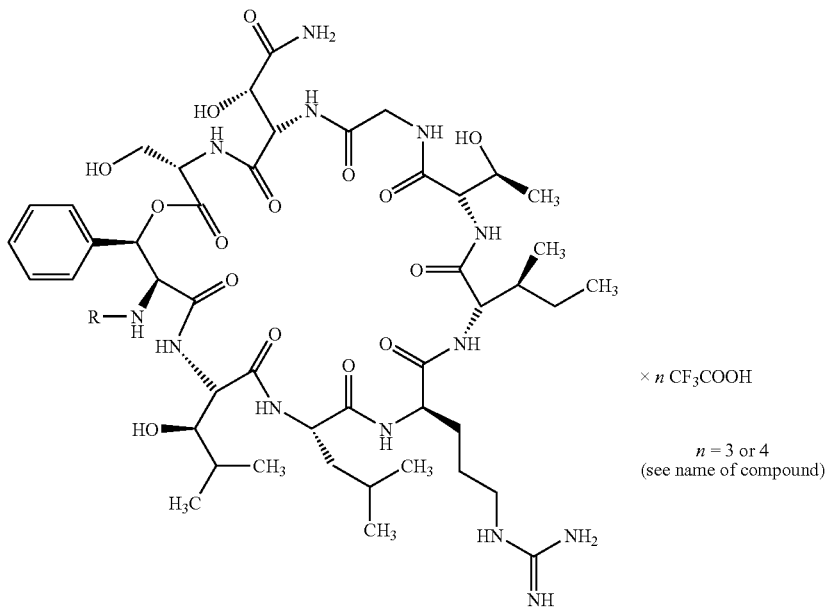

× n CF₃COOH n = 3 or 4
(see name of compound)

| Ex. No. | Name | R | Yield/analysis (Yield starting from Example 3A and 5A) |
|---|---|---|---|
| 1 | N-[(2S)-2-Amino-4-methylpent-1-yl]de(1-D-leucine)lysobactin trishydro-trifluoroacetate | (structure) | from Example 51A; 46.6 mg (17% of th.) HPLC (Method 15): $R_t$ = 3.55 min. LC/MS: (Method 17): $R_t$ = 1.47 min.; ES⁺: 1263 [M + H]⁺; ES⁻: 1261 [M − H]⁻. HR-MS: [M + H]⁺ found: 1262.7522 calc.: 1262.7472 Confirmation by Maldi (Method 20) of the compound treated according to Method 9. |
| 2 | N-[(2S)-2-Amino-4,4-dimethylpent-1-yl]de(1-D-leucine)lysobactin trishydro-trifluoroacetate | (structure) | from Example 52A; 52 mg (29% of th.) HPLC (Method 15): $R_t$ = 3.95 min. LC/MS: (Method 17): $R_t$ = 1.48 min.; ES⁺: 1277 [M + H]⁺; ES⁻: 1275 [M − H]⁻. HR-MS: [M + H]⁺ found: 1276.7631 calc.: 1262.7629 |
| 3 | N-[(2R)-2-Amino-4,4-dimethylpent-1-yl]de(1-D-leucine)lysobactin trishydro-trifluoroacetate | (structure) | from Example 53A; 44 mg (23% of th.) HPLC (Method 15): $R_t$ = 3.87 min. LC/MS: (Method 17): $R_t$ = 1.53 min.; ES⁺: 1277 [M + H]⁺; ES⁻: 1275 [M − H]⁻. HR-MS: [M + H]⁺ found: 1276.7622 calc.: 1262.7629 |

-continued

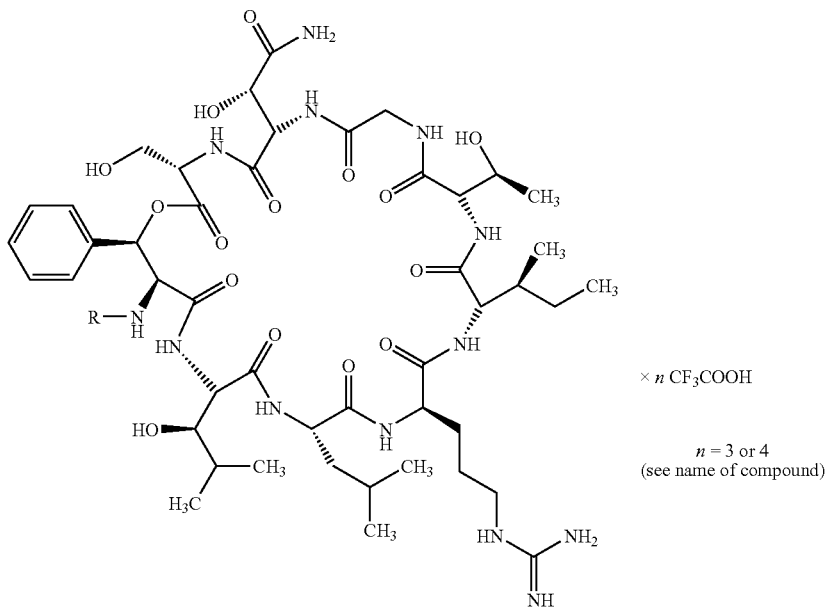

× n CF₃COOH n = 3 or 4
(see name of compound)

| Ex. No. | Name | R | Yield/analysis (Yield starting from Example 3A and 5A) |
|---|---|---|---|
| 4 | N-{N-[(2S)-2-Amino-4,4-di-methylpent-1-yl](β-3-pyridyl-Ala)}de(1-D-leucine-2-leucine)-hydrotrifluoro-acetate | | from Example 55A; 81 mg (43% of th.) HPLC (Method 15): $R_t$ = 3.87 min. LC/MS: (Method 17): $R_t$ = 1.35 min.; ES⁺: 646.8 $[M + 2H]^{2+}$; ES⁻: 1310 $[M − H]^-$. HR-MS: $[M + H]^+$ found: 1311.7446 calc.: 1311.7425 |
| 5 | N-[(2R)-2-Amino-3-trimethylsilyl-prop-1-yl]de(1-D-leucine) lysobactin trishydro-trifluoroacetate | | from Example 56A, 117 mg (34% of th.) HPLC (Method 15): $R_t$ = 3.92 min. LC/MS: (Method 17): $R_t$ = 1.51 min.; ES⁺: 647.3 $[M + 2H]^{2+}$; ES⁻: 1291 $[M − H]^-$ HR-MS: $[M + H]^+$ found: 1292.7382 calc.: 1292.7398 |
| 6 | N-{N-[(2R)-2-Amino-3-trimethylsilyl-prop-1-yl]-(β-(3-pyridyl)-Ala]}de-(1-D-leucine-2-leucine)lysobactin tetrahydro-trifluoroacetate | | from Example 57A, 31 mg (49% of th.) HPLC (Method 15): $R_t$ = 3.98 min. LC/MS: (Method 17): $R_t$ = 1.33 min.; ES⁺: 1328 $[M + H]^+$, 664.7 $[M + 2H]^{2+}$; ES⁻: 1326 $[M − H]^-$. HR-MS: $[M + H]^+$ found: 1327.7228 calc.: 1327.7194 |

Examples 7 to 17 are prepared according to General working procedure 8:

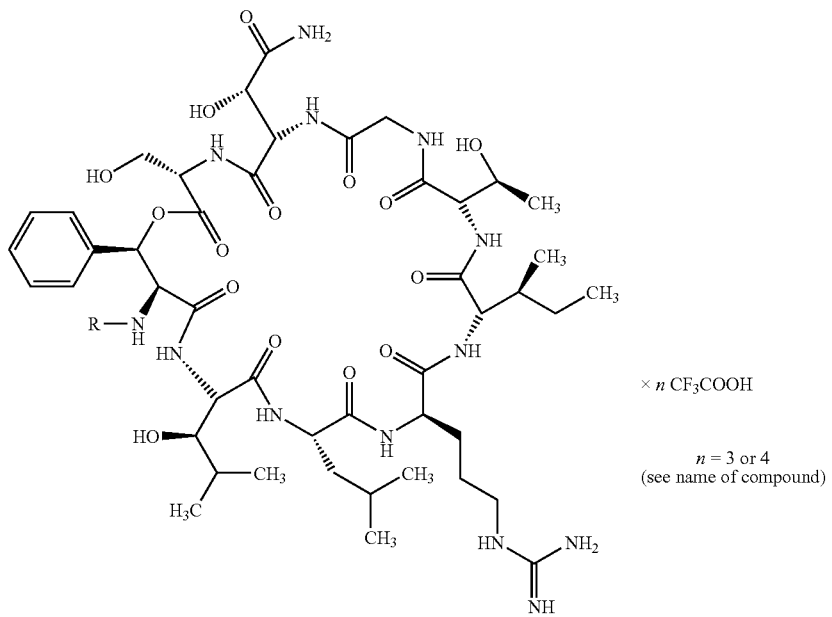

× n CF₃COOH n = 3 or 4
(see name of compound)

| Ex. No. | Name | R | Yield/analysis (Yield starting from Example 3A and 5A) |
|---|---|---|---|
| 7 | N-[(2R)-2-Amino-4-methylpent-1-yl]de(1-D-leucine) lysobactin trishydro-trifluoroacetate | | from Example 54A, 34 mg (16% of th.) HPLC (Method 15): $R_t$ = 3.47 min. LC/MS: (Method 17): $R_t$ = 1.55 min.; ES⁺: 1263 [M + H]⁺; ES⁻: 1261 [M − H]⁻. HR-MS: [M + H]⁺ found: 1262.7479 calc.: 1272.7472 |
| 8 | N-{N-[(2S)-2-Amino-4,4-dimethylpent-1-yl]-β-tBu-Ala-de(1-D-leucine-2-leucine)-lysobactin tris-hydrofluoro-acetate | | from Example 58A, 41 mg (28% of th.) HPLC (Method 15): $R_t$ = 4.00 min. LC/MS: (Method 17): $R_t$ = 1.55 min.; ES⁺: 1291 [M + H]⁺; ES⁻: 1290 [M − H]⁻. HR-MS: [M + H]⁺ found: 1290.7799 calc.: 1290.7785 Confirmation by Maldi (Method 20) of the compound treated according to Method 9. |
| 9 | N-{N-[(2R)-2-Amino-4,4-dimethylpent-1-yl]-β-tBu-Ala-de(1-D-leucine-2-leucine)-lysobactin trishydrofluoro acetate | | from Example 59A, 105 mg (47% of th.) HPLC (Method 15): $R_t$ = 3.91 min. LC/MS: (Method 17): $R_t$ = 1.61 min.; ES⁺: 646.3 [M + 2H]²⁺; ES⁻: 1290 [M − H]⁻. HR-MS: [M + H]⁺ found: 1290.7803 calc.: 1290.7785 |

-continued

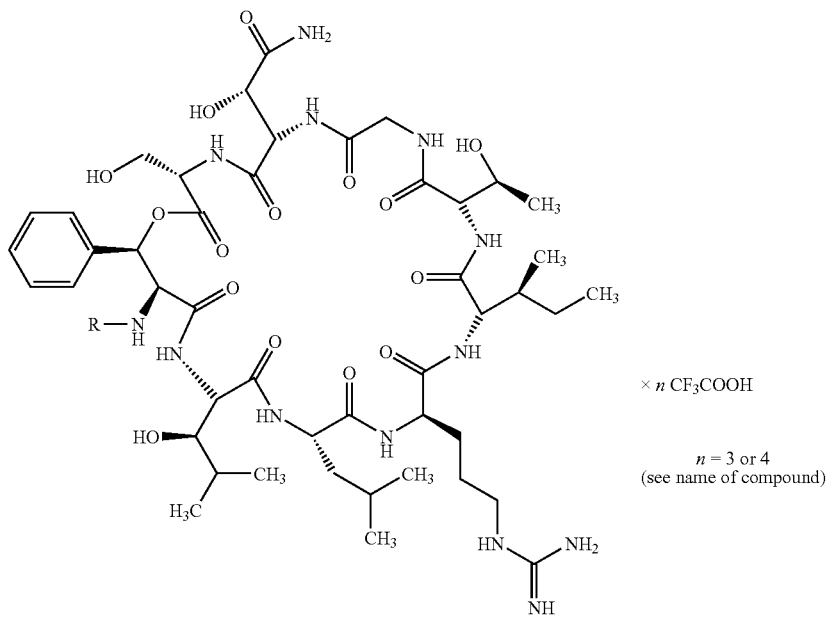

× n CF$_3$COOH n = 3 or 4
(see name of compound)

| Ex. No. | Name | R | Yield/analysis (Yield starting from Example 3A and 5A) |
|---|---|---|---|
| 10 | N-{N-[(2S)-2-Amino-4-methylpent-1-yl]-(β-3,4-dimethoxyphenyl-Ala)}de(1-D-leucine-2-leucine)-lysobactin trishydrotrifluoroacetate | | from Example 60A, 5 mg (13% of th.) LC/MS: (Method 14): $R_t$ = 1.23 min.; ES$^+$: 1356.7 [M + H]$^+$; ES$^-$: 1355 [M − H]$^-$, 1400.9 [M − H + HCOOH]$^-$. HR-MS: [M + H]$^+$ found: 1356.7549 calc.: 1356.7527 |
| 11 | N-{N-[(2R)-2-Amino-4-methylpent-1-yl]-(β-3,4-dimethoxyphenyl-Ala)}de(1-D-leucine-2-leucine)-lysobactintrishydrotrifluoroacetate | | from Example 61A, 5 mg (33% of th.) LC/MS: (Method 17): $R_t$ = 1.52 min.; ES$^+$: 1356 [M + H]$^+$, 679.3 [M + 2H]$^{2+}$; ES$^-$: 1355 [M − H]$^-$. HR-MS: [M + H]$^+$ found: 1356.7512 calc.: 1356.7527 |
| 12 | N-{N-[(2S)-2-Amino-4-methylpent-1-yl]-(β-3-pyridiyl-Ala)}de(1-D-leucine-2-leucine)-lysobactin tetrahydrotrifluoroacetate | | from Example 62A, 61 mg (22% of th.) HPLC (Method 15): $R_t$ = 3.30 min. LC/MS: (Method 17): $R_t$ = 1.23 min,; ES$^+$: 648.8 [M + 2H]$^{2+}$; ES$^-$: 1296 [M − H]$^-$, 1342 [M − H + HCOOH]$^-$. HR-MS: [M + H]$^+$ found: 1297.7244 calc.: 1297.7268 |

-continued

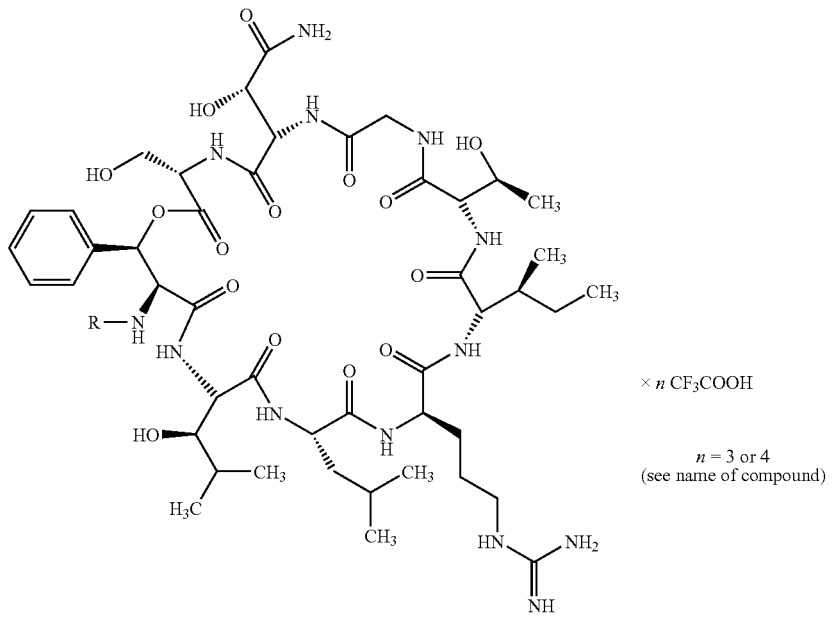

× n CF₃COOH n = 3 or 4
(see name of compound)

| Ex. No. | Name | R | Yield/analysis (Yield starting from Example 3A and 5A) |
|---|---|---|---|
| 13 | N-{N-[(2R)-2-Amino-4-methylpent-1-yl]-(β-3-pyridiyl-Ala)}de(1-D-leucine-2-leucine)-lysobactin tetrahydrotrifluoroacetate | ![R group structure with H₂N, isobutyl, and pyridyl substituents] | from Example 63A, 60 mg (19% of th.) LC/MS: (Method 17): R$_t$ = 1.25 min.; ES⁺: 649.7 [M + 2H]²⁺; ES⁻: 1296 [M − H]⁻, 1342 [M − H + HCOOH]⁻. HR-MS: [M + H]⁺ found: 1297.7301 calc.: 1297.7268 |
| 14 | N-{N-[(2R)-2-Amino-3-trimethylsilyl-prop-1-yl]-(β-trimethylsilyl)-Ala]}de(1-D-leucine-2-leucine)-lysobactin tris-hydrotrifluoroacetate | ![R group structure with H₂N and two trimethylsilyl groups] | from Example 64A, 8 mg (12% of th.) LC/MS: (Method 17): R$_t$ = 1.74 min.; ES⁺: 662.3 [M + 2H]²⁺; ES⁻: 1321 [M − H]⁻. HR-MS: [M + H]⁺ found: 1322.7292 calc.: 1322.7324 |
| 15 | N-{N-[(2R)-2-Amino-3-trimethylsilylprop-1-yl]-(β-tBu-Ala)}-de(1-D-leucine-2-leucine) lysobactin trishydrotrifluoroacetate | ![R group structure with H₂N, trimethylsilyl and tert-butyl groups] | from Example 65A, 17 mg (35% of th.) HPLC (Method 15): R$_t$ = 3.94 min. LC/MS: (Method 17): R$_t$ = 1.61 min.; ES⁺: 654.3 [M + 2H]²⁺; ES⁻: 1306 [M − H]⁻, 1352 [M − H + HCOOH]⁻. HR-MS: [M + H]⁺ found: 1306.7526 calc.: 1306.7555 |

-continued

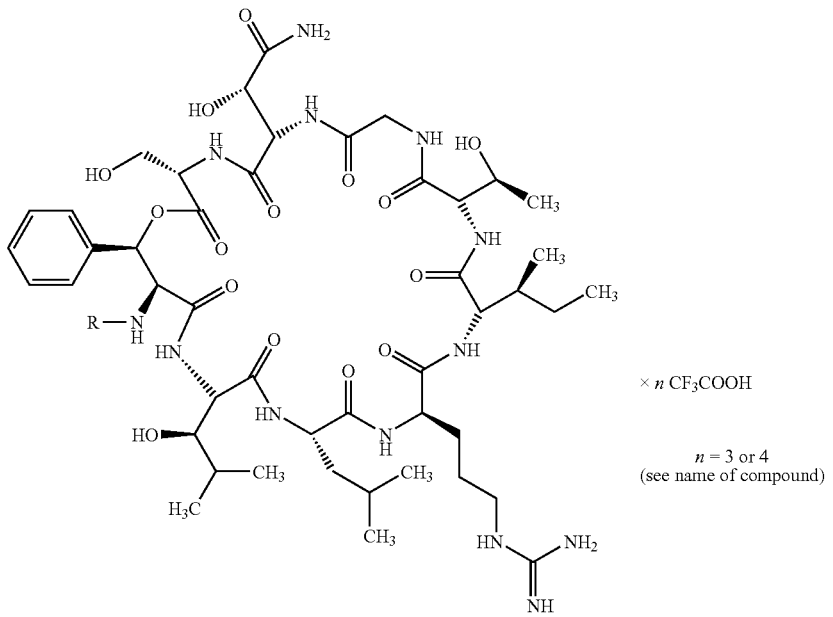

× n CF₃COOH n = 3 or 4
(see name of compound)

| Ex. No. | Name | R | Yield/analysis (Yield starting from Example 3A and 5A) |
|---|---|---|---|
| 16 | N-{N-[(2S)-2-Amino-4,4-di-methylpent-1-1-yl]-(β-trimethylsilyl-Ala)}de(1-D-leucine-2-leucine)-lysobactin tris-hydrotrifluoro-acetate | | from Example 66A, 24 mg (25% of th.) HPLC (Method 15): $R_t$ = 3.94 min. LC/MS: (Method 17): $R_t$ = 1.56 min.; ES⁺: 654.3 [M + 2H]²⁺; ES⁻: 1305 [M − H]⁻, 1351 [M − H + HCOOH]⁻. HR-MS: [M + H]⁺ found: 1306.7593 calc.: 1306.7555 |
| 17 | N-{N-[(2S)-2-Amino-4,4-dimethylpent-1-yl]-Asp(tBu)-de(1-D-leucine-2-leucine) lysobactin trishydrofluoro acetate | | from Example 67A, 43 mg (37% of th.) HPLC (Method 15): $R_t$ = 3.97 min. LC/MS: (Method 17): $R_t$ = 1.60 min.; ES⁺: 668.3 [M + 2H]²⁺; ES⁻: 1333 [M − H]⁻, 1379 [M − H + HCOOH]⁻. HR-MS: [M + H]⁺ found: 1334.7729 calc.: 1334.7684 |

Example 18

N-{N-[(2R,3S)-3-Amino-5,5-dimethylpent-2-yl]-β-tBu-Ala-de(1-D-leucine-2-leucine)lysobactin trishydrotrifluoroacetate

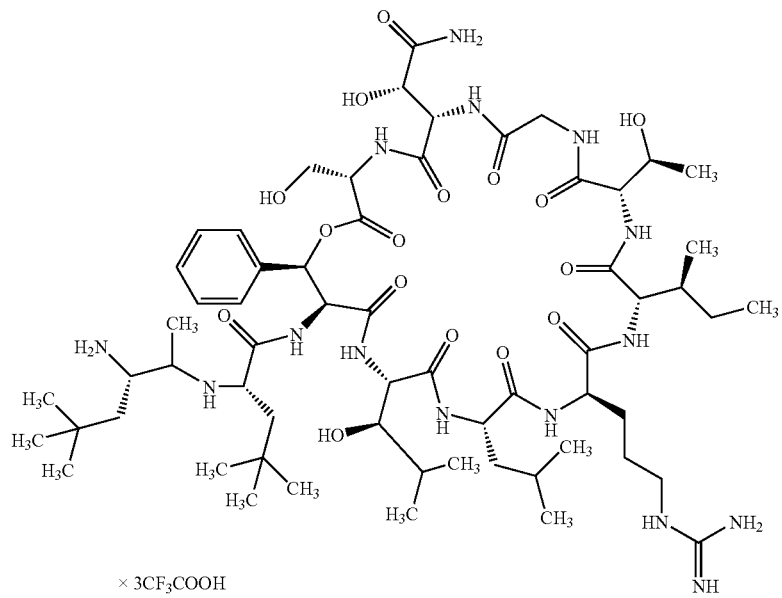

× 3CF$_3$COOH 5.7 mg (4.4 μmol) of the compound of Example 5A and 3.0 mg (6.6 μmol) of the compound of Example 71A are provided in 0.5 ml of DMSO under argon. 20 μl (4.5 eq.) of N-methylmorpholine, 2.7 mg (1.6 eq) of HATU and, after 15 min, a further 20 μl (4.5 eq.) of N-methylmorpholine are added. The mixture is stirred overnight at RT and then directly purified by means of preparative HPLC (Method 7). The fractions are checked by LC-MS (Method 17). After lyophilization of the suitable fractions ($R_t$=2.02, ES (pos): m/z=1440 [M+H]$^+$), the N-benzyloxycarbonyl-protected intermediate is immediately hydrogenated in 200 μl of isopropanol using 2 mg of palladium (10% on carbon) under 1 atm of hydrogen. After 4 h, the mixture is filtered, concentrated and purified by preparative HPLC (Method 10). 0.5 mg (7% of th.) of the title compound are obtained.

LC-MS (Method 17): $R_t$=1.53 min. ES$^+$: m/z=1290.7 [M+H]$^+$, 646 [M+2H]$^{2+}$, ES$^-$: m/z=1288.7 [M−H]$^-$, 644 [M−2H]$^-$.

B. Evaluation of the Physiological Activity

The in vitro activity of the compounds of the invention can be shown in the following assays:

Determination of the Minimum Inhibitory Concentration (MIC):

The MIC is determined in the liquid dilution test in accordance with the NCCLS guidelines. Overnight cultures of *Staphylococcus aureus* 133, *Entercococcus faecalis* 27159, *E. faecium* 4147 and *Streptococcus pneumoniae* G9a are incubated with the described test substances in a 1:2 dilution series. The MIC determination is carried out with a cell count of 105 microorganisms per ml in Isosensitest medium (Difco, Irvine/USA), with the exception of *S. pneumoniae*, which is tested in BHI broth (Difco, Irvine/USA) with 10% bovine serum at a cell count of 106 microorganisms per ml. The cultures are incubated at 37° C. for 18-24 hours, *S. pneumoniae* in the presence of 10% $CO_2$.

The lowest substance concentration in each case at which no visible bacterial growth occurs any more is defined as the MIC. The MIC values are reported in μg/ml.

Representative in-vitro activity data for the compounds of the invention are shown in Table A:

TABLE A

| Example No. | MIC *S. aureus* 133 | MIC *S. pneumoniae* | MIC *E. faecalis* ICB 27159 |
| --- | --- | --- | --- |
| 5 | 0.5 | 0.063 | 1 |
| 8 | 0.5 | 0.063 | 1 |
| 14 | 0.25 | 0.0156 | 0.125 |
| 15 | 0.5 | 0.063 | 1 |

The suitability of the compounds of the invention for the treatment of bacterial infections can be shown in the following animal model:

Systemic Infection with *Staphylococcus aureus* 133:

Cells of *S. aureus* 133 are grown overnight in BHI broth (Oxoid, N.Y./USA). The overnight culture is diluted 1:100 in fresh BHI broth and incubated for 3 hours. The cells which are then in the logarithmic growth phase are centrifuged off and washed twice with buffered, physiological saline. A cell suspension in saline is then adjusted photometrically to an extinction of 50 units. After a dilution step (1:15), this suspension is mixed 1:1 with a 10% mucin solution. 0.25 ml/20 g mouse of this infection solution are administered intraperitoneally (corresponding to 1×10$^6$ microorganisms/mouse). The therapy takes place intraperitoneally or intravenously 30 minutes after infection. Female CFW1 mice are used for the infection experiment. The survival of the animals is recorded over a period of 6 days.

The solubility of a compound is determined according to the methods known to the person skilled in the art.

C. Exemplary Embodiments of Pharmaceutical Compositions

The compounds of the invention can be converted into pharmaceutical preparations in the following ways:

Tablet:
Composition:
100 mg of the compound of Example 1, 50 mg of lactose (monohydrate), 50 mg of maize starch (native), 10 mg of polyvinylpyrrolidone (PVP 25) (BASF, Ludwigshafen, Germany) and 2 mg of magnesium stearate.

Tablet weight 212 mg. Diameter 8 mm, radius of curvature 12 mm.

Preparation:
The mixture of active compound, lactose and starch is granulated with a 5% solution (m/m) of the PVP in water. The granules are dried and then mixed with the magnesium stearate for 5 min after drying. This mixture is compressed with a conventional tablet press (see above for format of the tablet). A guideline for the compressive force used for the compression is 15 kN.

Orally Administrable Suspension:
Composition:
1000 mg of the compound of Example 1, 1000 mg of ethanol (96%), 400 mg of Rhodigel (xanthan gum from FMC, Pennsylvania, USA) and 99 g of water.

10 ml of oral suspension correspond to a single dose of 100 mg of the compound of the invention.

Preparation:
The Rhodigel is suspended in ethanol, and the active compound is added to the suspension. The water is added while stirring. The mixture is stirred for about 6 h until the swelling of the Rhodigel is complete.

Intravenously Administrable Solution:
Composition:
100-200 mg of the compound of Example 1, 15 g of polyethylene glycol 400 and 250 g of water for injection.

Preparation:
The compound of Example 1 is dissolved together with polyethylene glycol 400 in the water with stirring. The solution is sterilized by filtration (pore diameter 0.22 μm) and dispensed under aseptic conditions into heat-sterilized infusion bottles. The latter are closed with infusion stoppers and crimped caps.

What is claimed is:

1. A compound of formula (Ia)

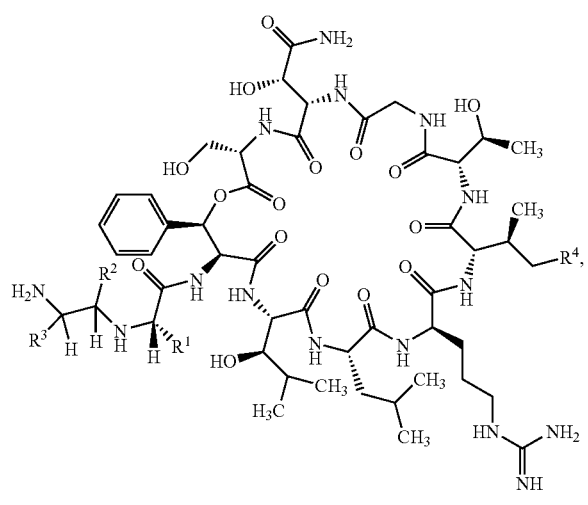

in which
R$^1$ is C$_1$-C$_2$-alkyl,
whereby C$_1$-C$_2$-alkyl is substituted with a substituent selected from the group consisting of trimethylsilyl, alkoxycarbonyl, C$_3$-C$_6$-cycloalkyl, alkoxy-substituted phenyl, 2-pyridyl and 3-pyridyl,
or
R$^1$ is C$_4$-C$_8$-alkyl,
R$^2$ is hydrogen or C$_1$-C$_4$-alkyl,
R$^3$ is C$_1$-C$_2$-alkyl,
whereby C$_1$-C$_2$-alkyl is substituted with a substituent trimethylsilyl,
or
R$^3$ is C$_4$-C$_6$-alkyl,
R$^4$ is hydrogen or methyl,
or one of its salts.

2. The compound of claim 1, corresponding to formula (I)

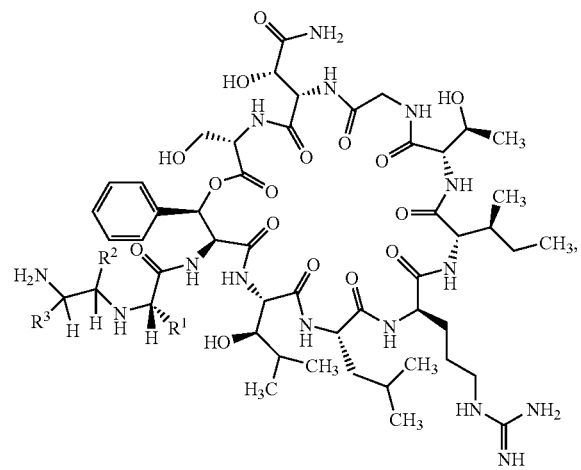

in which
R$^1$ is C$_1$-C$_2$-alkyl,
whereby C$_1$-C$_2$-alkyl is substituted with a substituent selected from the group consisting of trimethylsilyl, alkoxycarbonyl, C$_3$-C$_6$-cycloalkyl, alkoxy-substituted phenyl, 2-pyridyl and 3-pyridyl,
or
R$^1$ is C$_4$-C$_8$-alkyl,
R$^2$ is hydrogen or C$_1$-C$_4$-alkyl,
R$^3$ is C$_1$-C$_2$-alkyl,
whereby C$_1$-C$_2$-alkyl is substituted with a substituent trimethylsilyl,
or
R$^3$ is C$_4$-C$_6$-alkyl,
or one of its salts.

3. The compound of claim 2, whereby
R$^1$ is C$_1$-C$_2$-alkyl
whereby C$_1$-C$_2$-alkyl is substituted with a substituent trimethylsilyl,
or
R$^1$ is C$_4$-C$_6$-alkyl,
R$^2$ is hydrogen or methyl,
R$^3$ is C$_1$-C$_2$-alkyl,
whereby C$_1$-C$_2$-alkyl is substituted with a substituent trimethylsilyl, or $R^3$ is $C_4$-$C_6$-alkyl, or one of its salts.

4. The compound of claim 2, whereby $R^1$ is trimethylsilylmethyl or 2,2-dimethylprop-1-yl, $R^2$ is hydrogen, $R^3$ is trimethylsilylmethyl or 2,2-dimethylprop-1-yl, or one of its salts.

5. A method for preparing a compound of formula (Ia) of claim 1, whereby a compound of formula

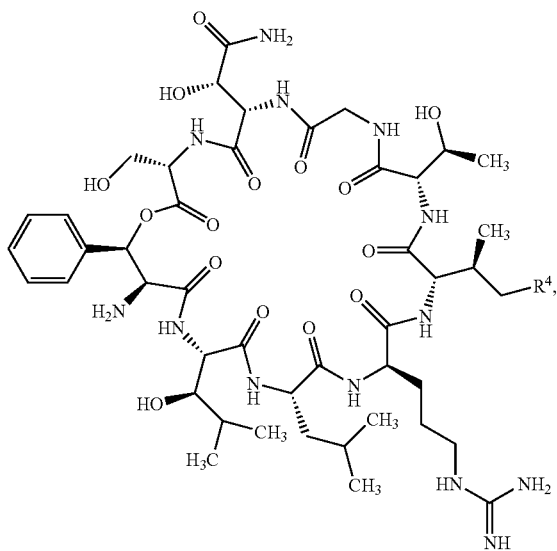

(II)

in which $R^4$ has the meaning indicated in claim 1, is reacted with a compound of formula

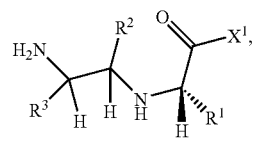

(III)

in which $R^1$, $R^2$ and $R^3$ have the meaning indicated in claim 1, and $X^1$ is halogen, or hydroxy.

6. A method for the production of a medicament for the treatment of diseases comprising mixing a compound of claim 1 with at least one inert, non-toxic, pharmaceutically acceptable excipient.

7. A method for the production of a medicament for the treatment of bacterial infections comprising mixing a compound of claim 1 with at least one inert, non-toxic, pharmaceutically acceptable excipient.

8. A medicament comprising a compound of claim 1 in combination with an inert, non-toxic, pharmaceutically acceptable excipient.

9. A method for treating bacterial infections in humans and animals by administering an antibacterially effective amount of at least one compound of claim 1.

10. A method for treating bacterial infections in humans and animals by administering an antibacterially effective amount of a medicament of claim 8.

11. A method for treating bacterial infections in humans and animals by administering an antibacterially effective amount of a medicament obtained by the method of claim 6.

12. A method for treating bacterial infections in humans and animals by administering an antibacterially effective amount of a medicament obtained by the method of claim 7.

13. The method of claim 5, wherein $X^1$ is bromine, chlorine, fluorine, or hydroxy.

* * * * *